US012595266B2

(12) United States Patent
Sikervar et al.

(10) Patent No.: US 12,595,266 B2
(45) Date of Patent: Apr. 7, 2026

(54) PESTICIDALLY ACTIVE HETEROCYCLIC DERIVATIVES WITH SULFUR CONTAINING SUBSTITUENTS

(71) Applicant: SYNGENTA CROP PROTECTION AG, Basel (CH)

(72) Inventors: Vikas Sikervar, Bracknell (GB); Swarnendu Sasmal, Corlim (IN); Michel Muehlebach, Stein (CH); André Stoller, Stein (CH); Daniel Emery, Stein (CH); André Jeanguenat, Stein (CH); Anke Buchholz, Stein (CH); Benedikt Kurtz, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 489 days.

(21) Appl. No.: 18/043,740

(22) PCT Filed: Sep. 1, 2021

(86) PCT No.: PCT/EP2021/074165

§ 371 (c)(1),
(2) Date: Mar. 2, 2023

(87) PCT Pub. No.: WO2022/049146

PCT Pub. Date: Mar. 10, 2022

(65) Prior Publication Data

US 2023/0265102 A1 Aug. 24, 2023

(30) Foreign Application Priority Data

Sep. 2, 2020 (IN) ............................ 202011037855
Nov. 10, 2020 (IN) ............................ 202011049100

(51) Int. Cl.

| | |
|---|---|
| ***C07D 491/056*** | (2006.01) |
| ***A01N 43/90*** | (2006.01) |
| ***A01P 7/04*** | (2006.01) |

(52) U.S. Cl.

CPC ......... *C07D 491/056* (2013.01); *A01N 43/90* (2013.01); *A01P 7/04* (2021.08)

(58) Field of Classification Search

CPC ................................................ C07D 491/056
See application file for complete search history.

(56) References Cited

U.S. PATENT DOCUMENTS 10,986,840 B2 4/2021 Fischer et al.

FOREIGN PATENT DOCUMENTS

| | | | |
|---|---|---|---|
| JP | 2018-523664 A | | 8/2018 |
| WO | 2019131575 A1 | | 7/2019 |
| WO | 2020013147 A1 | | 1/2020 |
| WO | 2020174094 A1 | | 9/2020 |
| WO | WO2022013417 A1 | * | 1/2022 |
| WO | WO2022017975 A1 | * | 1/2022 |

OTHER PUBLICATIONS

WIPO; App. No. PCT/EP2021/074165; International Search Report and Written Opinion mailed Dec. 1, 2021; pp. 1-9.
Japanese Office Action dated Aug. 4, 2025; 3 pages.

* cited by examiner

*Primary Examiner* — Adam C Milligan
*Assistant Examiner* — Karen Cheng
(74) *Attorney, Agent, or Firm* — BakerHostetler; Toni-Junell Herbert

(57) ABSTRACT

Compounds of the formula (I) wherein Q is as defined in claim 1. Furthermore, the present invention relates to agrochemical compositions which comprise compounds of formula (I), to preparation of these compositions, and to the use of the compounds or compositions in agriculture or horticulture for combating, preventing or controlling animal pests, including arthropods and in particular insects, molluscs, nematodes or representatives of the order Acarina.

(I)

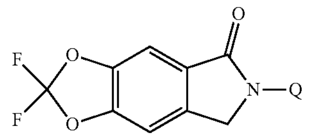

23 Claims, No Drawings

PESTICIDALLY ACTIVE HETEROCYCLIC DERIVATIVES WITH SULFUR CONTAINING SUBSTITUENTS

CROSS-REFERENCE TO RELATED APPLICATIONS

This application is a U.S. National Stage Application, filed under 35 U.S.C. § 371, of International Application No. PCT/EP2021/074165, filed Sep. 1, 2021, which claims priority to IN 202011049100, filed Nov. 10, 2020, and IN 202011037855, filed Sep. 2, 2020, the entire contents of which are incorporated by reference herein.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order Acarina.

Heterocyclic benzannulated dihydropyrrolone and phtalimide derivatives with sulfur-containing substituents have been described in the literature, for example in *J. Org. Chem.* 2003, 62, 8240 and *Bull. Chem Soc. Chim. Belg.* 1997, 106, 151. However, none of these references have described to have a pesticidal effect. Structurally different pesticidally active heterocyclic derivatives with sulfur-containing substituents have been described, for example in WO2012/012086848, WO2013/018928, WO2019/131575 and WO2020/013147.

It has now surprisingly been found that certain novel pesticidally active derivatives with sulfur containing substituents have favorable properties as pesticides.

The present invention therefore provides compounds of formula I, (I)

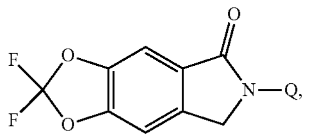

wherein

Q is a radical selected from the group consisting of formula Qa, Qb and Qc,

Qa

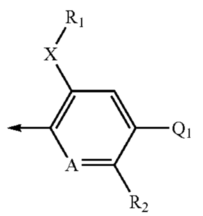

Qb

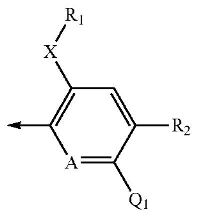

-continued

Qc

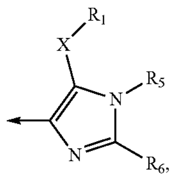

wherein the arrow denotes the point of attachment to the nitrogen atom of the tricyclic ring;

and wherein A represents CH or N;

X is S, SO, or $SO_2$;

$R_1$ is $C_1$-$C_4$alkyl, or $C_3$-$C_6$cycloalkyl-$C_1$-$C_4$alkyl;

$Q_1$ is hydrogen, halogen, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$cyanoalkoxy, $C_1$-$C_6$haloalkoxy, —$N(R_3)_2$, —$N(R_3)C(=O)R_4$, —$N(R_3)CON(R_3)_2$, (oxazolidin-2-one)-3-yl, or 2-pyridyloxy; or $Q_1$ is a five- to six-membered aromatic or heteroaromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $Q_1$ is a five-membered heteroaromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_2$ is hydrogen or $C_1$-$C_4$alkyl;

each $R_3$ independently is hydrogen, $C_1$-$C_4$alkyl, $C_1$-$C_6$haloalkyl or $C_3$-$C_6$cycloalkyl;

$R_5$ is $C_1$-$C_4$alkyl;

$R_6$ is hydrogen, halogen, $C_1$-$C_4$alkyl, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$alkoxy, $C_1$-$C_6$haloalkoxy, —$CO(NR_3R_4)$, —$NR_3COR_4$, ($C_3$-$C_8$)cycloalkyl-($C_1$-$C_6$)alkyl-, ($C_3$-$C_8$)cycloalkyl monosubstituted by cyano-($C_1$-$C_6$)alkyl-; or $R_6$ is a five- to six-membered saturated, partially saturated, or heteroaromatic ring system, linked via a ring nitrogen atom to the imidazole ring which is connected to the substitutent $R_5$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl-, ($C_3$-$C_8$)cycloalkyl monosubstituted by cyano-($C_1$-$C_6$)alkyl-, and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom; or $R_6$ is a five- to six-membered saturated, partially saturated, aromatic or heteroaromatic ring system linked via a ring carbon atom to the imidazole ring which is connected to the substitutent $R_5$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl-, ($C_3$-$C_8$)cycloalkyl monosubstituted by cyano-($C_1$-$C_6$)alkyl-, and said ring system can contain 1, 2 or 3 ring heteroatoms selected from the group consisting of nitrogen, oxygen and sulfur, where said ring system may not contain more than one ring oxygen atom and may not contain more than one ring sulfur atom; and $R_4$ is $C_3$-$C_6$cycloalkyl-$C_1$-$C_4$alkyl, $C_1$-$C_6$haloalkyl, $C_1$-$C_6$haloalkoxy or $C_3$-$C_6$cycloalkyl.

The present invention also provides agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

Where substituents are indicated as being itself further substituted, this means that they carry one or more identical or different substituents, e.g. one to four substituents. Normally not more than three such optional substituents are present at the same time. Preferably not more than two such substituents are present at the same time (i.e. the group is substituted by one or two of the substituents indicated). Where the additional substituent group is a larger group, such as cycloalkyl or phenyl, it is most preferred that only one such optional substituent is present. Where a group is indicated as being substituted, e.g. alkyl, this includes those groups that are part of other groups, e.g. the alkyl in alkylthio.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$-fluoroalkyl" would refer to a $C_1$-$C_2$-alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or penta-fluoroethyl.

The term "$C_1$-$C_n$alkoxy" as used herein refers to a straight-chain or branched saturated alkyl radical having 1 to n carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1,1-dimethylethoxy.

The term "$C_1$-$C_n$haloalkoxy" as used herein refers to a $C_1$-$C_n$alkoxy radical as mentioned above which is partially or fully substituted by fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, or 4-bromobutoxy.

The term "$C_1$-$C_n$-alkylsulfanyl" as used herein refers to a straight chain or branched saturated alkyl radical having 1 to n carbon atoms (as mentioned above) which is attached via a sulfur atom, i.e., for example, any one of methylthio, ethylthio, n-propylthio, 1-methylethylthio, butylthio, 1-methylpropylthio, 2-methylpropylthio or 1,1-dimethylethylthio.

The term "$C_1$-$C_n$alkylsulfinyl" as used herein refers to a straight chain or branched saturated alkyl radical having 1 to n carbon atoms (as mentioned above) which is attached via the sulfur atom of the sulfinyl group, i.e., for example, any one of methylsulfinyl, ethylsulfinyl, n-propylsulfinyl, 1-methylethyl-sulfinyl, n-butylsulfinyl, 1-methylpropylsulfinyl, 2-methylpropylsulfinyl, 1,1-dimethyl-ethylsulfinyl, n-pentylsulfinyl, 1-methylbutylsulfinyl, 2-methylbutylsulfinyl, 3-methyl-butylsulfinyl, 1,1-dimethylpropylsulfinyl, 1,2-dimethylpropylsulfinyl, 2,2-dimethylpropylsulfinyl or 1-ethylpropylsulfinyl.

The term "$C_1$-$C_n$alkylsulfonyl" as used herein refers to a straight chain or branched saturated alkyl radical having 1 to n carbon atoms (as mentioned above) which is attached via the sulfur atom of the sulfonyl group, i.e., for example, any one of methylsulfonyl, ethylsulfonyl, n-propylsulfonyl, isopropylsulfonyl, n-butylsulfonyl, 1-methylpropylsulfonyl, 2-methylpropylsulfonyl ort-butylsulphonyl.

The term "$C_1$-$C_n$cyanoalkyl" as used herein refers to a straight chain or branched saturated alkyl radicals having 1 to n carbon atoms (as mentioned above) which is substituted by a cyano group, for example cyanomethylene, cyanoethylene, 1,1-dimethylcyanomethyl, cyanomethyl, cyanoethyl, and 1-dimethylcyanomethyl.

The term "$C_3$-$C_n$cycloalkyl" as used herein refers to saturated or partially unsaturated mono-, bi- or tricyclic hydrocarbons having 3 to n carbon atoms, preferably 3 to 8 carbon atoms, for example cyclopropyl, cyclobutyl, cyclopentyl, cyclohexyl, cycloheptyl, cyclooctyl, bicyclo[2.2.1]heptyl and bicyclo[2.2.2]octyl.

The term "$C_3$-$C_n$cycloalkyl" monosubstituted by cyano as used herein refers to saturated or partially unsaturated mono-, bi- or tricyclic hydrocarbons having 3 to n carbon atoms (as mentioned above) which is substituted by a cyano group.

The suffix "—$C_1$-$C_n$alkyl" after terms such as "$C_3$-$C_n$cycloalkyl", wherein n is an integer from 1-6, as used herein refers to a straight chain or branched saturated alkyl radicals which is substituted by $C_3$-$C_n$cycloalkyl. An example of $C_3$-$C_n$cycloalkyl-$C_1$-$C_n$alkyl is for example, cyclopropylmethyl.

Halogen is generally fluorine, chlorine, bromine or iodine. This also applies, correspondingly, to halogen in combination with other meanings, such as haloalkyl.

In the context of this invention "mono- or polysubstituted" in the definition of the $Q_1$ or $R_6$ substituents, means typically, depending on the chemical structure of the substituents, monosubstituted to five-times substituted, more preferably mono-, double- or triple-substituted.

In the context of the this invention, the phrase "$Q_1$ is a five- to six-membered aromatic ring system, linked via a ring carbon atom to the ring which contains the substituent A . . . " and the phrase "$Q_1$ is a five-membered aromatic ring system linked via a ring nitrogen atom to the ring which contains the substituent A . . . ," as the case may be, refer to the manner of attachment of particular embodiments of the substituent $Q_1$ to the radical Q as represented by either formula Qa or formula Qb, as the case may be.

In the context of the this invention, the phrase "$R_6$ is a five- to six-membered saturated, partially saturated, or heteroaromatic ring system, linked via a ring carbon atom to the imidazole ring which is connected to the substitutent $R_5$ . . . " and the phrase "$R_6$ is a five- to six-membered saturated, partially saturated, heteroaromatic ring system linked via a ring nitrogen atom to the imidazole ring which is connected to the substitutent $R_5$ . . . ," as the case may be, refer to the manner of attachment of particular embodiments of the substituent $R_6$ to the radical Q as represented by either formula Qc in the formula I, as the case may be.

In the context of this invention, examples of "$Q_1$ is a five- to six-membered aromatic ring system, linked via a ring carbon atom to the ring which contains the substituent A, . . . ; and said ring system can contain 1, 2 or 3 ring heteroatoms . . . " are, but not limited to, phenyl, pyrazolyl, triazolyl, pyridinyl and pyrimidinyl; preferably phenyl, 2-pyridyl, 3-pyridyl, 4-pyridyl, pyrimidin-2-yl, pyrimidin-4-yl, and pyrimidin-5-yl.

In the context of this invention, examples of a "$Q_1$ is a five-membered aromatic ring system linked via a ring nitrogen atom to the ring which contains the substituent A, . . . ; and said ring system contains 1, 2 or 3 ring heteroatoms . . . " are, but not limited to, pyrazolyl, pyrrolyl, imidazolyl and triazolyl; preferably pyrrol-1-yl, pyrazol-1-yl, triazol-2-yl, 1,2,4-triazol-1-yl, triazol-1-yl, and imidazol-1-yl.

In the context of this invention, examples of "$R_6$ is a five- to six-membered saturated, partially saturated, aromatic or heteroaromatic ring system, linked via a ring carbon atom to the imidazole ring which is connected to the substitutent $R_5$, . . . "; and said ring system can contain 1, 2 or 3 ring heteroatoms . . . " are, but not limited to, phenyl, pyrazolyl, imidazolyl, triazolyl, pyridinyl, isoxazolyl, dihydroisoxazolyl, oxazolyl and pyrimidinyl.

In the context of this invention, examples of a "$R_6$ is a five- to six membered saturated, partially saturated, heteroaromatic ring system linked via a ring nitrogen atom to the imidazole ring which is connected to the substitutent $R_5$, . . . ; and said ring system contains 1, 2 or 3 ring heteroatoms . . . " are, but not limited to, pyrazolyl, pyrrolyl, imidazolyl and triazolyl.

Certain embodiments according to the invention are provided as set out below.

Embodiment 1 provides compounds of formula I, or an agrochemically acceptable salt, stereoisomer, enantiomer, tautomer or N-oxide thereof, as defined above.

Embodiment 2 provides compounds, or an agrochemically acceptable salt, stereoisomer, enantiomer, tautomer or N-oxide thereof, according to embodiment 1 wherein Q is Qa and having preferred definitions of $R_1$, $R_2$, X, A, $Q_1$, $R_3$ and $R_4$ as set out below.

Embodiment 3 provides compounds, or an agrochemically acceptable salt, stereoisomer, enantiomer, tautomer or N-oxide thereof, according to embodiment 1 wherein Q is Qb and having preferred definitions of $R_1$, $R_2$, X, A, $Q_1$, $R_3$ and $R_4$ as set out below.

Embodiment 4 provides compounds, or an agrochemically acceptable salt, stereoisomer, enantiomer, tautomer or N-oxide thereof, according to embodiment 1 wherein Q is Qc and having preferred definitions of $R_1$, $R_5$, $R_6$, X, $R_3$ and $R_4$ as set out below.

With respect to embodiments 1-4, preferred definitions of $R_1$, $R_2$, X, A, $Q_1$, $R_5$, $R_6$, $R_3$ and $R_4$ are, in any combination thereof, as set out below:

Preferably A is N or CH.

Most preferably A is N.

Preferably X is S or $SO_2$.

Most preferably X is $SO_2$.

Preferably $R_1$ is $C_1$-$C_4$alkyl or $C_3$-$C_6$cycloalkyl-$C_1$-$C_4$alkyl.

More preferably $R_1$ is $C_1$-$C_4$alkyl.

Even more preferably $R_1$ is ethyl or cyclopropylmethyl.

Most preferably $R_1$ is ethyl.

When Q is Qa, preferably $Q_1$ is hydrogen, halogen, $C_1$-$C_6$haloalkyl, $C_3$-$C_6$cycloalkyl, $C_3$-$C_6$cycloalkyl mono-substituted by cyano, $C_1$-$C_6$cyanoalkyl, $C_1$-$C_6$haloalkoxy, —$N(R_3)_2$, —$N(R_3)COR_4$, —$N(R_3)CON(R_3)_2$, (oxazolidin-2-one)-3-yl or 2-pyridyloxy;

Also preferred is when $Q_1$ is a five- to six-membered aromatic ring system linked via a ring carbon atom to the ring which contains the substituent A, said ring system is unsubstituted or is mono-substituted by substituents selected from the group consisting of halogen and $C_1$-$C_4$haloalkyl; and said ring system can contain 1 or 2 ring nitrogen atoms;

Also preferred is when $Q_1$ is a five-membered aromatic ring system linked via a ring nitrogen atom to the ring which contains the substituent A, said ring system is unsubstituted or is mono-substituted by substituents selected from the group consisting of halogen and $C_1$-$C_4$haloalkyl; and said ring system contains 2 or 3 ring nitrogen atoms.

More preferably $Q_1$ is hydrogen, halogen, trifluoromethyl, cyclopropyl, cyanocyclopropyl, cyanoisopropyl, trifluoroethoxy, (oxazolidin-2-one)-3-yl, 2-pyridyloxy, N-linked pyrazolyl which can be mono-substituted by chloro or trifluoromethyl, N-linked triazolyl, C-linked pyrimidinyl, —$N(R_3)_2$, —$N(R_3)COR_4$, or —$N(R_3)CON(R_3)_2$, in each of which $R_3$ is independently either hydrogen or methyl and $R_4$ is either methyl, ethyl or cyclopropyl.

Most preferably $Q_1$ is hydrogen, bromine, trifluoromethyl, cyclopropyl, 1-cyanocyclopropyl, 1-cyano-1-methyl-ethyl, 2,2,2-trifluoroethoxy, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, 2-pyridyloxy, pyrazol-1-yl, 3-chloro-pyrazol-1-yl, 3-trifluoromethyl-pyrazol-1-yl, 1,2,4-triazol-1-yl or pyrimidin-2-yl.

Also preferred is when $Q_1$ is selected from the group consisting of cyclopropyl; cyanocyclopropyl; cyanoisopropyl; cyanoisopropoxy; $C_1$-$C_6$haloalkyl, preferably trifluoromethyl or difluoroethyl; $C_1$-$C_6$haloalkoxy, preferably trifluoroethoxy or difluoropropoxy; —$N(CH_3)COCH_3$; N-linked triazolyl; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —$(CH_2)$-cyclopropyl, or —$(CH_2)$-cyanocyclopropyl; C-linked dihydroisoxazole which can be mono-substituted by cyclopropyl; and C-linked isoxazole which can be mono-substituted by cyclopropyl.

Further preferred is when $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4-triazol-4-yl; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl.

Preferably each $R_3$ independently is hydrogen or $C_1$-$C_4$alkyl.

Most preferably each $R_3$ independently is hydrogen or methyl.

Preferably $R_4$ is $C_1$-$C_6$alkyl or $C_3$-$C_6$cycloalkyl.

More preferably $R_4$ is methyl, ethyl or cyclopropyl.

Most preferably $R_4$ is methyl.

Preferably $R_2$ is hydrogen or $C_1$-$C_4$alkyl.

More preferably $R_2$ is hydrogen or methyl.

Most preferably $R_2$ is hydrogen.

When Q is Qb, preferably $Q_1$ is hydrogen, halogen, $C_3$-$C_6$cycloalkyl, —$N(R_3)_2$, —$N(R_3)COR_4$, —$N(R_3)CON(R_3)_2$, or (oxazolidin-2-one)-3-yl;

Also preferred is when $Q_1$ is a five- to six-membered aromatic ring system linked via a ring carbon atom to the ring which contains the substituent A, said ring system is unsubstituted or is mono-substituted by substituents selected from the group consisting of halogen and $C_1$-$C_4$haloalkyl; and said ring system can contain 1 or 2 ring nitrogen atoms;

Also preferred is when $Q_1$ is a five-membered aromatic ring system linked via a ring nitrogen atom to the ring which contains the substituent A, said ring system is unsubstituted or is mono-substituted by substituents selected from the group consisting of halogen and $C_1$-$C_4$haloalkyl; and said ring system contains 2 or 3 ring nitrogen atoms.

More preferably $Q_1$ is hydrogen, halogen, cyclopropyl, (oxazolidin-2-one)-3-yl, N-linked pyrazolyl which can be mono-substituted by chloro or trifluoromethyl, N-linked triazolyl, C-linked pyrimidinyl, —$N(R_3)_2$, —$N(R_3)COR_4$, or —$N(R_3)CON(R_3)_2$, in each of which $R_3$ is independently either hydrogen or methyl and $R_4$ is either methyl, ethyl or cyclopropyl.

Most preferably $Q_1$ is hydrogen, bromine, cyclopropyl, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, pyrazol-1-yl, 3-chloro-pyrazol-1-yl, 3-trifluoromethyl-pyrazol-1-yl, 1,2,4-triazol-1-yl or pyrimidin-2-yl.

Also prefered is when $Q_1$ is selected from the group consisting of cyclopropyl; cyanocyclopropyl; cyanoisopropyl; cyanoisopropoxy; $C_1$-$C_6$haloalkyl, preferably trifluoromethyl or difluoroethyl; $C_1$-$C_6$haloalkoxy, preferably trifluoroethoxy or difluoropropoxy; —$N(CH_3)COCH_3$; N-linked triazolyl; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —$(CH_2)$-cyclopropyl, or —$(CH_2)$-cyanocyclopropyl; C-linked dihydroisoxazole which can be mono-substituted by cyclopropyl; and C-linked isoxazole which can be mono-substituted by cyclopropyl.

Further prefered is when $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4-triazol-4-yl; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl;

1-cyclopropylmethylpyrazol-4-yl; 1-(1-cyanocyclopropylmethyl)pyrazol-4-yl; 3-cyclopropyl-4,5-dihydro-isoxazol-5-yl; and 3-cyclopropyl-isoxazol-5-yl.

When Q is Qc, preferably $R_5$ is $C_1$-$C_4$alkyl.

More preferably $R_5$ is methyl or ethyl.

Most preferably $R_5$ is methyl.

Preferably $R_6$ is hydrogen, halogen, $C_3$-$C_6$cycloalkyl, $C_1$-$C_6$haloalkoxy, —$CO(NR_3R_4)$, or —$NR_3COR_4$;

Also preferred is when $R_6$ is a five-membered heteroaromatic ring system, linked via a ring nitrogen atom to the imidazole ring which is connected to the substitutent $R_5$, said ring system is unsubstituted or is mono-substituted by substituents selected from the group consisting of halogen, $C_3$-$C_6$cycloalkyl, or $C_1$-$C_4$haloalkyl, and said ring system contains 2 ring nitrogen atoms; or Also preferred is when $R_6$ is a five- to six-membered partially saturated, aromatic or heteroaromatic ring system, linked via a ring carbon atom to the imidazole ring which is connected to the substitutent $R_5$, said ring system is unsubstituted or is mono-substituted by substituents selected from the group consisting of $C_1$-$C_4$haloalkyl, $C_3$-$C_6$cycloalkyl, $C_3$-$C_6$cycloalkyl mono-substituted by cyano, ($C_3$-$C_8$)cycloalkyl-($C_1$-$C_6$)alkyl-, or ($C_3$-$C_8$)cycloalkyl monosubstituted by cyano-($C_1$-$C_6$)alkyl-, and said ring system can contain 2 ring heteroatoms selected from the group consisting of nitrogen and oxygen, where said ring system may not contain more than one ring oxygen atom.

More preferably $R_6$ is hydrogen, halogen, cyclopropyl, trifluoroethoxy, —$CO(NR_3R_4)$ or —$NR_3COR_4$, in each of which $R_3$ is methyl and $R_4$ is trifluoroethoxy, N-linked pyrazolyl which can be mono-substituted by chloro, cyclopropyl or trifluoromethyl, C-linked pyrimidinyl, C-linked pyrazolyl which can be mono-substituted by cyclopropyl, difluoromethyl, difluoroethyl, cyanocyclopropylmethyl or cyclopropylmethyl, C-linked dihydroisoxazole which can be mono-substituted by chloro, trifluoromethyl or cyclopropyl, phenyl which can be mono-substituted by chloro, fluoro, cylopropyl or cylopropyl mono-substituted with cyano.

Most preferably $R_6$ is hydrogen, cyclopropyl, 2,2,2-trifluoroethoxy, —$CONCH_3(CH_2CF_3)$, —$N(CH_3)COCH_2CF_3$, or a substituent selected from J1 to J12

J1

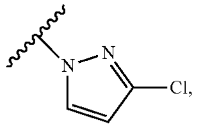

J2

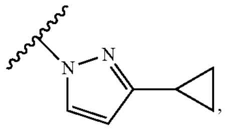

J3

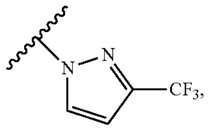

J4

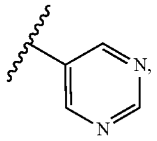

-continued

J5

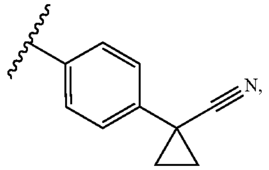

J6

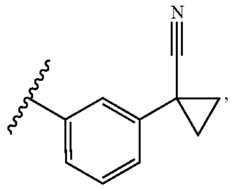

J7

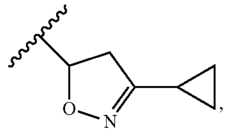

J8

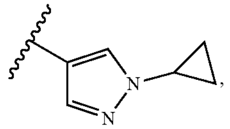

J9

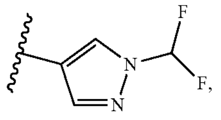

J10

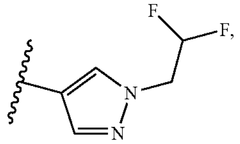

J11

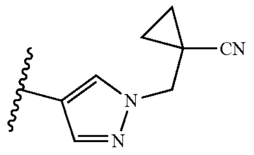

and

J12

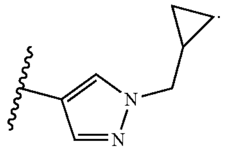

Also preferred is when $R_6$ is selected from the group consisting of cyclopropyl; cyanocyclopropyl; cyanoisopropyl; cyanoisopropoxy; $C_1$-$C_6$haloalkyl, preferably trifluoromethyl or difluoroethyl; $C_1$-$C_6$haloalkoxy, preferably trifluoroethoxy or difluoropropoxy; —$N(CH_3)COCH_3$; N-linked triazolyl; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —($CH_2$)-cyclopropyl, or —($CH_2$)-cyanocyclopropyl; C-linked dihydroisoxazole which can be mono-substituted by cyclopropyl; and C-linked isoxazole which can be mono-substituted by cyclopropyl.

Further prefered is when $R_6$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoro-propoxy; —$N(CH_3)COCH_3$; 1,2,4-triazol-1-yl; 1,2,4-triazol-4-yl; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl) pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl.

Preferably each $R_3$ independently is $C_1$-$C_4$alkyl.

Most preferably each $R_3$ independently is methyl.

Preferably $R_4$ is independently $C_1$-$C_6$alkyl, $C_1$-$C_6$haloalkyl or $C_1$-$C_6$haloalkoxy.

Most preferably $R_4$ is independently methyl or —$CH_2CF_3$.

Further embodiments according to the invention are provided as set forth below.

A preferred group of compounds of formula I is represented by the compounds of formula I-A1

I-A1

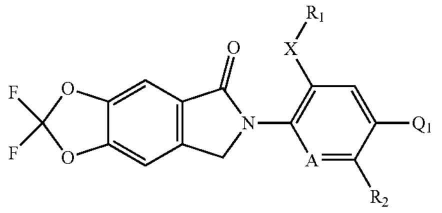

wherein A, $R_1$, $R_2$, X, $Q_1$, $R_3$ and $R_4$ are as defined under formula I above.

In one preferred group of compounds of formula I-A1, A is CH or N; $R_1$ is $C_1$-$C_4$alkyl or $C_3$-$C_6$cycloalkyl-$C_1$-$C_4$alkyl; $R_2$ is hydrogen or $C_1$-$C_4$alkyl; X is S or $SO_2$; $Q_1$ is hydrogen, halogen, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$haloalkoxy, —$N(R_3)_2$, —$N(R_3)COR_4$, —$N(R_3)CON(R_3)_2$, (oxazolidin-2-one)-3-yl or 2-pyridyloxy; in which each $R_3$ independently is hydrogen or $C_1$-$C_4$alkyl; and $R_4$ is $C_1$-$C_6$alkyl or $C_3$-$C_6$cycloalkyl.

In another preferred group of compounds of formula I-A1, A is CH or N; $R_1$ is ethyl or cyclopropylmethyl; $R_2$ is hydrogen or methyl; X is S or $SO_2$; and $Q_1$ is hydrogen, bromine, trifluoromethyl, cyclopropyl, 1-cyanocyclopropyl, 1-cyano-1-methyl-ethyl, 2,2,2-trifluoroethoxy, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, or 2-pyridyloxy.

In another preferred group of compounds of formula I-A1, A is N; $R_1$ is ethyl; $R_2$ is hydrogen; X is $SO_2$; and $Q_1$ is hydrogen, bromine, trifluoromethyl, cyclopropyl, 1-cyano-cyclopropyl, 1-cyano-1-methyl-ethyl, 2,2,2-trifluoroethoxy, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, or 2-pyridyloxy.

In another further preferred group of compounds of formula I-A1, $Q_1$ is a five- to six-membered aromatic ring system linked via a ring carbon atom to the ring which contains the substituent A, said ring system is unsubstituted or is mono-substituted by substituents selected from the group consisting of halogen and $C_1$-$C_4$haloalkyl; and said ring system can contain 1 or 2 ring nitrogen atoms. In this embodiment, more preferably $Q_1$ is C-linked pyrimidinyl.

Also preferred compounds of formula I-A1 are those wherein $Q_1$ is a five-membered aromatic ring system linked via a ring nitrogen atom to the ring which contains the substituent A, said ring system is unsubstituted or is mono-substituted by substituents selected from the group consisting of halogen and $C_1$-$C_4$haloalkyl; and said ring system contains 2 or 3 ring nitrogen atoms. In this embodiment, more preferably $Q_1$ is N-linked pyrazolyl, which can be mono-substituted by chloro or trifluoromethyl; or $Q_1$ is N-linked triazolyl.

In compounds of formula I-A1 and all of the preferred embodiments of compounds of formula I-A1 mentioned above, unless otherwise specified, A, $R_1$, $R_2$, $R_3$, X, $Q_1$, and $R_4$ are as defined under formula I above; preferably A is CH or N, more preferably A is N; preferably $R_1$ is ethyl or cyclopropylmethyl, most preferably $R_1$ is ethyl; preferably X is S or $SO_2$, most preferably X is $SO_2$; preferably $R_2$ is hydrogen; preferably $Q_1$ is hydrogen, halogen, trifluoromethyl, cyclopropyl, cyanocyclopropyl, cyanoisopropyl, trifluoroethoxy, (oxazolidin-2-one)-3-yl, 2-pyridyloxy, N-linked pyrazolyl which can be mono-substituted by chloro or trifluoromethyl, N-linked triazolyl, C-linked pyrimidinyl, —$N(R_3)_2$, —$N(R_3)COR_4$, or —$N(R_3)CON(R_3)_2$, in each of which $R_3$ is independently either hydrogen or methyl and $R_4$ is either methyl, ethyl or cyclopropyl; more preferably $Q_1$ is hydrogen, bromine, trifluoromethyl, cyclopropyl, 1-cyano-cyclopropyl, 1-cyano-1-methyl-ethyl, 2,2,2-trifluoroethoxy, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, 2-pyridyloxy, pyrazol-1-yl, 3-chloro-pyrazol-1-yl, 3-trifluoromethyl-pyrazol-1-yl, 1,2,4-triazol-1-yl or pyrimidin-2-yl.

One further preferred group of compounds according to this embodiment are compounds of formula (I-A1-1), which are compounds of formula (I-A1) wherein, A is N; $R_1$ is ethyl; X is $SO_2$; $R_2$ is hydrogen; and preferably $Q_1$ is hydrogen, halogen, trifluoromethyl, cyclopropyl, cyanocyclopropyl, cyanoisopropyl, 2-pyridyloxy, N-linked pyrazolyl which can be mono-substituted by chloro or trifluoromethyl, or —$N(R_3)COR_4$ in which $R_3$ is methyl and $R_4$ is either methyl or ethyl; more preferably $Q_1$ is hydrogen, bromine, trifluoromethyl, cyclopropyl, 1-cyanocyclopropyl, 1-cyano-1-methyl-ethyl, —$N(CH_3)COCH_3$, 2-pyridyloxy, 3-chloro-pyrazol-1-yl or 3-trifluoromethyl-pyrazol-1-yl.

One further preferred group of compounds according to this embodiment are compounds of formula (I-A1-2), which are compounds of formula (I-A1) wherein, $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl;

Preferably, in formula (I-A1-2) $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4- triazol-4-yl; pyrimidin-5-yl; and pyrimidin-2-yl; more preferably, $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; and pyrimidin-2-yl.

Another preferred group of compounds of formula I is represented by the compounds of formula I-A2

I-A2

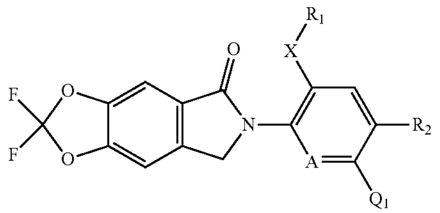

wherein A, $R_1$, $R_2$, X, $Q_1$, $R_3$ and $R_4$ are as defined under formula I above.

In one preferred group of compounds of formula I-A2, A is CH or N; $R_1$ is $C_1$-$C_4$alkyl or $C_3$-$C_6$cycloalkyl-$C_1$-$C_4$alkyl; $R_2$ is hydrogen or $C_1$-$C_4$alkyl; X is S or $SO_2$; $Q_1$ is hydrogen, halogen, $C_3$-$C_6$cycloalkyl, —$N(R_3)_2$, —$N(R_3)COR_4$, —$N(R_3)CON(R_3)_2$, or (oxazolidin-2-one)-3-yl; in which each $R_3$ independently is hydrogen or $C_1$-$C_4$alkyl; and $R_4$ is $C_1$-$C_6$alkyl or $C_3$-$C_6$cycloalkyl.

In another preferred group of compounds of formula I-A2, A is CH or N; $R_1$ is ethyl or cyclopropylmethyl; $R_2$ is hydrogen or methyl; X is S or $SO_2$; and $Q_1$ is hydrogen, bromine, cyclopropyl, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, or (oxazolidin-2-one)-3-yl.

In another preferred group of compounds of formula I-A2, A is N; $R_1$ is ethyl; $R_2$ is hydrogen; X is $SO_2$; and $Q_1$ is hydrogen, bromine, cyclopropyl, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, or (oxazolidin-2-one)-3-yl.

In another further preferred group of compounds of formula I-A2, $Q_1$ is a five- to six-membered aromatic ring system linked via a ring carbon atom to the ring which contains the substituent A, said ring system is unsubstituted or is mono-substituted by substituents selected from the group consisting of halogen and $C_1$-$C_4$haloalkyl; and said ring system can contain 1 or 2 ring nitrogen atoms. In this embodiment, more preferably $Q_1$ is C-linked pyrimidinyl.

Also preferred compounds of formula I-A2 are those wherein $Q_1$ is a five-membered aromatic ring system linked via a ring nitrogen atom to the ring which contains the substituent A, said ring system is unsubstituted or is mono-substituted by substituents selected from the group consisting of halogen and $C_1$-$C_4$haloalkyl; and said ring system contains 2 or 3 ring nitrogen atoms. In this embodiment, more preferably $Q_1$ is N-linked pyrazolyl which can be mono-substituted by chloro or trifluoromethyl; or $Q_1$ is N-linked triazolyl.

In compounds of formula I-A2 and all of the preferred embodiments of compounds of formula I-A2 mentioned above, unless otherwise specified, A, $R_1$, $R_2$, $R_3$, X, $Q_1$, and $R_4$ are as defined under formula I above; preferably A is CH or N, more preferably A is N; preferably $R_1$ is ethyl or cyclopropylmethyl, most preferably $R_1$ is ethyl; preferably X is S or $SO_2$, most preferably X is $SO_2$; preferably $R_2$ is hydrogen; preferably $Q_1$ is hydrogen, halogen, cyclopropyl, (oxazolidin-2-one)-3-yl, N-linked pyrazolyl which can be mono-substituted by chloro or trifluoromethyl, N-linked triazolyl, C-linked pyrimidinyl, —$N(R_3)_2$, —$N(R_3)COR_4$, or —$N(R_3)CON(R_3)_2$, in each of which $R_3$ is independently either hydrogen or methyl and $R_4$ is either methyl, ethyl or cyclopropyl; more preferably $Q_1$ is hydrogen, bromine, cyclopropyl, —$NH(CH_3)$, —$N(CH_3)COCH_3$, —$N(CH_3)COCH_2CH_3$, —$N(CH_3)CO$(cyclopropyl), —$N(H)CONH(CH_3)$, —$N(CH_3)CONH(CH_3)$, (oxazolidin-2-one)-3-yl, pyrazol-1-yl, 3-chloro-pyrazol-1-yl, 3-trifluoromethyl-pyrazol-1-yl, 1,2,4-triazol-1-yl or pyrimidin-2-yl.

One further preferred group of compounds according to this embodiment are compounds of formula (I-A2-1), which are compounds of formula (I-A2) wherein, A is N; $R_1$ is ethyl; X is $SO_2$; $R_2$ is hydrogen; and preferably $Q_1$ is hydrogen, halogen, cyclopropyl, N-linked pyrazolyl which can be mono-substituted by chloro or trifluoromethyl, N-linked triazolyl, C-linked pyrimidinyl, or —$N(R_3)COR_4$ in which $R_3$ is methyl and $R_4$ is either methyl or ethyl; more preferably $Q_1$ is hydrogen, bromine, cyclopropyl, —$N(CH_3)COCH_3$, 3-chloro-pyrazol-1-yl, 3-trifluoromethyl-pyrazol-1-yl, 1,2,4-triazol-1-yl or pyrimidin-2-yl.

One further preferred group of compounds according to this embodiment are compounds of formula (I-A2-2), which are compounds of formula (I-A2) wherein, $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)pyrazol-4-yl; 3-cyclopropyl-4,5-dihydro-isoxazol-5-yl; and 3-cyclopropyl-isoxazol-5-yl;

Preferably, in formula (I-A2-2) $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4-triazol-4-yl; pyrimidin-5-yl; and pyrimidin-2-yl; more preferably, $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; and pyrimidin-2-yl.

Another preferred group of compounds of formula I is represented by the compounds of formula I-B1

I-B1

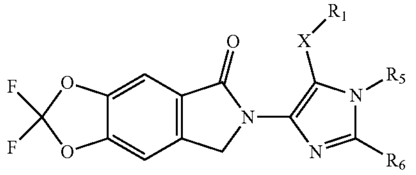

wherein X, $R_1$, $R_3$, $R_4$, $R_5$ and $R_6$ are as defined under formula I above.

In one preferred group of compounds of formula I-B1, X is S or $SO_2$; $R_1$ is $C_1$-$C_4$alkyl or $C_3$-$C_6$cycloalkyl-$C_1$-$C_4$alkyl; $R_5$ is $C_1$-$C_4$alkyl; $R_6$ is hydrogen, halogen, $C_3$-$C_6$cycloalkyl, $C_1$-$C_6$haloalkoxy, —CO($NR_3R_4$), or —$NR_3COR_4$; in which each $R_3$ independently is $C_1$-$C_4$alkyl; and each $R_4$ is independently $C_1$-$C_6$alkyl or $C_3$-$C_6$cycloalkyl.

In another preferred group of compounds of formula I-B1, X is S or $SO_2$; $R_1$ is ethyl or cyclopropylmethyl; $R_5$ is methyl or ethyl; and $R_6$ is hydrogen, cyclopropyl, 2,2,2-trifluoroethoxy, —$CONCH_3(CH_2CF_3)$, or —$N(CH_3)COCH_2CF_3$.

In another preferred group of compounds of formula I-B1, X is $SO_2$; $R_1$ is ethyl; $R_5$ is methyl; and $R_6$ is hydrogen, cyclopropyl, 2,2,2-trifluoroethoxy, —$CONCH_3(CH_2CF_3)$, or —$N(CH_3)COCH_2CF_3$.

In another further preferred group of compounds of formula I-B1, $R_6$ is a five-membered heteroaromatic ring system, linked via a ring nitrogen atom to the imidazole ring which is connected to the substitutent $R_5$, said ring system is unsubstituted or is mono-substituted by substituents selected from the group consisting of halogen, $C_3$-$C_6$cycloalkyl, or $C_1$-$C_4$haloalkyl, and said ring system contains 2 ring nitrogen atoms. In this embodiment, more preferably $R_6$ is N-linked pyrazolyl which can be mono-substituted by chloro, cyclopropyl or trifluoromethyl.

In another further preferred group of compounds of formula I-B1, $R_6$ is a five- to six-membered partially saturated, aromatic or heteroaromatic ring system, linked via a ring carbon atom to the imidazole ring which is connected to the substitutent $R_5$, said ring system is unsubstituted or is mono-substituted by substituents selected from the group consisting of $C_1$-$C_4$haloalkyl, $C_3$-$C_6$cycloalkyl, $C_3$-$C_6$cycloalkyl monosubstituted by cyano, ($C_3$-$C_8$)cycloalkyl-($C_1$-$C_6$)alkyl-, or ($C_3$-$C_8$)cycloalkyl monosubstituted by cyano-($C_1$-$C_6$)alkyl-, and said ring system can contain 2 ring heteroatoms selected from the group consisting of nitrogen and oxygen, where said ring system may not contain more than one ring oxygen atom. In this embodiment, more preferably $R_6$ is C-linked pyrimidinyl, C-linked pyrazolyl which can be mono-substituted by cyclopropyl, difluoromethyl, difluoroethyl, cyanocyclopropylmethyl or cyclopropylmethyl, C-linked dihydroisoxazole which can be mono-substituted by chloro, trifluoromethyl or cyclopropyl, phenyl which can be mono-substituted by chloro, fluoro, cylopropyl or cylopropyl mono-substituted with cyano.

In compounds of formula I-B1 and all of the preferred embodiments of compounds of formula I-B1 mentioned above, unless otherwise specified, X, $R_1$, $R_3$, $R_4$, $R_5$ and $R_6$ are as defined under formula I above; preferably X is S or $SO_2$, most preferably X is $SO_2$; preferably $R_1$ is ethyl or cyclopropylmethyl, most preferably $R_1$ is ethyl; preferably $R_6$ is hydrogen, cyclopropyl, 2,2,2-trifluoroethoxy, —$CONCH_3(CH_2CF_3)$, —$N(CH_3)COCH_2CF_3$, N-linked pyrazolyl which can be mono-substituted by chloro, cyclopropyl or trifluoromethyl, C-linked pyrimidinyl, C-linked pyrazolyl which can be mono-substituted by cyclopropyl, difluoromethyl, difluoroethyl, cyanocyclopropylmethyl or cyclopropylmethyl, C-linked dihydroisoxazole which can be mono-substituted by chloro, trifluoromethyl or cyclopropyl, phenyl which can be mono-substituted by chloro, fluoro, cylopropyl or cylopropyl mono-substituted with cyano; more preferably $R_6$ is hydrogen, cyclopropyl, 2,2,2-trifluoroethoxy, —$CONCH_3(CH_2CF_3)$, —$N(CH_3)COCH_2CF_3$, or a substituent selected from J1 to J12

J1

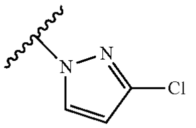

-continued

J2

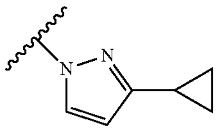

J3

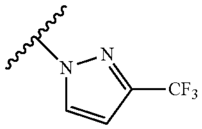

J4

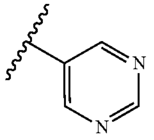

J5

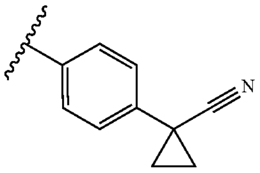

J6

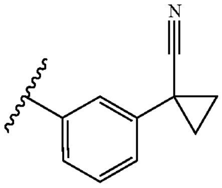

J7

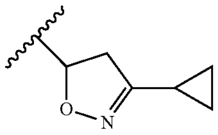

J8

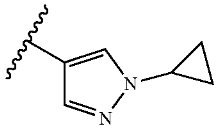

J9

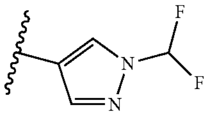

J10

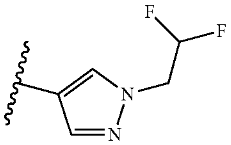

J11

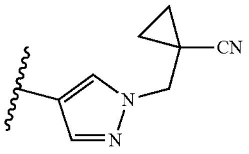

and

-continued

J12

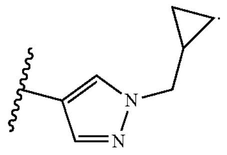

One further preferred group of compounds according to this embodiment are compounds of formula (I-B1-1), which are compounds of formula (I-B1) wherein, $R_6$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl.

Preferably, in formula (I-B1-1) $R_6$ is selected from the group consisting of cyclopropyl; 2,2,2-trifluoroethoxy; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)-pyrazol-4-yl; 3-cyclopropyl-4,5-dihydro-isoxazol-5-yl; and 3-cyclopropyl-isoxazol-5-yl; more preferably, $R_6$ is selected from the group consisting of cyclopropyl; 2,2,2-trifluoroethoxy; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl.

An outstanding group of compounds according to the invention are those of formula I-C (I-C)

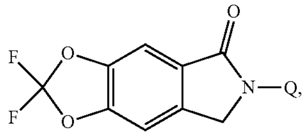

wherein

Q is a radical selected from the group consisting of formula Qa-1, Qb-1 and Qc-1, Qa-1

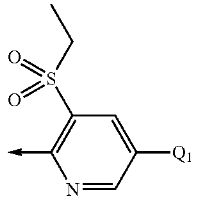

-continued

Qb-1

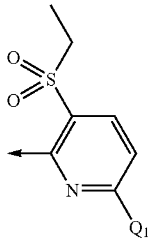

Qc-1

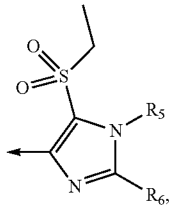

wherein the arrow denotes the point of attachment to the nitrogen atom of the tricyclic ring;

and wherein $R_5$ is $C_1$-$C_6$alkyl; preferably $R_5$ is methyl or ethyl; even more preferably $R_5$ is methyl; and each of $Q_1$ and $R_6$ are independently selected from the group consisting of cyclopropyl; cyanocyclopropyl; cyanoisopropyl; cyanoisopropoxy; $C_1$-$C_6$haloalkyl, preferably trifluoromethyl or difluoroethyl; $C_1$-$C_6$haloalkoxy, preferably trifluoroethoxy or difluoropropoxy; —$N(CH_3)COCH_3$; N-linked triazolyl; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —$(CH_2)$-cyclopropyl, or —$(CH_2)$-cyanocyclopropyl; C-linked dihydroisoxazole which can be mono-substituted by cyclopropyl; and C-linked isoxazole which can be mono-substituted by cyclopropyl.

One preferred group of compounds according to this embodiment are compounds of formula (I-C-1) which are compounds of formula (I-C), or any of the preferred embodiments of compounds of formula (I-C), wherein each of $Q_1$ and $R_6$ are independently selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4-triazol-4-yl; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropyl-methyl)pyrazol-4-yl; 3-cyclopropyl-4,5-dihydro-isoxazol-5-yl; and 3-cyclopropyl-isoxazol-5-yl.

Another preferred group of compounds according to this embodiment are compounds of formula (I-C-2) which are compounds of formula (I-C), or any of the preferred embodiments of compounds of formula (I-C), wherein each of $Q_1$ and $R_6$ are independently selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)pyrazol-4-yl; 3-cyclopropyl-4,5-dihydro-isoxazol-5-yl; and 3-cyclopropyl-isoxazol-5-yl.

Another outstanding group of compounds according to the invention are those of formula I-C1 which are compounds of formula (I-C) wherein $R_5$ is $C_1$-$C_6$alkyl; preferably $R_5$ is methyl or ethyl; even more preferably $R_5$ is methyl;

Q is a radical selected from the group consisting of formula Qa-1, Qb-1 and Qc-1, wherein the arrow denotes the point of attachment to the nitrogen atom of the tricyclic ring;

and wherein $Q_1$ is independently selected from the group consisting of cyclopropyl; cyanocyclopropyl; cyanoisopropyl; cyanoisopropoxy; $C_1$-$C_6$haloalkyl, preferably trifluoromethyl or difluoroethyl; $C_1$-$C_6$haloalkoxy, preferably trifluoroethoxy or difluoropropoxy; —$N(CH_3)COCH_3$; N-linked triazolyl; and C-linked pyrimidinyl; and $R_6$ is selected from the group consisting of cyclopropyl; $C_1$-$C_6$haloalkoxy, preferably trifluoroethoxy; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —$(CH_2)$-cyclopropyl, or —$(CH_2)$-cyanocyclopropyl; C-linked dihydroisoxazole which can be mono-substituted by cyclopropyl; and C-linked isoxazole which can be mono-substituted by cyclopropyl.

One preferred group of compounds according to this embodiment are compounds of formula (I-C1-1) which are compounds of formula (I-C1), or any of the preferred embodiments of compounds of formula (I-C1), wherein $Q_1$ is independently selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; 1,2,4-triazol-4-yl; pyrimidin-5-yl; and pyrimidin-2-yl; and $R_6$ is selected from the group consisting of cyclopropyl; 2,2,2-trifluoroethoxy; pyrimidin-5-yl; pyrimidin-2-yl; 4-(1-cyanocyclopropyl)phenyl; 3-(1-cyanocyclopropyl)phenyl; 3-chloro-pyrazol-1-yl; 4-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)-pyrazol-4-yl; 3-cyclopropyl-4,5-dihydro-isoxazol-5-yl; and 3-cyclopropyl-isoxazol-5-yl.

One preferred group of compounds according to this embodiment are compounds of formula (I-C1-2) which are compounds of formula (I-C1), or any of the preferred embodiments of compounds of formula (I-C1), wherein $Q_1$ is independently selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; and pyrimidin-2-yl; and $R_6$ is selected from the group consisting of cyclopropyl; 2,2,2-trifluoroethoxy; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)pyrazol-4-yl; 3-cyclopropyl-4,5-dihydro-isoxazol-5-yl; and 3-cyclopropyl-isoxazol-5-yl.

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile, improved physico-chemical properties, or increased biodegradability or environmental profile). In particular, it has been surprisingly found that certain compounds of formula (I) may show an advantageous safety profile with respect to non-target arthropods, in particular pollinators such as honey bees, solitary bees, and bumble bees. Most particularly, *Apis mellifera*.

In another aspect the present invention provides a composition comprising an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I), (I-A1), (I-A2), (I-B1) and (I-C) (above), and, optionally, an auxiliary or diluent.

In a further aspect the present invention provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I), (I-A1), (I-A2), (I-B1) and (I-C) (above) or a composition as defined above.

In a yet further aspect, the present invention provides a method for the protection of plant propagation material from the attack by insects, acarines, nematodes or molluscs, which comprises treating the propagation material or the site, where the propagation material is planted, with a composition as defined above.

The process according to the invention for preparing compounds of formula I is carried out in principle by methods known to those skilled in the art. More specifically, the subgroup of compounds of formula I, wherein X is SO (sulfoxide) and/or $SO_2$ (sulfone), Scheme 1a

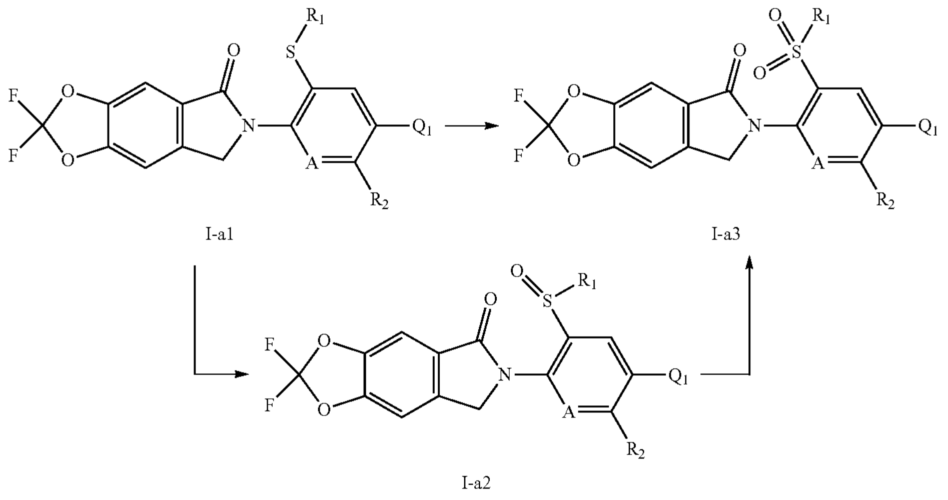

I-a1 I-a3 I-a2

Scheme 1b

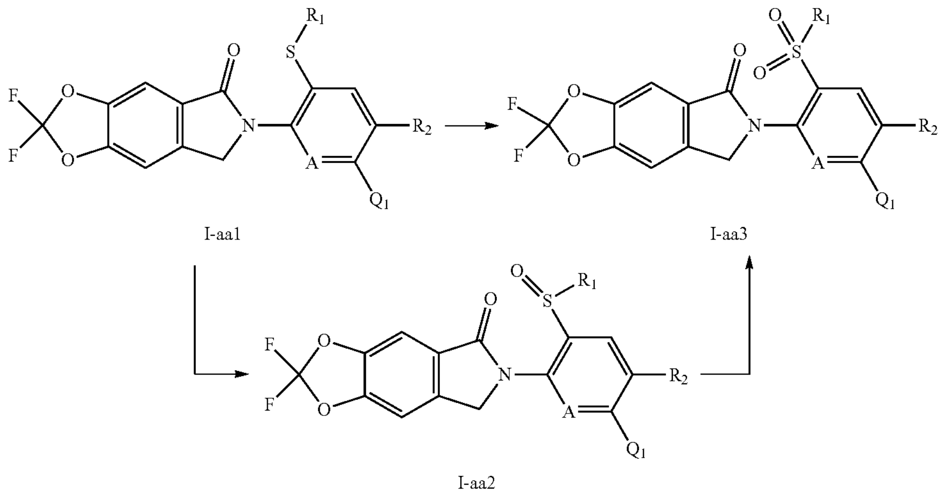

I-aa1 I-aa3 I-aa2 may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants (schemes 1a, 1b and 2). The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928.

Scheme 2
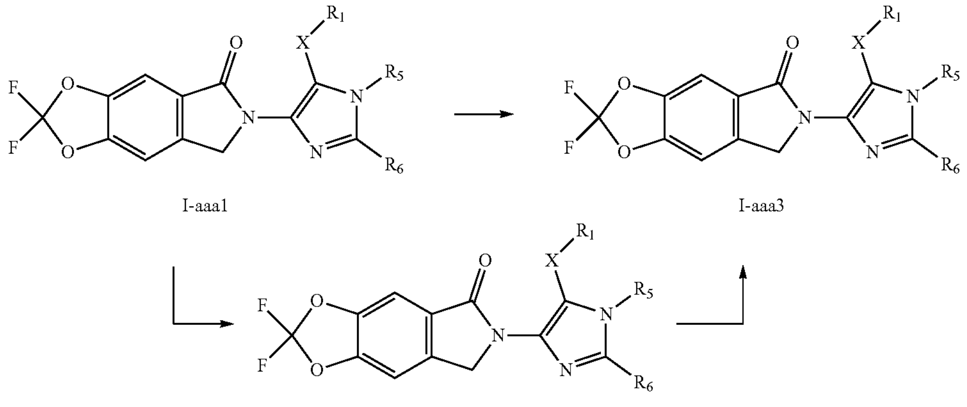
I-aaa1 I-aaa3 I-aaa2
Compounds of formula I, wherein Q is defined as under formula I above, may be prepared (scheme 3)
Scheme 3
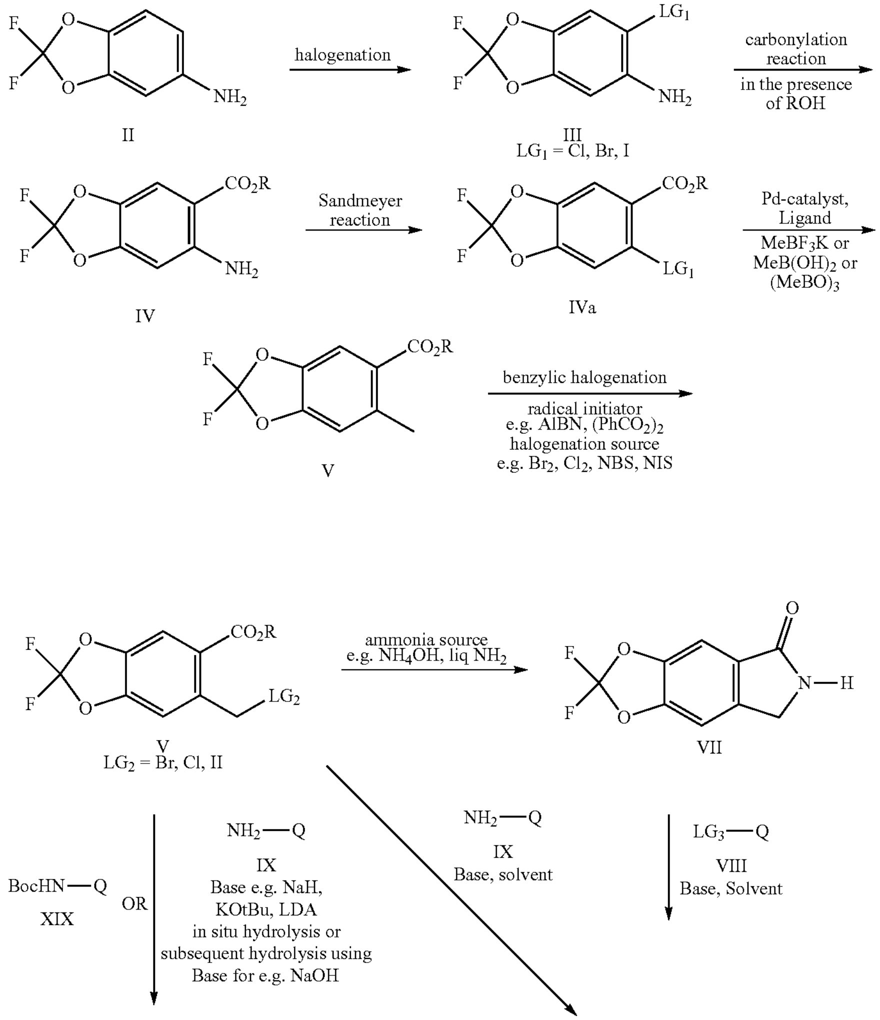
II
III
$LG_1$ = Cl, Br, I
IV
IVa
V
V
$LG_2$ = Br, Cl, II
VII -continued

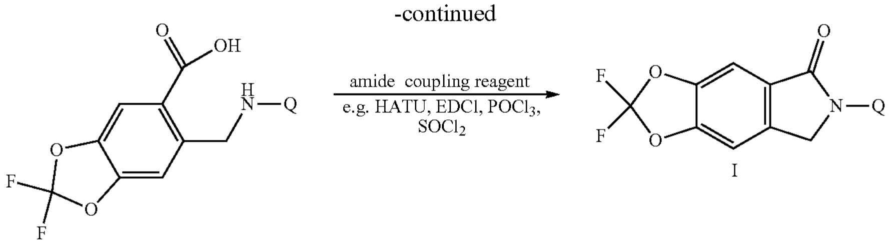

X

I by reacting compounds of formula VII, with compounds of formula VIII, wherein Q is as defined in formula I above and in which $LG_3$ is a halogen (or a pseudo-halogen leaving group, such as a triflate), in the presence of a base, such as sodium carbonate, potassium carbonate or cesium carbonate, or sodium hydride, in an appropriate solvent such as for example tetrahydrofuran, dioxane, N,N-dimethylformamide, N,N-dimethylacetamide or acetonitrile, at temperatures between 0 and 150° C., optionally under microwave irradiation.

Alternatively compounds of formula I, wherein Q is defined as under formula I above, may be prepared by reacting compounds of formula VII, with compounds of formula VIII, wherein Q is as defined in formula I above and in which $LG_3$ is a halogen (or a pseudo-halogen leaving group, such as a triflate), preferably bromo or iodo, in the presence of a base, such as sodium carbonate, potassium carbonate or cesium carbonate, or potassium tert-butoxide, in the presence of a metal catalyst, either copper catalyst for example copper(I) iodide, optionally in the presence of a ligand for example diamine ligands (e.g. N,N'-dimethylethylenediamine or trans-cyclohexyldiamine) or dibenzylideneacetone (dba), or 1,10-phenanthroline, at temperatures between 30-180° C., optionally under microwave irradiation; or palladium catalyst for example palladium(II)acetate, bis(dibenzylideneacetone) palladium(0) ($Pd(dba)_2$) or tris (dibenzylideneacetone) dipalladium(0) ($Pd_2(dba)_3$, optionally in form of a chloroform adduct), or a palladium precatalyst such as for example tert-BuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

The above reaction may be carried out in the presence of solvent such as toluene, dimethylformamide DMF, N-methyl pyrrolidine NMP, dimethyl sulfoxide DMSO, dioxane, tetrahydrofuran THE and are described in literature for example in WO2012031004, WO2009042907 and Synthetic Communications, 41: 67-72, 2011.

Alternatively compounds of formula I, wherein Q is defined as under formula I above, may be prepared (scheme 3) by reacting compounds of formula VI, wherein $LG_2$ is a leaving group for example Br, Cl or I (preferably bromo), and R is $C_1$-$C_6$alkyl, benzyl or a phenyl group, with compounds of formula IX, wherein Q is as defined in formula I above, in the presence of base such as such as sodium carbonate, potassium carbonate or cesium carbonate, or sodium hydride, N,N-diisopropylethylamine or KOtBu, and in the presence of solvent such as ethanol, methanol, dioxane, toluene, acetonitrile, DMF, DMA, DMSO, THF, at temperatures between 0 and 150° C., optionally under microwave irradiation. Such reactions proceed via nucleophilic substitution and subsequent cyclization and are also reported in literature for example in WO2009042907.

Alternatively compounds of formula I, wherein Q is defined as under formula I above, can be prepared (scheme 3) by cyclizing compounds of formula X, wherein Q is as defined in formula I, for example in the presence of phosphorus oxychloride (other amide coupling reagent may also be used, such as thionyl chloride $SOCl_2$, HATU or EDCI), optionally in the presence of a base, such as triethylamine, pyridine or Hunig's base, optionally in the presence of a solvent or diluent, such as toluene or xylene, at temperatures between 0 and 180° C., preferably between 20 and 120° C.

Compounds of formula I, wherein Q is as defined as under formula I above, can also be prepared Scheme 4

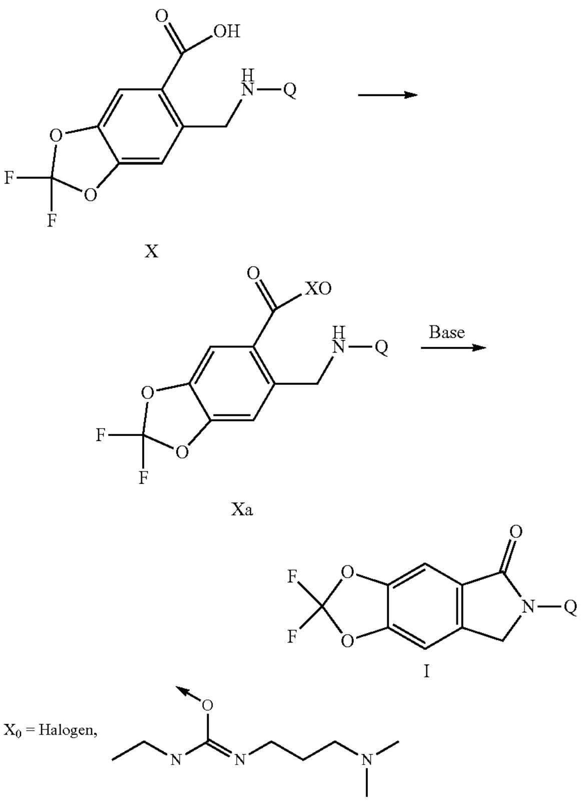

X

Xa

I $X_0$ = Halogen, $X_{01}$

-continued

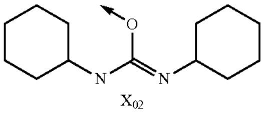

by cyclization of the formula Xa (scheme 4), wherein Q is defined as under formula I above, and in which $X_0$ is halogen, preferably chlorine, or $X_0$ is either $X_{01}$ or $X_{02}$, in the presence of a base, such as triethylamine, N,N-diisopropyl-ethylamine or pyridine, optionally in the presence of a catalyst (such as 4-dimethylaminopyridine DMAP), in an inert solvents such as dichloromethane, tetrahydrofuran, dioxane, N,N-dimethylformamide, N,N-dimethylacetamide, acetonitrile, ethyl acetate or toluene, at temperatures between 0 and 50° C. Certain bases, such as pyridine and triethylamine, may be employed successfully as both base and solvent.

Compounds of formula Xa, wherein Q is defined as under formula I above, and in which $X_0$ is halogen, preferably chlorine, or $X_0$ is either $X_{01}$ or $X_{02}$, can be prepared by activation of compound of formula X, wherein Q is defined as under formula I above, by methods known to those skilled in the art and described in, for example, Tetrahedron, 2005, 61 (46), 10827-10852. Preferred is the formation of an activated species Xa, wherein Q is defined as under formula I above and in which $X_0$ is halogen, preferably chlorine. For example, compounds Xa where $X_0$ is halogen, preferably chlorine, are formed by treatment of X with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THE at temperatures between 20 to 100° C., preferably 25° C. Alternatively, treatment of compounds of formula X with, for example, 1-ethyl-3-(3-dimethylamino-propyl)carbodiimide EDC or dicyclohexyl carbodiimide DCC will generate an activated species Xa, wherein $X_0$ is $X_{01}$ or $X_{02}$ respectively, in an inert solvent, such as pyridine or tetrahydrofuran THF, optionally in the presence of a base, such as triethylamine, at temperatures between 50-180° C.

Compounds of formula VII can be prepared by reacting compounds of formula VI, wherein $LG_2$ is a leaving group for example Br, Cl or I (preferably bromo) and R is $C_1$-$C_6$alkyl, benzyl or a phenyl group, with ammonia or surrogates of ammonia, for example $NH_4OH$, in the presence of a solvent such as ethanol, methanol, dioxane, toluene, DMF, DMA, DMSO, THE at temperatures between 0 and 150° C., optionally under microwave irradiation.

Compounds of formula X, wherein Q is defined as under formula I above, can be prepared (scheme 3) by nucleophilic substitution reaction of compound of formula VI, wherein $LG_2$ is a leaving group for example Br, Cl or I (preferably bromo) and R is $C_1$-$C_6$alkyl, benzyl or a phenyl group, with amino compound of formula IX, wherein Q is as defined in formula I above, under conditions described above, followed by in situ hydrolysis of the formed intermediate ester of formula XVII (see also scheme 8), wherein Q is defined as under formula I above, and in which R is $C_1$-$C_6$alkyl, benzyl or a phenyl group.

(XVII)

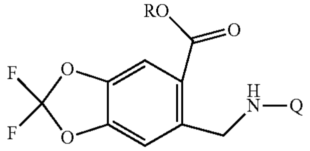

The in situ generated unhydrolyzed ester compound of formula XVII may be isolated and can also be converted via saponification reaction in the presence of suitable base for example sodium hydroxide NaOH, lithium hydroxide LiOH, or barium hydroxide $Ba(OH)_2$, in the presence of a solvent such as ethanol, methanol, dioxane, tetrahydrofuran or water (or mixtures thereof), to form the carboxylic acid of formula X. Alternatively, Krapcho-type conditions (e.g. heating the substrate XVII in the presence of sodium or lithium chloride in N-methyl pyrrolidone or aqueous dimethylsulfoxide DMSO, optionally under microwave irradiation) can also be used to convert compounds of formula XVII into compounds of formula X. The direct conversion of compound of formula VI to compound of formula X can be carried out in the presence of a base such as sodium hydride, KOtBu, butyllithium, or lithium diisopropylamide amongst others, and in the presence of a solvent such as dioxane, DMF, DMA, DMSO, or THF, at temperatures between −30 and 150° C.

The above reaction for the preparation of compounds of formula X can also be carried out by reacting compounds of formula VI, with compounds of formula IXa, wherein Q is as defined in formula I above, and PG is an amino protecting group, for example tert-butyloxycarbonyl (BOC) under similar conditions as described above (as for the preparation of compounds of formula X by reacting compounds of formula VI and compounds of formula IX), followed by deprotection of the amino protecting group PG.

(IXa)

The deprotection of the amino protecting groups are well known to those skilled in the art, for example BOC protecting groups can be removed in the presence of acids such as hydrochloric acid, or trifluoroacetic acid, optionally in the presence of an inert solvent, such as dichloromethane, tetrahydrofuran, dioxane or benzotrifluoride, at temperatures between 0 and 70° C. This process of forming compounds of formula X (and I) from compounds of formula VI and IXa is detailed in scheme 3a and reflecting the particular situation wherein the group PG of IXa is tert-butyloxycarbonyl (BOC), defining compounds of formula XIX, wherein Q is as defined in formula I above.

Scheme 3a (substituent definitions mentioned previously remain valid):

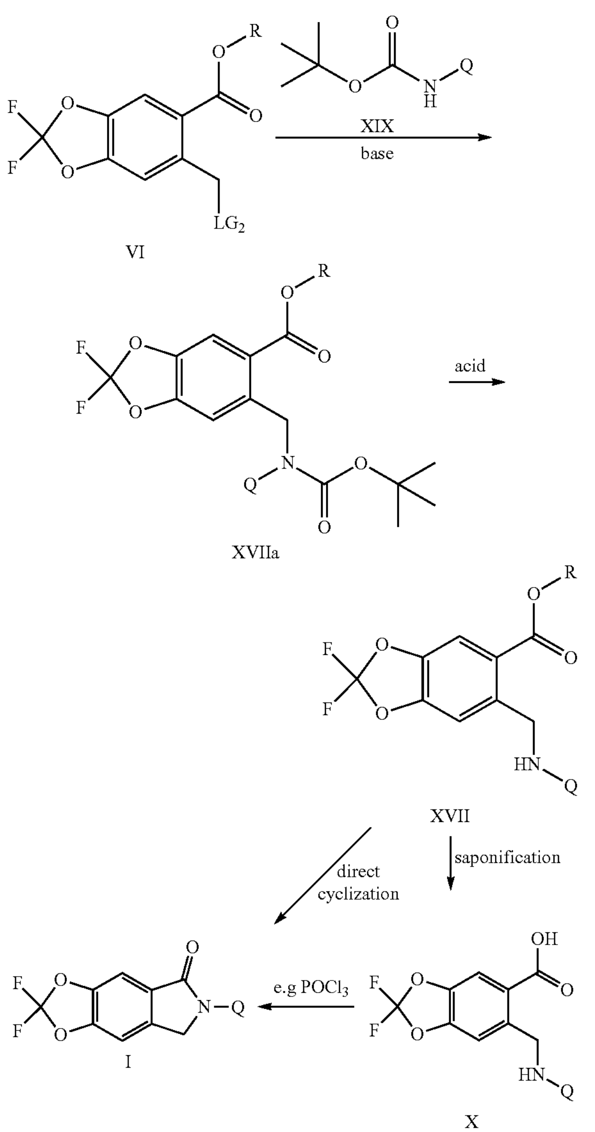

Compounds of formula VI and compounds of formula XIX react to compounds of formula XVIIa, in the presence of a base, such as sodium carbonate, potassium carbonate or cesium carbonate, or sodium hydride, or N,N-diisopropylethylamine or potassium tert-butoxide KOtBu, in the presence of a solvent such as ethanol, methanol, dioxane, toluene, acetonitrile, DMF, N,N-dimethylacetamide DMA, DMSO, or THF, at temperatures between 0 and 150° C., optionally under microwave irradiation. tert-Butyloxycarbonyl (BOC) group removal in compounds of formula XVIIa, mediated by acids, such as hydrochloric acid, or trifluoroacetic acid, optionally in the presence of an inert solvent, such as dichloromethane, tetrahydrofuran, dioxane or benzotrifluoride, at temperatures between 0 and 70° C., generates compounds of formula XVII. Saponification of compounds of formula XVII in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), forms the carboxylic acids of formula X (alternatively, Krapcho-type conditions as described above may be used). Cyclization of compounds of formula X to compounds of formula I is achieved, for example, in the presence of phosphorus oxychloride (other amide coupling reagent may also be used, such as thionyl chloride $SOCl_2$, HATU or EDCI), optionally in the presence of a base, such as triethylamine, pyridine or Hunig's base, optionally in the presence of a solvent or diluent, such as toluene or xylene, at temperatures between 0 and 180° C., preferably between 20 and 120° C. Alternatively, a direct cyclization of compounds of formula XVII into compounds of formula I may be achieved under conditions mentioned below in scheme 8.

Compounds of formula VI, wherein $LG_2$ is a leaving group for example Br, Cl or I (preferably bromo) and R is $C_1$-$C_6$alkyl, benzyl or a phenyl group, are either known or may be prepared by methods known to a person skilled in the art.

For example, compounds of formula VI, wherein $LG_2$ is a leaving group, for example Br, Cl or I (preferably bromo), and R is $C_1$-$C_6$alkyl, benzyl or a phenyl group, can be prepared by radical induced benzylic halogenation of compounds of formula V, wherein R is $C_1$-$C_6$alkyl, benzyl or a phenyl group. Such reactions are well known to those skilled in the art and may be carried out in the presence of electrophilic halogenating reagents, such as $Br_2$, NBS, $Cl_2$, or NIS amongst others, in the presence of radical initiator for example AIBN (azobisisobutyronitrile) or benzoyl peroxide, or under photochemical conditions, at temperatures ranging from 20° C. to the boiling point of the reagent mixture, and in the presence of a solvent such as toluene, xylene, acetonitrile, hexane, dichloroethane, or carbon tetrachloride. Such reactions are known by the name of Wohl-Ziegler bromination and are reported in literature for example in *Synthesis,* 2015, 47, 1280-1290 and *J. Am. Chem. Soc.,* 1963, 85 (3), pp 354-355.

Compounds of formula V, wherein R is $C_1$-$C_6$alkyl, benzyl or a phenyl group, may be prepared (scheme 3) by a Suzuki reaction, which involves for example, reacting compounds of formula IVa, wherein $LG_1$ is a halogen such as Br, Cl, or I (preferably Cl), and R is $C_1$-$C_6$alkyl, benzyl or a phenyl group, with trimethylboroxine or potassium methyltrifluoroborate amongst other methyl boronic acid equivalent. The reaction may be catalyzed by a palladium based catalyst, for example tetrakis(triphenyl-phosphine)palladium(0), (1,1'bis(diphenylphosphino)ferrocene)dichloropalladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethyl-formamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 576, 1999, 147-168.

Alternatively compounds of formula V, wherein R is $C_1$-$C_6$alkyl, benzyl or a phenyl group, can be prepared following scheme 3b.

Scheme 3b

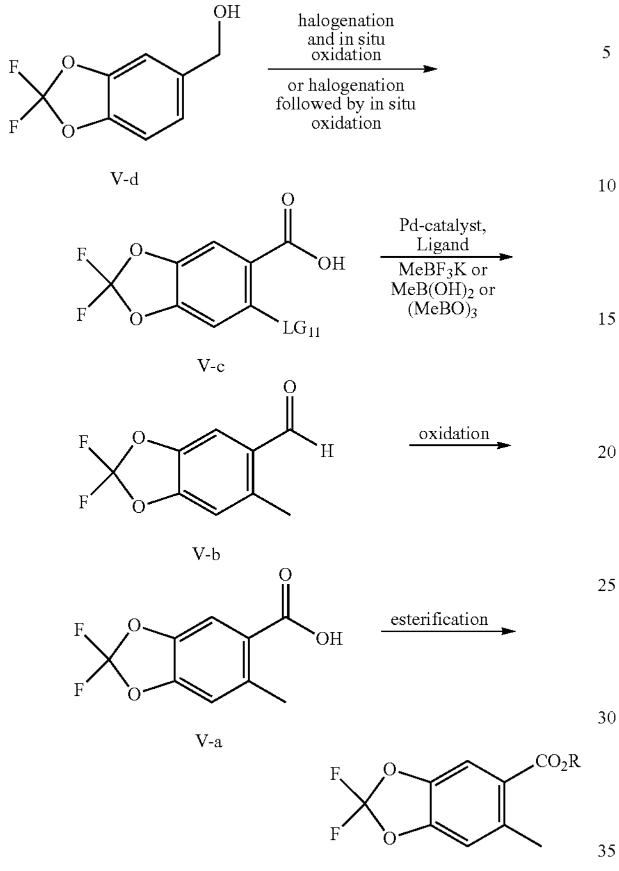

V-d, V-c, V-b, V-a, V

In scheme 3b compounds of formula V, wherein R is $C_1$-$C_6$alkyl, benzyl or a phenyl group, can be prepared from compounds of formula V-a via esterification reactions, which involve reacting compounds of formula V-a with alcohols R—OH, wherein R is $C_1$-$C_6$alkyl, benzyl or a phenyl group, in the presence of an acid catalyst, for example sulfuric acid, or a Lewis acid, for example $Sc(OTf)_3$ or $FeCl_3$. Such reactions are well known to those skilled in the state of art, known by the name of Fischer esterification reaction, and are reported in literature for example in *J. Org. Chem.,* 2006, 71, 3332-3334, *Chem. Commun.,* 1997, 351-352 and *Synthesis,* 2008, 3407-3410. Such esterification reaction can also be carried out by reacting compounds of formula V-a with $TMSCHN_2$ to form compounds of formula V, wherein R is methyl, and which are reported in *Angew. Chem. Int. Ed.* 2007, 46, 7075. Compounds of formula V-a can be prepared by the oxidation reaction of compounds of formula V-b. Such reactions are well known to person skilled in the art. Examples of the reagent which facilitates such transformation includes Oxone, $KMnO_4$, $NaClO_2$ (known by the name of Pinnick oxidation), $AgNO_3$ in the presence of metal hydroxide or $Ag_2O$ (known by the name of Tollen's reagent). Such reactions are known in the literature and described for example in Acta Chem. Scand. 1973, 27: 888-890; Tetrahedron 1981, 37 (11): 2091-2096; Ber. Deut. Chem. Gessel., 15 (1882), pp. 1635-1639; Org. Synth. 1953, 33, 94. Compounds of formula V-b can be prepared from compounds of formula V-c, wherein $LG_{11}$ is a halogen such as Br, Cl, or I (preferably Cl), via an analogous procedure as described in scheme 3 for the conversion of compounds of formula IVa to compounds of formula V. Compounds of formula V-c, wherein $LG_{11}$ is a halogen such as Br, Cl, or I (preferably Cl), can be prepared from compounds of formula V-d, via a halogenation and an in situ oxidation reaction using halogenating reagents such as iodine, bromine, chlorine, N-chlorosuccinimide, or N-bromosuccinimide amongst others. Alternatively, the halogenation can be performed and in a subsequent step the oxidation reaction can be carried out using oxidating reagent to form the compounds of formula V-c from compounds of formula V-d in two steps. Compound of formula V-d is known in the literature with CAS registry number 72768-97-9.

Compounds of formula IVa, wherein, $LG_1$ is a halogen Br, Cl, or I (preferably Cl), and R is $C_1$-$C_6$alkyl, benzyl or a phenyl group can be prepared (scheme 3) by reacting compounds of formula IV, wherein R is $C_1$-$C_6$alkyl, benzyl or phenyl, with a nitrite, such as tert-butyl nitrite t-BuONO, isoamyl nitrite, or sodium nitrite, in the presence of a hydrohalic acid H-$LG_1$ and a copper salt Cu-$LG_1$, wherein $LG_1$ is halogen, for example Br, Cl or I (preferably Cl), under Sandmeyer-type reaction conditions. This transformation is preferably performed in an inert solvent, such as acetonitrile or a halogenated solvent like 1,2-dichloroethane, or water at temperatures between 0-150° C., preferably at temperatures ranging from room temperature to the boiling point of the reaction mixture. Compounds of formula IV, wherein R is $C_1$-$C_6$alkyl, benzyl or phenyl, can be prepared from compounds of formula III, wherein $LG_1$ is halogen, preferably Br, Cl or I, by methods found in, for example, WO 2016/020286, involving a carbonylation reaction, in which compounds of formula III are reacted with carbon monoxide CO (usually under pressure), in presence of metal catalyst such as a palladium catalyst (for example: palladium (II) acetate), in an alcohol ROH solvent (optionally in presence of a co-solvent), wherein R is $C_1$-$C_6$alkyl, benzyl or phenyl, and optionally in presence of a phosphine ligand, and optionally in presence of a base, at temperatures between 0-180° C. Compounds of formula III, wherein $LG_1$ is halogen, preferably Br, Cl or I, can be prepared by a halogenation reaction, which involves for example, reacting compounds of formula II, with halogenating reagents such as N-chlorosuccinimide (NCS), N-bromo-succinimide (NBS) or N-iodosuccinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 20-200° C., preferably room temperature to 100° C.

The compounds of formula VI (VI)

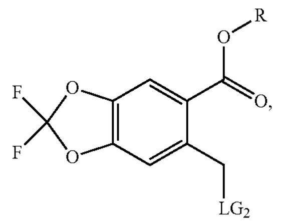

wherein $LG_2$ is a leaving group for example Br, Cl or I, and R is $C_1$-$C_6$alkyl, benzyl or phenyl are novel, especially developed for the preparation of the compounds of formula I according to the invention and therefore represent a further object of the invention. The preferences and preferred embodiments of the substituents of the compounds of formula I are also valid for the compounds of formula VI. Preferably, $LG_2$ is bromo or chloro; even more preferably $LG_2$ is bromo. Preferably R is $C_1$-$C_6$alkyl; even more preferably R is methyl or ethyl.

Alternatively compounds of formula I, wherein Q is defined as under formula I above, can be prepared by performing an amidation reaction on compounds of formula X, wherein Q is defined as under formula I above, following scheme 5.

-continued

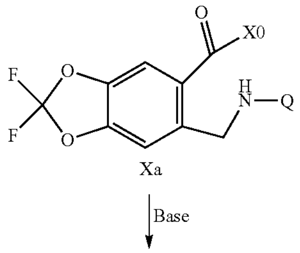

Xa

Scheme 5

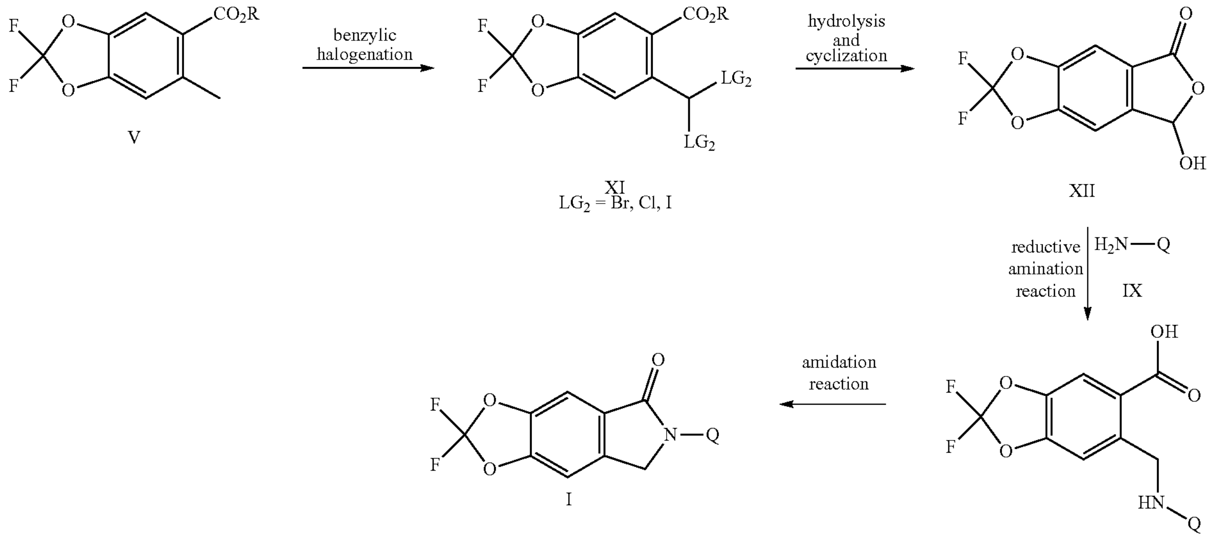

V

XI
$LG_2$ = Br, Cl, I

XII

X

I

The reaction details for the transformation of compounds of formula X into compounds of formula I (amidation reaction) are illustrated in scheme 6, and follow methods and conditions already described in schemes 3 and 4 above (path compounds of formula X to compounds of formula Xa to compounds of formula I).

Scheme 6

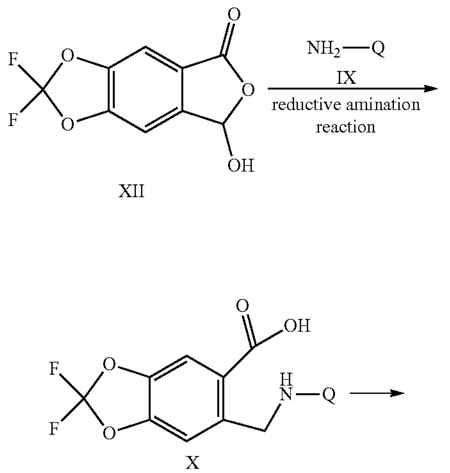

XII

X

-continued

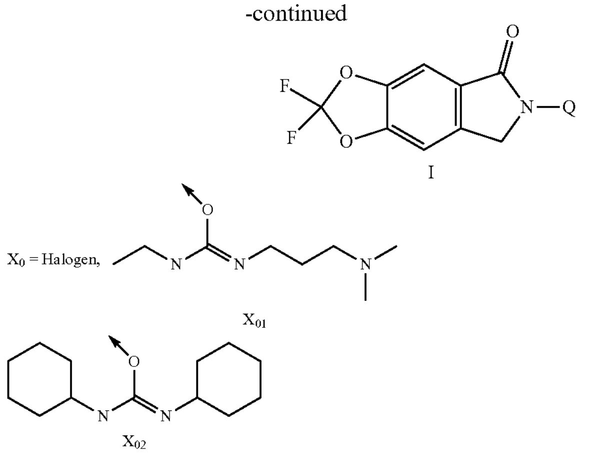

I $X_{01}$ $X_{02}$

Compounds of formula X, wherein Q is defined as under formula I above, can be prepared by reacting compounds of formula XII, with compounds of formula IX, wherein Q is as defined in formula I above, under reductive amination conditions (scheme 6). The reaction can be carried out in the presence of a reducing agent, for example sodium cyanoborohydride or sodium triacetoxyborohydride, amongst others, optionally in the presence of acid such as trifluoroacetic acid, formic acid or acetic acid and the like, and at temperatures ranging from 0° C. to the boiling point of the recation mixture. The reaction can be carried out in the presence of inert solvents, such as ethanol, methanol, dioxane or tetrahydrofuran. Such reactions involving a multi-step conversion from compounds of formula XII to compounds of formula I have been described in literature, for example, in Bioorganic & Medicinal Chemistry Letters 26 (2016) 5947-5950.

Compounds of formula XII can be prepared (scheme 5) from compound of formula XI, wherein $LG_2$ is chloro, bromo or iodo (preferably bromo), and R is $C_1$-$C_6$alkyl, benzyl or a phenyl group, by a hydrolysis and subsequent intramolecular cyclization reaction. The reaction can be carried out either using metal hydroxide under basic conditions, for example using aqueous sodium hydroxide, in the presence of a solvent such as dioxane, tetrahydrofuran or water, and at temperature ranging from 20 to 150° C. as reported in Synlett 1992, (6), 531-533, or under aqueous acidic conditions, for example using acetic acid, hydrochloric acid or sulfuric acid, in the presence of a solvent such as water, dioxane, or halogenated solvents such as dichloroethane as reported in Tetrahedron 62 (2006) 9589-9602.

Compounds of formula XI, wherein $LG_2$ is chloro, bromo or iodo (preferably bromo), and R is $C_1$-$C_6$alkyl, benzyl or a phenyl group, can be prepared from compounds of formula V, wherein R is $C_1$-$C_6$alkyl, benzyl or a phenyl group, by methods similar to those described in scheme 3 for the conversion of compound of formula V to compound of formula VI. Preferably in the presence of an excess of the electrophilic halogenating reagent, more preferably at least around two equivalents thereof.

Alternatively compounds of formula I, wherein Q is defined as under formula I above, may be prepared from compounds of formula XV, wherein Q is defined as under formula I above, via selective reduction of the carbonyl functional group (scheme 7).

Scheme 7

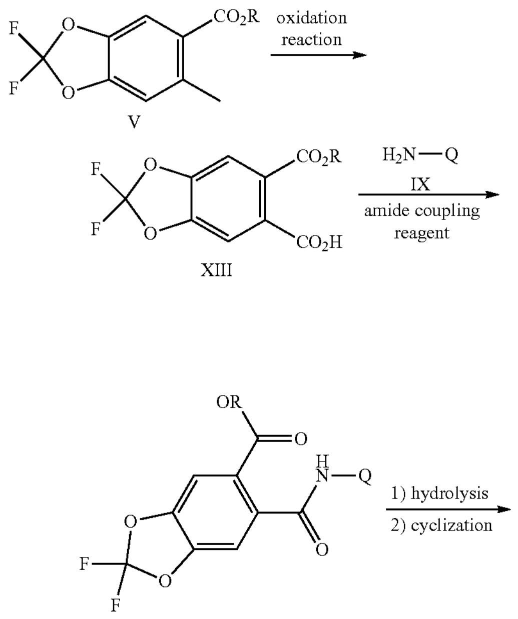

V

XIII

XIV

-continued

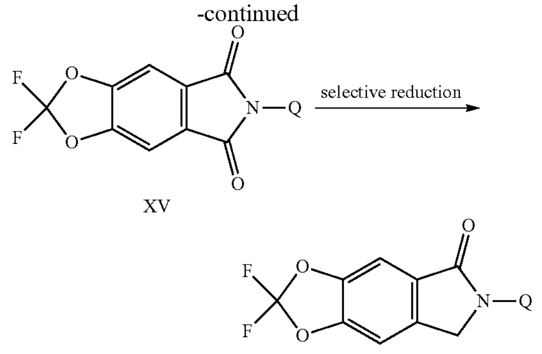

XV

I

The reaction can be carried out in the presence of reducing agent for example $NaBH_4$, $LiAlH_4$, palladium on carbon in the presence of hydrogen or a combination of two reducing agent for example $NaBH_4$ followed by triethylsilane. Such reactions have been described for example in US20100160303A1.

Compounds of formula XV, wherein Q is defined as under formula I above, may be prepared from compounds of formula XIV, wherein Q is defined as under formula I above, and R is $C_1$-$C_6$alkyl, benzyl or phenyl, by a hydrolysis reaction and subsequent cyclization reaction as described in scheme 4 for the conversion of compounds of formula X to compounds of formula I.

Compounds of formula XIV, wherein Q is defined as under formula I above, and R is $C_1$-$C_6$alkyl, benzyl or phenyl, may be prepared by reacting compounds of formula XIII, wherein R is $C_1$-$C_6$alkyl, benzyl or phenyl, with compounds of formula IX, wherein Q is as defined in formula I above, by an amidation reaction already described in scheme 4.

Compounds of formula XIII, wherein R is $C_1$-$C_6$alkyl, benzyl or phenyl, may be prepared by benzylic oxidation of compounds of formula V, wherein R is $C_1$-$C_6$alkyl, benzyl or phenyl. The reaction can be carried out in the presence of oxidative reagents such as $KMNO_4$, $nBu_4MnO_4$, $K_2S_2O_8$ in the presence of oxygen, or under photochemical conditions in the presence of oxygen and at temperature ranging from 20° C. to the boiling point of solvent. The reaction is carried out in the presence of inert solvent such as acetonitrile, ethyl acetate, DMSO, dichloroethane. Such reactions are known in the literature for example in *Synthesis,* 2017, 49, 4007-4016, *Synthesis,* 2006, 1757-1759 and IOSR Journal of Applied Chemistry, 2014, 7, 16-27.

Alternatively, compounds of formula I, wherein Q is as defined in formula I above, can be prepared by cyclization reaction of compounds of formula XVII, wherein Q is as defined in formula I above and R is $C_1$-$C_6$alkyl, benzyl or phenyl (scheme 8).

Scheme 8

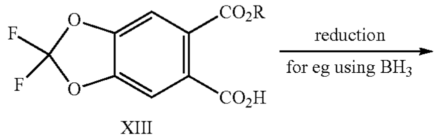

XIII

-continued

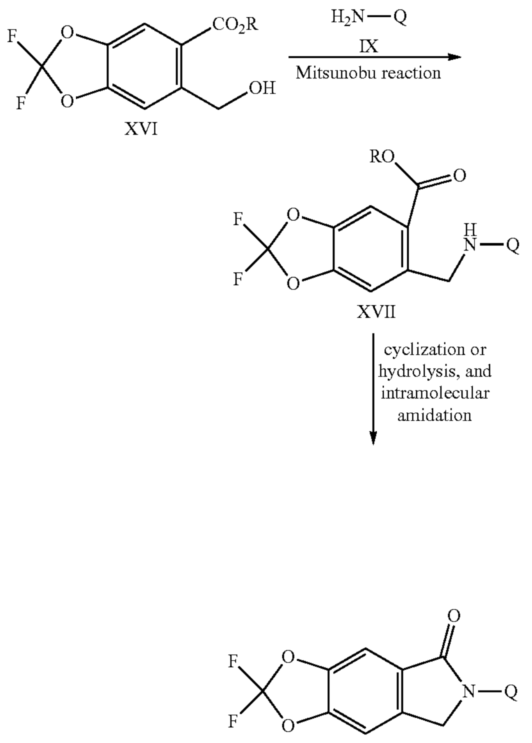

XVI

XVII

I

Such a reaction can be carried out in the presence of a base, such as potassium tert-butoxide, lithium diisopropylamide, sodium hydride, amongst others, at temperatures ranging from −20° C. to the boiling point of the reaction mixture, and in the presence of inert solvent such as tetrahydrofuran, dioxane, DMA, DMSO or DMF. Such reactions are reported for example in Synlett 2006(4): 591-594.

Compounds of formula XVII, wherein Q is as defined in formula I above, and R is $C_1$-$C_6$alkyl, benzyl or phenyl, may be prepared by reacting compounds of formula XVI, wherein R is $C_1$-$C_6$alkyl, benzyl or phenyl, with compounds of formula IX, wherein Q is as defined in formula I above, under Mitsunobu conditions. Such reactions are well known to those skilled in the state of art and can be carried out in the presence of phosphine reagent, such as triphenylphosphine, tributylphosphine, or polymer supported triphenyl phosphine amongst others, in the presence of an azodicarboxylate reagent such as diethyl azodicarboxylate, diisopropyl azodicarboxylate, at temperature ranging from 0° C. and 100° C., and in the presence of inert solvent such as acetonitrile, dichloromethane, tetrahydrofuran, or toluene. Such reactions are reported for example in Synthesis, 1981 (1), 1-28.

Compounds of formula XVI, wherein R is $C_1$-$C_6$alkyl, benzyl or phenyl, may be prepared by reacting compounds of formula XIII, wherein R is $C_1$-$C_6$alkyl, benzyl or phenyl, with reducing agents such as, for example, metal hydrides like lithium aluminumhydride, DIBAL-H, or boranes (such as diborane, borane tetrahydrofuran complex amongst others), at temperatures ranging from 0° C. and 150° C., and in the presence of an inert solvent such as tetrahydrofuran, or dioxane. Such reactions have been reported in Tetrahedron Letters, 1982, 23, 2475-2478.

Alternatively compounds of formula I, wherein Q is as defined in formula I above, Scheme 8a

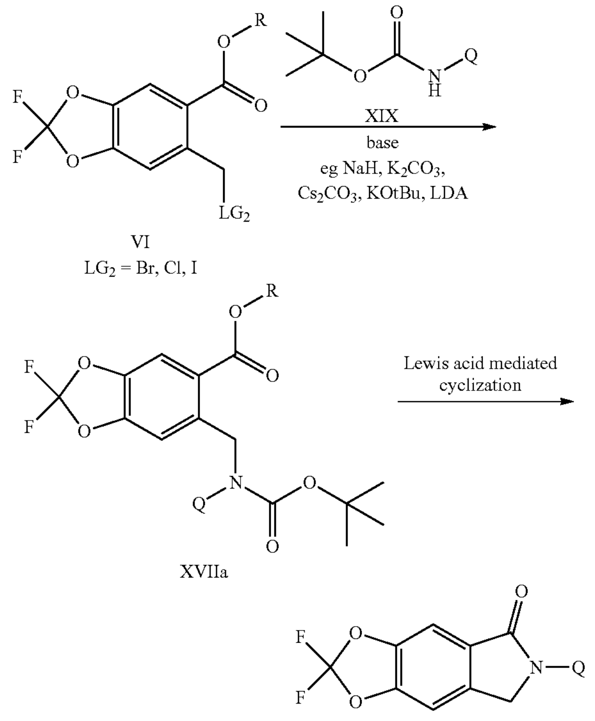

VI

XVIIa

I may be prepared (scheme 8a) from compounds of formula XVIIa, wherein Q is as defined in formula I above, and R is $C_1$-$C_6$alkyl, benzyl or phenyl, by a thermal mediated BOC-deprotection and subsequent Lewis mediated intramolecular cyclization. Such reactions can be carried out in the presence of Lewis acids such as bis(trimethylaluminum)-1,4-diazabicyclo[2.2.2]octane adduct, also known as DABAL-$Me_3$, or lanthanum triflate amongst others. Such reaction can be carried out in the presence of solvents such as toluene, xylene, or N-methyl-2-pyrrolidone amongst others, at temperatures between 25° C. to 250° C., optionally under microwave conditions. The formation of amide bonds using such procedures are reported, for example, in Tetrahedron Letters (2006), 47(32), 5767-5769.

The compounds of formula XVII-a (XVII-a)

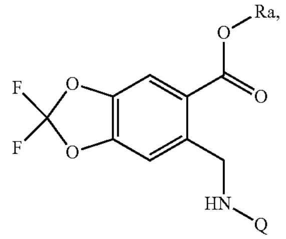

wherein

Q is as defined under formula I above, and Ra is hydrogen, $C_1$-$C_6$alkyl, benzyl or phenyl are novel, especially developed for the preparation of the compounds of formula I according to the invention and therefore represent a further object of the invention. The preferences and preferred embodiments of the substituents of the compounds of formula I are also valid for the compounds of formula XVII-a. Preferably, Ra is hydrogen or $C_1$-$C_6$alkyl; even more preferably, Ra is hydrogen, methyl or ethyl; most preferably Ra is hydrogen.

Compounds of formula IX, wherein Q is as defined in formula I above, can be prepared by performing a deprotection reaction (BOC group removal) on compounds of formula XIX, wherein Q is as defined in formula I above (scheme 9).

Scheme 9

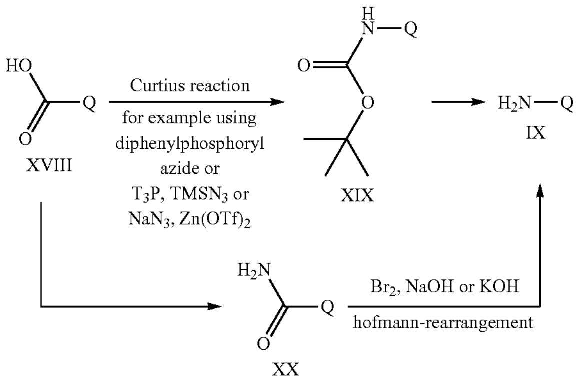

The reaction can be carried out in the presence of acids, such as trifluoroacetic acid, hydrochloric acid or sulfuric acid amongst others, under conditions already described above.

Compounds of formula XIX, wherein Q is as defined in formula I above, can be prepared by the reaction of compounds of formula XVIII, wherein Q is as defined in formula I above, with an organo-azide in the presence of a suitable base and tert-butanol t-BuOH, and in the presence of a coupling agent, optionally in the presence of a Lewis acid, and in the presence of an inert solvent, at temperatures between 50° C. and the boiling point of the reaction mixture. The reaction can be carried out in the presence of a coupling agent, such as $T_3P$, or via activation of the carboxylic acid with $SOCl_2$ or oxalyl chloride, or other coupling agents as described in scheme 4 for the conversion of compounds of formula X into compounds of formula Xa. Examples of organo-azide include $TMSN_3$, sodium azide, or tosyl azide, and a suitable solvent may be toluene, xylene, THE or acetonitrile. Example of a suitable Lewis acid may include $Zn(OTf_2$, $Sc(OTf_2$, or $Cu(OTf_2$ amongst others.

Compounds of formula XIX can also be prepared by reacting compounds of formula XVIII with diphenylphosphorylazide, in the presence of an organic base, such as triethylamine, or diisopropylethylamine amongst others, in the presence of tert-butanol t-BuOH, in an inert solvent, for example a halogenated solvent, such as dichloromethane or dichloroethane, or cyclic ethers such as tetrahydrofuran amongst others, and at temperatures ranging from 50° C. to the boiling point of the reaction mixture. Such reactions of converting carboxylic acids to BOC protected amines are well known to those skilled in the state of art by the name of Curtius reaction and are reported, for example, in *Org. Lett.*, 2005, 7, 4107-4110; Journal of Medicinal Chemistry, 49(12), 3614-3627; 2006, *J. Am. Chem. Soc.*, 1972, 94 (17), pp 6203-6205.

Compounds of formula XIX, wherein Q is as defined in formula I above, may also be prepared from compounds of formula XX, wherein Q is as defined in formula I above, by a Hofmann-rearrangement reaction. The reaction can be carried out in the presence of a base, for example metal hydroxides, such as aqueous sodium hydroxide or potassium hydroxide, or organic bases such as DBU (1,8-diazabicyclo (5.4.0)undec-7-ene), in the presence of electrophilic halogenating reagents, such as chlorine, bromine or N-bromosuccinimide, and at temperatures ranging from 20° C. to the boiling point of the reaction mixture. Such reactions are known by the name of Hofmann-rearrangement and are reported in literature, for example, in Chem. Ber. 1881, 14, 2725.

Compounds of formula XX, wherein Q is as defined in formula I above, can be prepared by the reaction of compounds of formula XVIII, wherein Q is as defined in formula I above, with ammonia $NH_3$, or other ammonia surrogates, for example $NH_4OH$, in the presence of a carboxylic acid activating agent as described in scheme 4.

Compounds of formula XVIII, wherein Q is a radical selected from the group consisting of formula Qa and Qb, in which A, $Q_1$, $R_2$, X and $R_1$ are as defined in formula I above, are either known, commercially available or may be prepared by those skilled in the art. In particular the following subgroup compounds of formula XVIII are known in the literature and are described below: 5-(1-cyano-1-methyl-ethoxy)-3-ethylsulfanyl-pyridine-2-carboxylic acid (CAS 2417036-66-7, described in WO2020141136); 5-(1-cyano-1-methyl-ethyl)-3-ethylsulfanyl-pyridine-2-carboxylic acid (CAS 2225113-81-3, described in WO2018077565); 5-(1-cyano-1-methyl-ethyl)-3-ethylsulfonyl-pyridine-2-carboxylic acid (CAS 2243224-65-7, described in WO2018153778); 5-(1-cyanocyclopropyl)-3-ethylsulfanyl-pyridine-2-carboxylic acid (CAS 2225113-77-7, described in WO2019234158); 5-(1-cyanocyclopropyl)-3-ethylsulfonyl-pyridine-2-carboxylic acid (CAS 1879106-82-7, described in WO2016087265); 3-ethylsulfanyl-5-(trifluoromethyl)pyridine-2-carboxylic acid (CAS 1421952-02-4, described in WO2016107831); 3-ethylsulfonyl-5-(trifluoromethyl)pyridine-2-carboxylic acid (CAS 1421953-19-6, described in CN110606828); 3-ethylsulfonyl-6-(1,2,4-triazol-1-yl)pyridine-2-carboxylic acid (CAS 2016034-28-7, described in WO2019008115); 5-[acetyl(methyl)amino]-3-ethylsulfonyl-pyridine-2-carboxylic acid (CAS 2632239-16-6, described in WO2021053110); 6-cyclopropyl-3-ethylsulfanyl-pyridine-2-carboxylic acid (CAS 1970134-21-4, described in WO2016116338); 3-ethylsulfonyl-6-pyrimidin-2-yl-pyridine-2-carboxylic acid (CAS 1970134-19-0, described in WO2016116338).

Compounds of formula XVIII, wherein Q is the radical of formula Qc, in which X, $R_5$, $R_6$ and $R_1$ are as defined in formula I above, may be defined as compounds of the formula XVIII-c.

(XVIII-c)

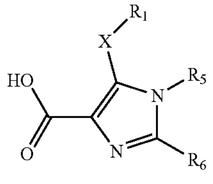

Few compounds of formula XVII-c wherein X is S (sulfide) are known in the literature (CAS 2234901-66-5, CAS 2236074-76-1), and are described in WO2018130443 and WO2018130437.

The subgroup of compounds of formula IX, wherein Q is defined as Qa, in which X is $SO_2$, A is N, and $R_1$, $R_2$ and $Q_1$ are as defined in formula I, can be defined as compounds of formula IX-1 (scheme 9a).

Scheme 9a

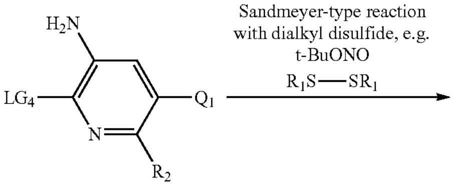

IX-1c

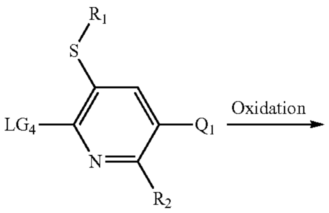

IX-1b

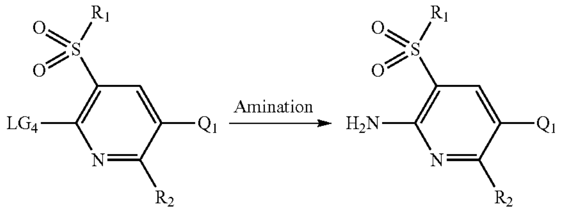

IX-1a IX-1

Compounds of formula IX-1 can be prepared by an amination reaction, which involves for example, reacting compounds of formula IX-1a, wherein $R_1$, $R_2$ and $Q_1$ are as defined in formula I, and $LG_4$ is halogen, preferably F, Br or Cl, with ammonia, or a salt thereof (such as a hydrohalide salt, preferably a hydrochloride or a hydrobromide salt, or any other equivalent salt). The source of nitrogen may be ammonia $NH_3$ itself or an ammonia equivalent such as for example ammonium hydroxide $NH_4OH$, ammonium chloride $NH_4Cl$, ammonium acetate $NH_4OAc$, ammonium carbonate $(NH_4)_2CO_3$, and other $NH_3$ surrogates. This transformation is preferably performed in suitable solvents (or diluents) such as alcohols, amides, esters, ethers, nitriles and water, particularly preferred are methanol, ethanol, 2,2,2-trifluoroethanol, propanol, iso-propanol, N,N-dimethylformamide, N,N-dimethylacetamide, dioxane, tetrahydrofuran, dimethoxyethane, acetonitrile, ethyl acetate, water or mixtures thereof, optionally in presence of a base, at temperatures between 0-150° C., preferably at temperatures ranging from room temperature to the boiling point of the reaction mixture, optionally under microwave irradiation.

Compounds of formula IX-1a, wherein $R_1$, $R_2$ and $Q_1$ are as defined in formula I, and $LG_4$ is halogen, preferably F, Br or Cl, can be prepared by oxidizing compounds of formula IX-1b, wherein $R_1$, $R_2$ and $Q_1$ are as defined in formula I, and $LG_4$ is halogen, preferably F, Br or Cl, under conditions already described above.

Compounds of formula IX-1b, wherein $R_1$, $R_2$ and $Q_1$ are as defined in formula I, and $LG_4$ is halogen, preferably F, Br or Cl, can be prepared by reacting compounds of formula IX-1c, wherein $R_2$ and $Q_1$ are as defined in formula I, and $LG_4$ is halogen, preferably F, Br or Cl, with a nitrite, such as tert-butyl nitrite t-BuONO, isoamyl nitrite, or sodium nitrite in presence of a hydrohalic acid, and a disulfide $R_1S$—$SR_1$ or alternatively a thiol $R_1SH$, wherein $R_1$ is as defined in formula I above, under Sandmeyer-type reaction conditions. This transformation is preferably performed in an inert solvent, such as acetonitrile or a halogenated solvent like 1,2-dichloroethane, at temperatures between 0-150° C., preferably at temperatures ranging from room temperature to the boiling point of the reaction mixture, optionally in the presence of copper salts.

The compounds of formula IX-a (IX-a)

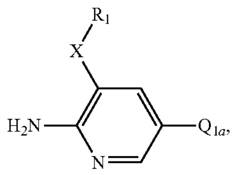

wherein $R_1$ and X are as defined under formula I above, and $Q_1a$ is trifluoromethyl, 1,1-difluoroethyl or —$N(CH_3)COCH_3$, are novel, especially developed for the preparation of the compounds of formula I according to the invention and therefore represent a further object of the invention. The preferences and preferred embodiments of the substituents of the compounds of formula I are also valid for the compounds of formula IX-a.

The subgroup of compounds of formula I, wherein Q is defined as Qb, in which A, $Q_1$, $R_2$, X and $R_1$ are as defined in formula I, may be defined as compounds of formula I-Qb (scheme 10).

Scheme 10

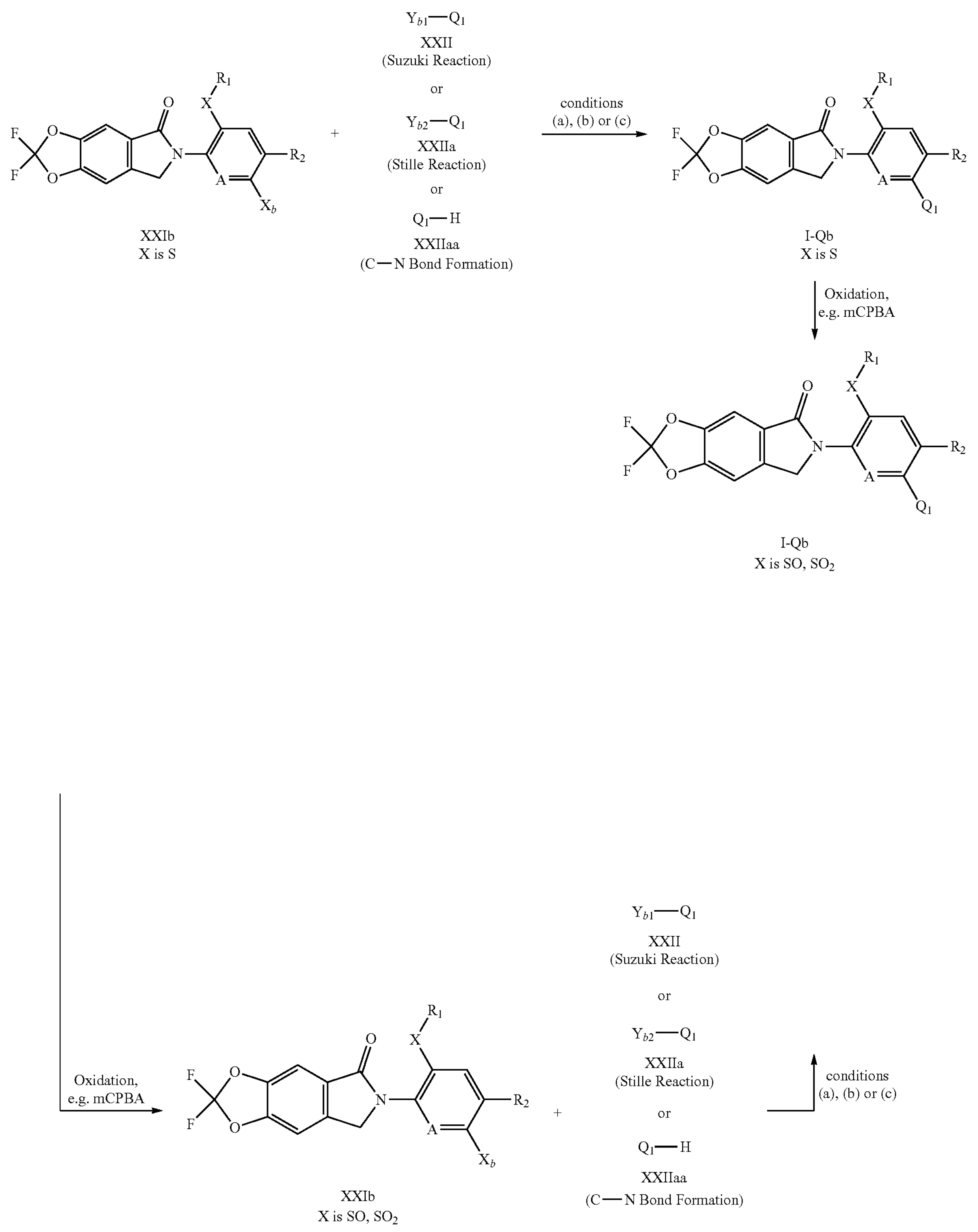

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.
(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

In the particular situation within scheme 10 when $Q_1$ is an optionally substituted triazole linked via a ring nitrogen atom to the ring which contains the group A, then compounds of formula I-Qb, wherein X is SO or $SO_2$, may be prepared from compounds of formula XXIb, wherein A, $R_1$ and $R_2$ are as defined in formula I above and in which X is SO or $SO_2$, and wherein $X_b$ is a leaving group like, for example, chlorine, bromine or iodine (preferably chlorine or bromine), or an aryl- or alkylsulfonate such as trifluoromethanesulfonate, by reaction (C—N bond formation) with an optionally substituted triazole $Q_1$-H (which contains an appropriate NH functionality) (XXIIaa), wherein $Q_1$ is N-linked triazolyl, in solvents such as alcohols (eg. methanol, ethanol, isopropanol, or higher boiling linear or branched alcohols), pyridine or acetic acid, optionally in the presence of an additional base, such as potassium carbonate $K_2CO_3$ or cesium carbonate $Cs_2CO_3$, optionally in the presence of a copper catalyst, for example copper(I) iodide, at temperatures between 30-180° C., optionally under microwave irradiation.

In the particular situation within scheme 10 when $Q_1$ is —$N(R_3)C(=O)R_4$, or —$N(R_3)CON(R_3)_2$, wherein $R_3$ and $R_4$ are as defined in formula I, then compounds of formula I-Qb, wherein X is SO or $SO_2$, may be prepared from compounds of formula XXIb, wherein A, $R_1$, and $R_2$, are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $Q_1$-H (XXIIaa) equivalent to $HN(R_3)COR_4$, or $HN(R_3)CON(R_3)_2$, wherein $R_3$ and $R_4$ are as defined in formula I. Such a reaction is performed in the presence of a base, such as potassium carbonate, cesium carbonate, sodium hydroxide, in an inert solvent, such as toluene, dimethylformamide DMF, N-methyl pyrrolidine NMP, dimethyl sulfoxide DMSO, dioxane, tetrahydrofuran THF, and the like, optionally in the presence of a catalyst, for example palladium(II) acetate, bis(dibenzylideneacetone)palladium(0) ($Pd(dba)_2$) or tris(dibenzylideneacetone)dipalladium(0) ($Pd_2(dba)_3$, optionally in form of a chloroform adduct), or a palladium pre-catalyst such as for example tert-BuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

In the particular situation within scheme 10 when $Q_1$ is —$N(R_3)_2$, wherein $R_3$ is as defined in formula I, then compounds of formula I-Qb, wherein X is SO or $SO_2$, may be prepared from compounds of formula XXIb, wherein A, $R_1$, and $R_2$ are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction (C—N bond formation) with a reagent $Q_1$-H (XXIIaa) equivalent to $HN(R_3)_2$, or a salt thereof (such as a hydrohalide salt, preferably a hydrochloride or a hydrobromide salt, or a trifluoroacetic acid salt, or any other equivalent salt), wherein $R_3$ is as defined in formula I. Such a reaction is commonly performed in an inert solvent such as alcohols, amides, esters, ethers, nitriles and water, particularly preferred are methanol, ethanol, 2,2,2-trifluoroethanol, propanol, isopropanol, N,N-dimethylformamide, N,N-dimethylacetamide, dioxane, tetrahydrofuran, dimethoxyethane, acetonitrile, ethyl acetate, toluene, water or mixtures thereof, at temperatures between 0-150° C., optionally under microwave irradiation or pressurized conditions using an autoclave, optionally in the presence of a copper catalyst, such as copper powder, copper(I) iodide or copper sulfate (optionally in form of a hydrate), or mixtures thereof, optionally in presence a ligand, for example diamine ligands (e.g. N,N'-dimethylethylenediamine or trans-cyclohexyldiamine) or dibenzylideneacetone (dba), or 1,10-phenanthroline, and optionally in presence of a base such as potassium phosphate.

Reagents $HN(R_3)_2$, $HN(R_3)COR_4$, or $HN(R_3)CON(R_3)_2$, wherein $R_3$ and $R_4$ are as defined in formula I, are either known, commercially available or may be prepared by methods known to a person skilled in the art.

Alternatively, compounds of formula I-Qb, wherein X is SO or $SO_2$, may be prepared by a Suzuki reaction, which involves for example, reacting compounds of formula XXIb, wherein A, $R_1$, and $R_2$ are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate, with compounds of formula (XXII), wherein $Q_1$ is as defined in formula I, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction may be catalyzed by a palladium based catalyst, for example tetrakis(triphenylphosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethyl-formamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 576, 1999, 147-168.

Alternatively compounds of formula I-Qb, wherein X is SO or $SO_2$, may be prepared by a Stille reaction between compounds of formula (XXIIa), wherein $Q_1$ is as defined above, and wherein $Y_{b2}$ is a trialkyltin derivative, preferably tri-n-butyl tin or tri-methyl-tin, and compounds of formula XXIb, wherein A, $R_1$, and $R_2$ are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate. Such Stille reactions are usually carried out in the presence of a palladium catalyst, for example tetrakis(triphenylphosphine)palladium(0), or bis (triphenylphosphine)palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I) iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136.

When $Q_1$ is a five-membered aromatic ring system linked via a ring nitrogen atom to the ring which contains the substituent A, then compounds of formula I-Qb, wherein X is SO or $SO_2$, may be prepared from compounds of formula XXIb, wherein A, $R_1$, and $R_2$ are as defined in formula I, and in which X is SO or $SO_2$, and wherein Xb is a leaving group like, for example, chlorine, bromine or iodine (preferably chlorine or bromine), or an aryl- or alkylsulfonate such as trifluoromethanesulfonate, by reaction with a heterocycle $Q_1$-H (which contains an appropriate NH functionality) (XXIIaa), wherein $Q_1$ is as defined above, in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethyl-ethylene-diamine, in an inert solvent such as N-methylpyrrolidone NMP or N,N-dimethylformamide DMF at temperatures between 30-150° C., optionally under microwave irradiation.

Oxidation of compounds of formula XXIb, wherein A, $R_1$, and $R_2$ are as defined in formula I, and in which X is S, and wherein Xb is a leaving group like, for example, chlorine, bromine or iodine (preferably chlorine or bromine), or an aryl- or alkylsulfonate such as trifluoromethanesulfonate, with a suitable oxidizing agent, into compounds of formula XXIb, wherein X is SO or $SO_2$ may be achieved under conditions already described above.

A large number of compounds of the formula (XXII), (XXIIa) and (XXIIaa) are commercially available or can be prepared by those skilled in the art.

Alternatively, compounds of formula I-Qb, wherein X is SO or $SO_2$, may be prepared from compounds of formula XXIb, wherein X is S (sulfide) by involving the same chemistry as described above, but by changing the order of the steps (i.e. by running the sequence XXIb (X is S) to I-Qb (X is S) via Suzuki, Stille or C—N bond formation, followed by an oxidation step to form I-Qb (X is SO or $SO_2$).

The subgroup of compounds of formula I, wherein Q is defined as Qa, in which A, $Q_1$, $R_2$, X and $R_1$ are as defined in formula I, may be defined as compounds of formula I-Qa (scheme 11). The chemistry described previously in scheme 10 to access compounds of formula I-Qb from compounds of formula XXIb, can be applied analogously (scheme 11) for the preparation of compounds of formula I-Qa from compounds of formula XXIa, wherein all substituent definitions mentioned previously remain valid.

Scheme 11

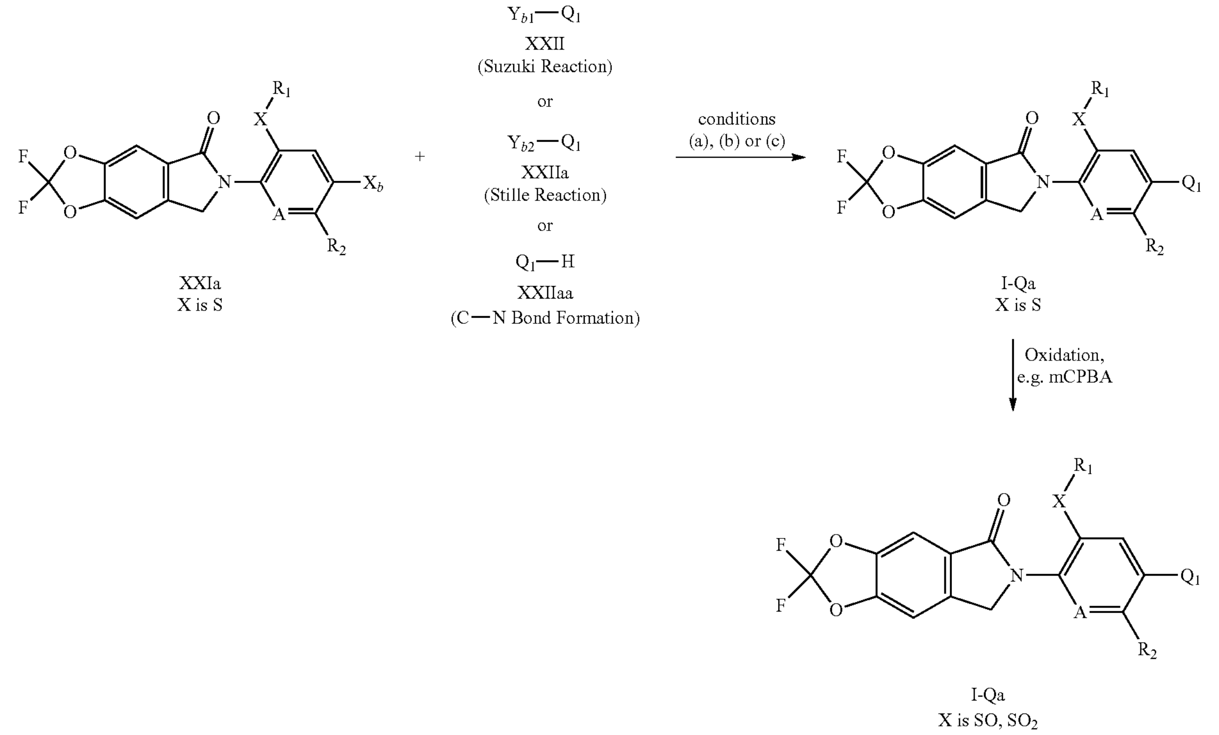

-continued

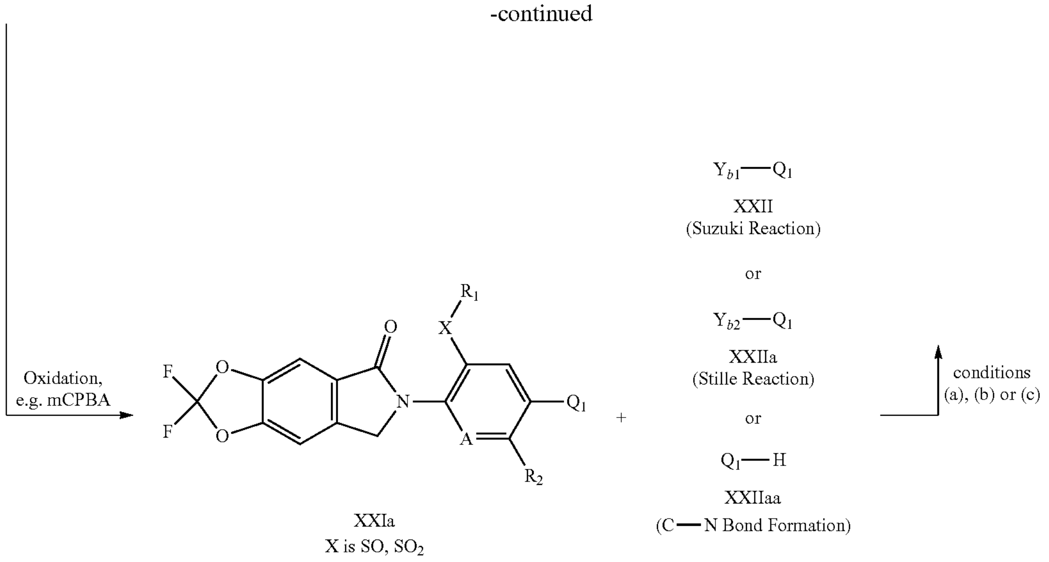

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.
(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

The subgroup of compounds of formula I, wherein Q is defined as Qc, in which A, $Q_1$, $R_1$, $R_5$, X and $R_6$ are as defined in formula I, may be defined as compounds of formula I-Qc (scheme 12). The chemistry described previously in scheme 10 to access compounds of formula I-Qb from compounds of formula XXIb, can be applied analogously (scheme 12) for the preparation of compounds of formula I-Qc from compounds of formula XXIc, wherein all substituent definitions mentioned previously remain valid.

Scheme 12

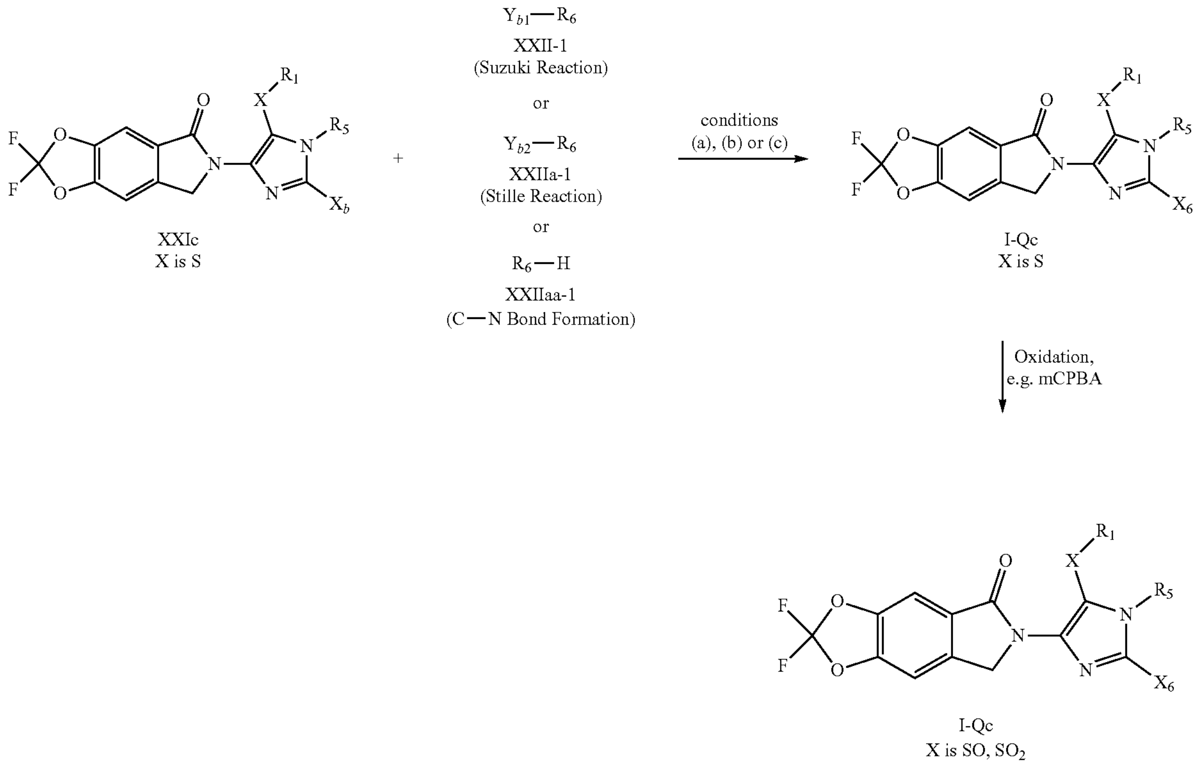

-continued

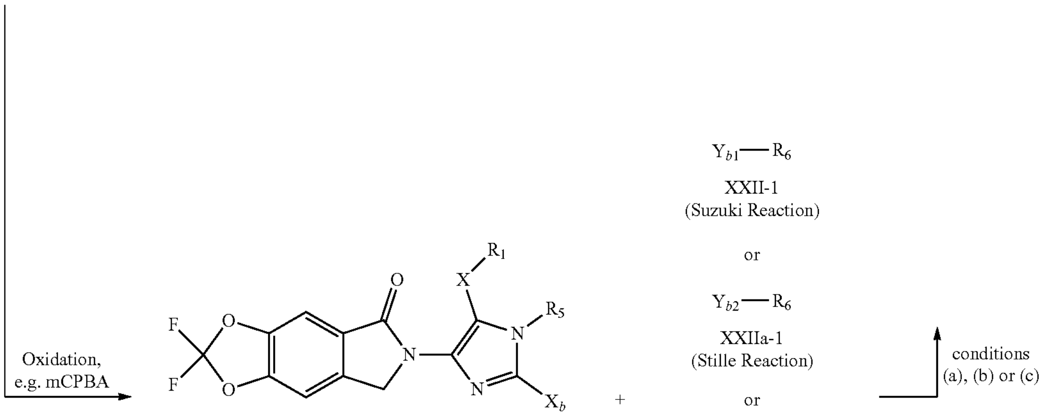

XXIc
X is SO, $SO_2$ $Y_{b1}$—$R_6$
XXII-1
(Suzuki Reaction)

or $Y_{b2}$—$R_6$
XXIIa-1
(Stille Reaction)

or $R_6$—H
XXIIaa-1
(C—N Bond Formation)

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.
(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

A large number of compounds of the formula (XXII-1), (XXIIa-1) and (XXIIaa-1), wherein each $R_6$ are as defined in formula I, and $Y_{b1}$ and $Y_{b2}$ are as defined above in scheme 10, are commercially available or can be prepared by those skilled in the art.

Alternatively, compounds of formula XVIII-c, in which X is $SO_2$, and wherein $R_5$, $R_6$ and $R_1$ are as defined in formula I above, Scheme 13

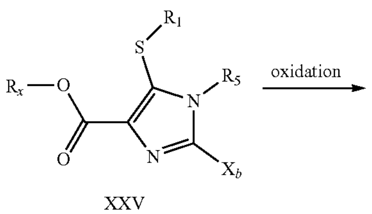

XXV

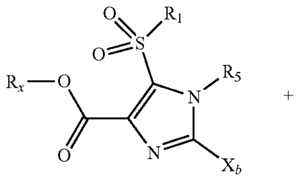

XXIV

-continued $Y_{b1}$—$R_6$
XXII-1
(Suzuki Reaction)

or $Y_{b2}$—$R_6$
XXIIa-1
(Stille Reaction)

or $R_6$—H
XXIIaa-1
(C—N Bond Formation)

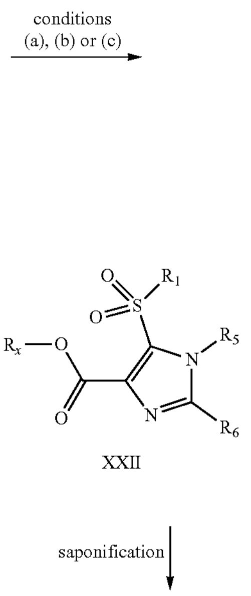

XXII

-continued

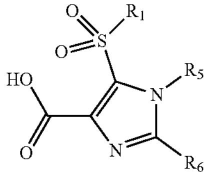

XXII-c
X = $SO_2$ (a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.
(c) C—N bond formation: Optional base (e.g. $K_2CO_3$ or $Cs_2CO_3$), optional presence of copper or palladium catalyst, optional additive (such as N,N'-dimethylethylenediamine), optional ligand (such as Xantphos), solvent (e.g. dioxane, pyridine or N,N-dimethylformamide DMF), 25-180° C.

can be prepared (scheme 13) by a saponification reaction of compounds of formula XXIII, wherein $R_5$, $R_6$ and $R_1$ are as defined in formula I above, and Rx is $C_1$-$C_6$alkyl, benzyl or phenyl, in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), under conditions already described above (see discussions on converting (VI) to (X) in scheme 3, and (XVII) into (X) in scheme 3a; alternatively, Krapcho-type conditions as described above may also be used).

Compounds of formula XXIII, wherein $R_5$, $R_6$ and $R_1$ are as defined in formula I above, and Rx is $C_1$-$C_6$alkyl, benzyl or phenyl, can be prepared from compounds of formula XXIV, wherein $R_5$ and $R_1$ are as defined in formula I above, and Rx is $C_1$-$C_6$alkyl, benzyl or phenyl, and Xb is a leaving group like, for example, chlorine, bromine or iodine (preferably chlorine or bromine), or an aryl- or (halo)alkylsulfonate such as trifluoromethanesulfonate, via Suzuki, Stille or C—N bond formation, involving reagents of the formula XXII-1, XXIIa-1 or XXIIaa-1, wherein $R_6$ is as defined in formula I above, and $Y_{b1}$ and $Y_{b2}$ are as defined above in scheme 10, under conditions already described above (see discussions on converting (XXIb) to (I-Qb) in scheme 10).

Compounds of formula XXIV, wherein $R_5$ and $R_1$ are as defined in formula I above, and Rx is $C_1$-$C_6$alkyl, benzyl or phenyl, and Xb is a leaving group like, for example, chlorine, bromine or iodine (preferably chlorine or bromine), or an aryl- or (halo)alkylsulfonate such as trifluoromethanesulfonate, can be prepared by oxidation of compounds of formula XXV, wherein $R_5$ and $R_1$ are as defined in formula I above, and Rx is $C_1$-$C_6$alkyl, benzyl or phenyl, and Xb is a leaving group like, for example, chlorine, bromine or iodine (preferably chlorine or bromine), or an aryl- or (halo)alkylsulfonate such as trifluoromethanesulfonate, involving a suitable oxidizing agent, and under conditions already described above.

Compounds of formula XXV, wherein $R_5$ and $R_1$ are as defined in formula I above, and Rx is $C_1$-$C_6$alkyl, benzyl or phenyl, and Xb is a leaving group like, for example, chlorine, bromine or iodine (preferably chlorine or bromine), or an aryl- or (halo)alkylsulfonate such as trifluoromethanesulfonate, are either known or may be prepared according to procedures found in the literature. For example, the compound of formula XXV, wherein $R_1$ is ethyl, $R_5$ is methyl, Xb is bromo and Rx is ethyl (CAS 2407490-49-5), is described in WO2018130443, WO2018130437 and WO2020002082.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention, and by post modification of compounds of with reactions such as oxidation, alkylation, reduction, acylation and other methods known by those skilled in the art.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.,* 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the following Tables A-1 to A-12, D-1 to D-12, E-1 to E-12 and G1 to G-12 can be prepared according to the methods described above. The examples which follow are intended to illustrate the invention and show preferred compounds of formula I, in the form of a compound of formula I-1 to I-4.

The tables below illustrate specific compounds of the invention.

In the tables, $CH_2cPr$ means $CH_2$-cyclopropyl.

The tables below illustrate specific compounds of the invention.

(I-1)

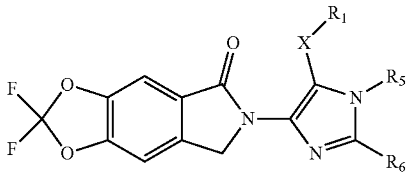

Table A-1 provides 20 compounds A-1.001 to A-1.020 of formula I-1 wherein X is S, $R_1$ is $CH_2CH_3$, $R_5$ is methyl and $R_6$ are as defined in table B.

TABLE B

| Substituent definitions of $R_6$ | |
|---|---|
| Index | $R_6$ |
| 1 | 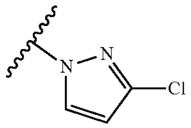 [SMILES: *n1ccc(Cl)n1] |
| 2 | 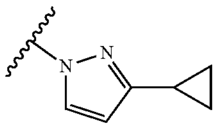 [SMILES: *n1ccc(C2CC2)n1] |
| 3 | 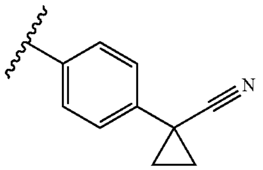 [SMILES: *c1ccc(C2(C#N)CC2)cc1] |
| 4 | 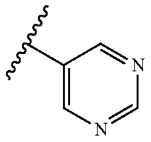 [SMILES: *c1cncnc1] |
| 5 | 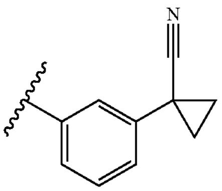 [SMILES: *c1cccc(C2(C#N)CC2)c1] |

TABLE B-continued

| Substituent definitions of $R_6$ | |
| --- | --- |
| Index | $R_6$ |
| 6 | 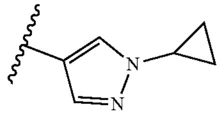 [SMILES: *c1cnn(C2CC2)c1] |
| 7 | 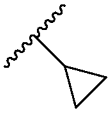 [SMILES: *C1CC1] |
| 8 | 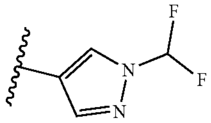 [SMILES: *c1cnn(C(F)F)c1] |
| 9 | 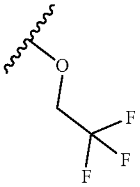 [SMILES: *OCC(F)(F)F] |
| 10 | 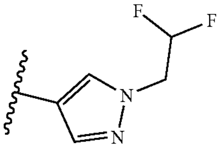 [SMILES: *c1cnn(CC(F)F)c1] |
| 11 | 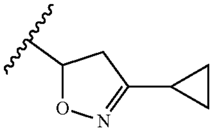 [SMILES: *C1CC(C2CC2)=NO1] |
| 12 | 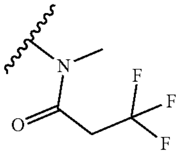 [SMILES: *N(C)C(=O)CC(F)(F)F] |
| 13 | 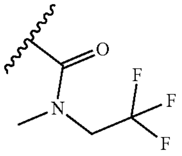 [SMILES: *C(=O)N(C)CC(F)(F)F] |
| 14 | 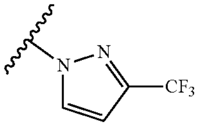 [SMILES: *n1ccc(C(F)(F)F)n1] |
| 15 | 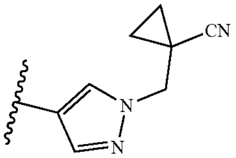 [SMILES: *c1cnn(CC2(C#N)CC2)c1] |
| 16 | 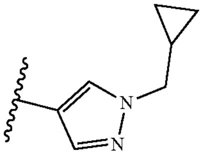 [SMILES: *c1cnn(CC2CC2)c1] |
| 17 | 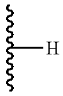 |
| 18 | 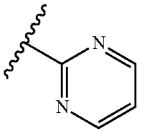 [SMILES: *c1ncccn1] |
| 19 | 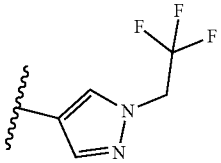 [SMILES: *c1cnn(CC(F)(F)F)c1] |
| 20 | 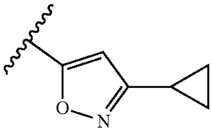 [SMILES: *c1cc(C2CC2)no1] |

Table A-2 provides 20 compounds A-2.001 to A-2.020 of formula I-1 wherein X is S, $R_1$ is $CH_2CH_3$, $R_5$ is ethyl and $R_6$ are as defined in table B.

Table A-3 provides 20 compounds A-3.001 to A-3.020 of formula I-1 wherein X is S, $R_1$ is $CH_2cPr$, $R_5$ is methyl and $R_6$ are as defined in table B.

Table A-4 provides 20 compounds A-4.001 to A-4.020 of formula I-1 wherein X is S, $R_1$ is $CH_2cPr$, $R_5$ is ethyl and $R_6$ are as defined in table B.

Table A-5 provides 20 compounds A-5.001 to A-5.020 of formula I-1 wherein X is SO, $R_1$ is $CH_2CH_3$, $R_5$ is methyl and $R_6$ are as defined in table B.

Table A-6 provides 20 compounds A-6.001 to A-6.020 of formula I-1 wherein X is SO, $R_1$ is $CH_2CH_3$, $R_5$ is ethyl and $R_6$ are as defined in table B.

Table A-7 provides 20 compounds A-7.001 to A-7.020 of formula I-1 wherein X is SO, $R_1$ is $CH_2cPr$, $R_5$ is methyl and $R_6$ are as defined in table B.

Table A-8 provides 20 compounds A-8.001 to A-8.020 of formula I-1 wherein X is SO, $R_1$ is $CH_2cPr$, $R_5$ is ethyl and $R_6$ are as defined in table B.

Table A-9 provides 20 compounds A-9.001 to A-9.020 of formula I-1 wherein X is $SO_2$, $R_1$ is $CH_2CH_3$, $R_5$ is methyl and $R_6$ are as defined in table B.

Table A-10 provides 20 compounds A-10.001 to A-10.020 of formula I-1 wherein X is $SO_2$, $R_1$ is $CH_2CH_3$, $R_5$ is ethyl and $R_6$ are as defined in table B.

Table A-11 provides 20 compounds A-11.001 to A-11.020 of formula I-1 wherein X is $SO_2$, $R_1$ is $CH_2cPr$, $R_5$ is methyl and $R_6$ are as defined in table B.

Table A-12 provides 20 compounds A-12.001 to A-12.020 of formula I-1 wherein X is $SO_2$, $R_1$ is $CH_2cPr$, $R_5$ is ethyl and $R_6$ are as defined in table B.

The tables below illustrate further specific compounds of the invention.

(I-2)

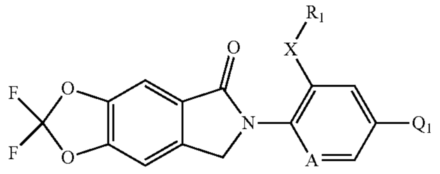

Table D-1 provides 19 compounds D-1.001 to D-1.019 of formula I-2 wherein X is S, $R_1$ is $CH_2CH_3$, A is N and $Q_1$ are as defined in table C.

TABLE C

| Substituent definitions of $Q_1$ | |
|---|---|
| Index | $Q_1$ |
| 1 | 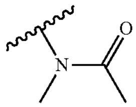 [SMILES: *N(C)C(C)=O] |
| 2 | 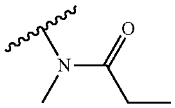 [SMILES: *N(C)C(=O)CC] |
| 3 | 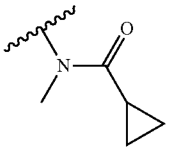 |
| 4 | 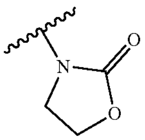 [SMILES: *N1CCOC1=O] |
| 5 | 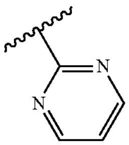 [SMILES: *c1ncccn1] |
| 6 | 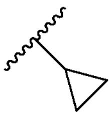 [SMILES: *C1CC1] |
| 7 | 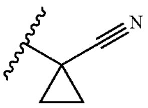 [SMILES: *C1(C#N)CC1] |

TABLE C-continued

| Substituent definitions of $Q_1$ | |
|---|---|
| Index | $Q_1$ |
| 8 | 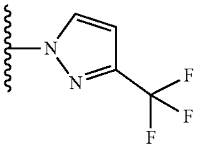 |
| 9 | 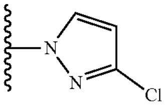 |
| 10 | 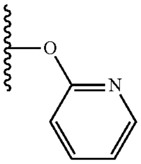 [SMILES: *Oc1ccccn1] |
| 11 | 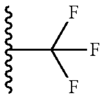 |
| 12 | 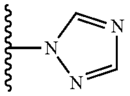 [SMILES: *n1cncn1] |
| 13 | 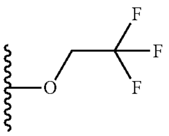 |
| 14 | 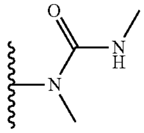 [SMILES: *N(C)C(=O)NC] |
| 15 | 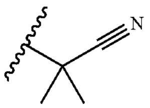 [SMILES: *C(C)(C)C#N] |
| 16 | 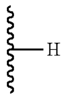 [SMILES: *[H]] |
| 17 | 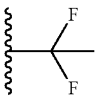 |
| 18 | 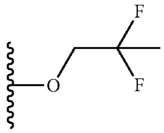 [SMILES: *OCC(C)(F)F] |

TABLE C-continued

| Substituent definitions of $Q_1$ | |
|---|---|
| Index | $Q_1$ |
| 19 | 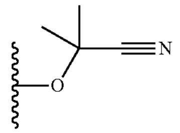 [SMILES: *OC(C)(C)C#N] |

Table D-2 provides 19 compounds D-2.001 to D-2.019 of formula I-2 wherein X is S, $R_1$ is $CH_2CH_3$, A is CH and Q are as defined in table C.

Table 0-3 provides 19 compounds 0-3.001 to 0-3.019 of formula I-2 wherein X is S, $R_1$ is $CH_2cPr$, A is N and Q, are as defined in table C.

Table 0-4 provides 19 compounds 0-4.001 to 0-4.019 of formula I-2 wherein X is S, $R_1$ is $CH_2cPr$, A is OH and Q, are as defined in table C.

Table D-5 provides 19 compounds D-5.001 to D-5.019 of formula I-2 wherein X is SO, $R_1$ is $CH_2CH_3$, A is N and $Q_1$ are as defined in table C.

Table D-6 provides 19 compounds D-6.001 to D-6.019 of formula I-2 wherein X is SO, $R_1$ is $CH_2CH_3$, A is CH and $Q_1$ are as defined in table C.

Table D-7 provides 19 compounds D-7.001 to D-7.019 of formula I-2 wherein X is SO, $R_1$ is $CH_2cPr$, A is N and $Q_1$ are as defined in table C.

Table D-8 provides 19 compounds D-8.001 to D-8.019 of formula I-2 wherein X is SO, $R_1$ is $CH_2cPr$, A is CH and $Q_1$ are as defined in table C.

Table D-9 provides 19 compounds D-9.001 to D-9.019 of formula I-2 wherein X is $SO_2$, $R_1$ is $CH_2CH_3$, A is N and $Q_1$ are as defined in table C.

Table D-10 provides 19 compounds D-10.001 to D-10.019 of formula I-2 wherein X is $SO_2$, $R_1$ is $CH_2CH_3$, A is CH and $Q_1$ are as defined in table C.

Table D-11 provides 19 compounds D-11.001 to D-11.019 of formula I-2 wherein X is $SO_2$, $R_1$ is $CH_2cPr$, A is N and $Q_1$ are as defined in table C.

Table D-12 provides 19 compounds D-12.001 to D-12.019 of formula I-2 wherein X is $SO_2$, $R_1$ is $CH_2cPr$, A is CH and $Q_1$ are as defined in table C.

The tables below illustrate further specific compounds of the invention.

(I-3)

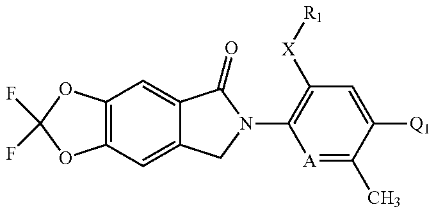

Table E-1 provides 19 compounds E-1.001 to E-1.019 of formula I-3 wherein X is S, $R_1$ is $CH_2CH_3$, A is N and $Q_1$ are as defined in table C.

Table E-2 provides 19 compounds E-2.001 to E-2.019 of formula I-3 wherein X is S, $R_1$ is $CH_2CH_3$, A is CH and $Q_1$ are as defined in table C.

Table E-3 provides 19 compounds E-3.001 to E-3.019 of formula I-3 wherein X is S, $R_1$ is $CH_2cPr$, A is N and $Q_1$ are as defined in table C.

Table E-4 provides 19 compounds E-4.001 to E-4.019 of formula I-3 wherein X is S, $R_1$ is $CH_2cPr$, A is CH and $Q_1$ are as defined in table C.

Table E-5 provides 19 compounds E-5.001 to E-5.019 of formula I-3 wherein X is SO, $R_1$ is $CH_2CH_3$, A is N and $Q_1$ are as defined in table C.

Table E-6 provides 19 compounds E-6.001 to E-6.019 of formula I-3 wherein X is SO, $R_1$ is $CH_2CH_3$, A is CH and $Q_1$ are as defined in table C.

Table E-7 provides 19 compounds E-7.001 to E-7.019 of formula I-3 wherein X is SO, $R_1$ is $CH_2cPr$, A is N and $Q_1$ are as defined in table C.

Table E-8 provides 19 compounds E-8.001 to E-8.019 of formula I-3 wherein X is SO, $R_1$ is $CH_2cPr$, A is CH and $Q_1$ are as defined in table C.

Table E-9 provides 19 compounds E-9.001 to E-9.019 of formula I-3 wherein X is $SO_2$, $R_1$ is $CH_2CH_3$, A is N and $Q_1$ are as defined in table C.

Table E-10 provides 19 compounds E-10.001 to E-10.019 of formula I-3 wherein X is $SO_2$, $R_1$ is $CH_2CH_3$, A is CH and $Q_1$ are as defined in table C.

Table E-11 provides 19 compounds E-11.001 to E-11.019 of formula I-3 wherein X is $SO_2$, $R_1$ is $CH_2cPr$, A is N and $Q_1$ are as defined in table C.

Table E-12 provides 19 compounds E-12.001 to E-12.019 of formula I-3 wherein X is $SO_2$, $R_1$ is $CH_2cPr$, A is CH and $Q_1$ are as defined in table C.

The tables below illustrate further specific compounds of the invention.

(I-4)

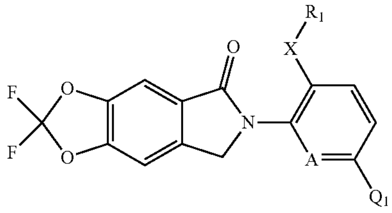

Table G-1 provides 10 compounds G-1.001 to G-1.010 of formula I-4 wherein X is S, $R_1$ is $CH_2CH_3$, A is N and $Q_1$ are as defined in table F.

TABLE F

| Substituent definitions of $Q_1$ | |
|---|---|
| Index | $Q_1$ |
| 1 | 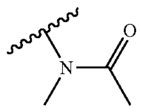 [SMILES: *N(C)C(C)=O] |
| 2 | 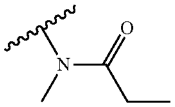 [SMILES: *N(C)C(=O)CC] |
| 3 | 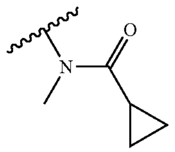 [SMILES: *N(C)C(=O)C1CC1] |

TABLE F-continued

| Substituent definitions of $Q_1$ | |
|---|---|
| Index | $Q_1$ |
| 4 | 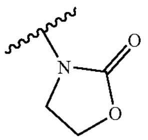 [SMILES: *N1CCOC1=O] |
| 5 | 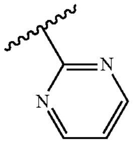 |
| 6 | 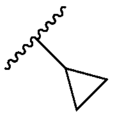 [SMILES: *C1CC1] |
| 7 | 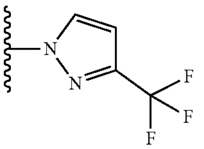 [SMILES: *n1ccc(C(F)(F)F)n1] |
| 8 | 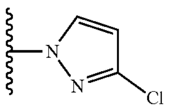 [SMILES: *n1ccc(Cl)n1] |
| 9 | 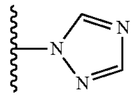 |
| 10 | 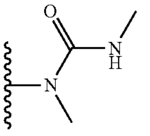 [SMILES: *N(C)C(=O)NC] |

Table G-2 provides 10 compounds G-2.001 to G-2.010 of formula I-4 wherein X is S, $R_1$ is $CH_2CH_3$, A is CH and $Q_1$ are as defined in table F.

Table G-3 provides 10 compounds G-3.001 to G-3.010 of formula I-4 wherein X is S, $R_1$ is $CH_2cPr$, A is N and $Q_1$ are as defined in table F.

Table G-4 provides 10 compounds G-4.001 to G-4.010 of formula I-4 wherein X is S, $R_1$ is $CH_2cPr$, A is CH and $Q_1$ are as defined in table F.

Table G-5 provides 10 compounds G-5.001 to G-5.010 of formula I-4 wherein X is SO, $R_1$ is $CH_2CH_3$, A is N and $Q_1$ are as defined in table F.

Table G-6 provides 10 compounds G-6.001 to G-6.010 of formula I-4 wherein X is SO, $R_1$ is $CH_2CH_3$, A is CH and $Q_1$ are as defined in table F.

Table G-7 provides 10 compounds G-7.001 to G-7.010 of formula I-4 wherein X is SO, $R_1$ is $CH_2cPr$, A is N and $Q_1$ are as defined in table F.

Table G-8 provides 10 compounds G-8.001 to G-8.010 of formula I-4 wherein X is SO, $R_1$ is $CH_2cPr$, A is CH and $Q_1$ are as defined in table F.

Table G-9 provides 10 compounds G-9.001 to G-9.010 of formula I-4 wherein X is $SO_2$, $R_1$ is $CH_2CH_3$, A is N and $Q_1$ are as defined in table F.

Table G-10 provides 10 compounds G-10.001 to G-10.010 of formula I-4 wherein X is $SO_2$, $R_1$ is $CH_2CH_3$, A is CH and $Q_1$ are as defined in table F.

Table G-11 provides 10 compounds G-11.001 to G-11.010 of formula I-4 wherein X is $SO_2$, $R_1$ is $CH_2cPr$, A is N and $Q_1$ are as defined in table F.

Table G-12 provides 10 compounds G-12.001 to G-12.010 of formula I-4 wherein X is $SO_2$, $R_1$ is $CH_2cPr$, A is CH and $Q_1$ are as defined in table F.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the above-mentioned animal pests are:

from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., Scarabeidae, *Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euschistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., Aphididae, *Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., Diprionidae, *Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo* supressalis (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, Criconema species, Criconemella species, Criconemoides species, Mesocriconema species; Stem and bulb nematodes, *Ditylenchus destructor, Ditylenchus dipsaci* and other *Ditylenchus* species; Awl nematodes, Dolichodorus species; Spiral nematodes, Heliocotylenchus *multicinctus* and other *Helicotylenchus* species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; Scutellonema species; Stubby root nematodes, *Trichodorus primitivus* and other *Trichodorus* species, Paratrichodorus species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., Hypsoperine spp., *Macroposthonia* spp., Melinius spp., Punctodera spp., and Quinisulcius spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); Cepaea (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G.

*trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); *Opeas; Pomacea* (*P. canaticulata*); *Vallonia* and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as 6-endotoxins, e.g. Cry1Ab, Cry1Ac, Cry1F, Cry1 Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by 6-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603 x MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603 x MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |

TABLE B-continued

Examples of native woodborers of economic importance.

| Family | Species | Host or Crop Infested |
|---|---|---|
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *Ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana*, Blattelagermanica and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as Sirexjuvencus, *Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances. A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers. The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: quaternary pump, heated column compartment and diode-array detector. Column: Acquity UPLC HSS T3 C18, 1.8 μm, 30×2.1 mm, Temp: 40° C., DAD Wavelength range (nm): 200 to 400, Solvent Gradient: A=water+5% Acetonitrile+0.1% HCOOH, B=Acetonitrile+0.05% HCOOH: gradient: 0 min 10% B; 0.-0.2 min 10-50% B; 0.2-0.7 min 50-100% B; 0.7-1.3 min 100% B; 1.3-1.4 min 100-10% B; 1.4-1.6 min 10% B; Flow (mL/min) 0.6.

Method 2:

Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 4.00 kV, Fragmentor: 100 V, Desolvatation Temperature: 350° C., Gas Flow: 11 L/min, Nebulizer Gas: 45 psi, Mass range: 110 to 1000 Da) and a 1200 Series HPLC from Agilent: quaternary pump, heated column compartment and diode-array detector. Column: KINETEX EVO C18, 2.6 μm, 50×4.6 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 10% B, 90% A; 0.9-1.8 min 100% B; 1.8-2.2 min 100-10% B; 2.2-2.5 min 10% B; Flow (mL/min) 1.8.

Method 3:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: quaternary pump, heated column compartment and diode-array detector. Column: Acquity UPLC HSS T3 C18, 1.8 μm, 30×2.1 mm, Temp: 40° C., DAD Wavelength range (nm): 210 to 400, Solvent Gradient: A=water+5% Acetonitrile+0.1% HCOOH, B=Acetonitrile+0.05% HCOOH: gradient: 0 min 10% B; 0.-0.2 min 50% B; 0.2-0.7 min 100% B; 0.7-1.3 min 100%; 1.3-1.4 min 10% B; 1.4-1.6 min 10% B; Flow (mL/min) 0.8.

Example P1: Preparation of 1-[6-(2,2-difluoro-7-oxo-5H-[1,3]dioxolo[4,5-f]isoindol-6-yl)-5-ethylsulfonyl-3-pyridyl]cyclooropanecarbonitrile (Compound P1)

(P1)

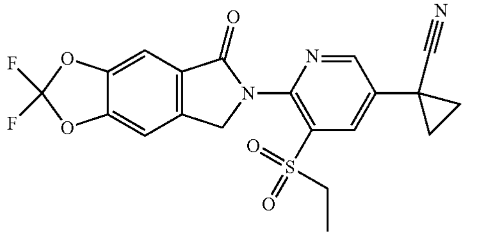

Step A1: Preparation of (2,2-difluoro-1,3-benzodioxol-5-yl)methanol (Intermediate I-1)

(I-1)

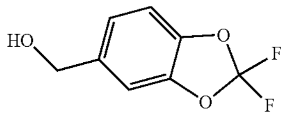

To 0° C. cooled solution of 2,2-difluoro-1,3-benzodioxole-5-carbaldehyde (CAS 656-42-8) (15 g, 76.56 mmol) in methanol (75 mL) was added sodium borohydride (4.57 g, 114.84 mmol) slowly. The reaction mixture was stirred at room temperature for overnight. After completion, the reaction mass was concentrated in vacuo, quenched with an aqueous ammonium chloride solution and extracted with ethyl acetate. The organic layer was dried over magnesium sulfate and concentrated in vacuo to afford (2,2-difluoro-1,3-benzodioxol-5-yl)methanol as a colourless liquid. $^{1}H$ NMR (400 MHz, $CDCl_3$) δ ppm: 1.91 (br s, 1H), 4.69 (br s, 2H), 7.03-7.09 (m, 2H), 7.14 (s, 1H).

Step A2: Preparation of 6-chloro-2,2-difluoro-1,3-benzodioxole-5-carbaldehyde (Intermediate I-2)

(I-2)

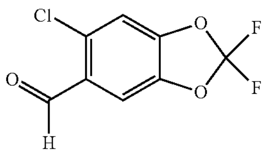

To a solution of (2,2-difluoro-1,3-benzodioxol-5-yl) methanol (Intermediate I-1 prepared as described above) (10 g, 50.49 mmol) in acetonitrile (60 mL) was added N-chlorosuccinimide (17.20 g, 126.24 mmol). The reaction mixture was stirred at room temperature for overnight. After completion, the reaction mass was concentrated in vacuo, triturated with cyclohexane, filtered through a Buchner funnel and filtrate was concentrated in vacuo. The crude compound was purified by combiflash (silica gel, 0-30% ethyl acetate in cyclohexane) to afford pure 6-chloro-2,2-difluoro-1,3-benzodioxole-5-carbaldehyde as a colourless liquid. $^{1}H$ NMR (400 MHz, $CDCl_3$) δ ppm: 7.22 (s, 1H), 7.66 (s, 1H), 10.41 (s, 1H).

Step A3: Preparation of 2,2-difluoro-6-methyl-1,3-benzodioxole-5-carbaldehyde (Intermediate I-3)

(I-3)

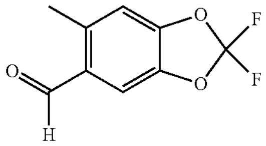

To a solution of 6-chloro-2,2-difluoro-1,3-benzodioxole-5-carbaldehyde (Intermediate I-2 prepared as described above) (1 g, 4.30 mmol) in toluene (10 mL) were added methylboronic acid (1.14 g, 17.22 mmol), followed by a solution of potassium carbonate (1.78 g, 12.92 mmol) in water (3 mL) while purging with nitrogen for 10 minutes. 1,1'-bis(diphenylphosphino)ferrocene-palladium(II)dichloride dichloromethane complex (0.18 g, 0.21 mmol) was added and the reaction mixture heated at 90° C. for 15 hours. The reaction mixture was cooled to room temperature and concentrated in vacuo. The reaction mass was diluted with water and extracted with ethyl acetate. The organic layer was washed with water and brine, dried over sodium sulfate, filtered and concentrated in vacuo. The crude was purified by combiflash (silica gel, 0 to 30% ethyl acetate in cyclohexane) to afford 2,2-difluoro-6-methyl-1,3-benzodioxole-5-carbaldehyde as a brown oil. $^{1}H$ NMR (400 MHz, $CDCl_3$) δ ppm: 2.72 (s, 3H), 6.99 (s, 1H), 7.56 (s, 1H), 10.27 (s, 1H).

Step A4: Preparation of 2,2-difluoro-6-methyl-1,3-benzodioxole-5-carboxylic acid (Intermediate I-4)

(I-4)

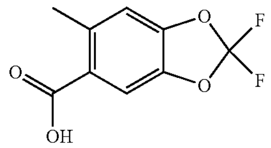

To a solution of silver nitrate (0.57 g, 3.22 mmol) in water (6.8 mL) was added a solution of sodium hydroxide (0.33 g, 8.06 mmol) in water (6.8 mL) dropwise at room temperature. To this reaction mixture, 2,2-difluoro-6-methyl-1,3-benzodioxole-5-carbaldehyde (Intermediate I-3 prepared as described above) (0.34 g, 1.61 mmol) was added portion wise over a period of 20 minutes. The reaction mixture was stirred at room temperature for 2 hours. After completion, the reaction mixture was filtered through celite and the filtrate acidified with an aqueous 2N hydrochloric acid solution. The formed solid was filtered, washed with cold water and dried in vacuo to afford 2,2-difluoro-6-methyl-1,3-benzodioxole-5-carboxylic acid as white solid. LCMS (method 2): Rt=1.42 min, m/z=215 $(M-H)^-$. $^{1}H$ NMR (400 MHz, DMSO-d6) δ ppm: 2.54 (s, 3H), 7.41 (s, 1H), 7.77 (s, 1H).

Step A5: Preparation of ethyl 2,2-difluoro-6-methyl-1,3-benzodioxole-5-carboxylate (Intermediate I-5)

(I-5)

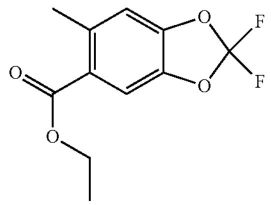

A solution of 2,2-difluoro-6-methyl-1,3-benzodioxole-5-carboxylic acid (Intermediate I-4 prepared as described above) (0.23 g, 1.01 mmol) in ethanol (10 mL) was stirred at room temperature for 15 minutes. To this reaction mass, sulfuric acid (0.02 mL, 0.40 mmol) was added dropwise (exotherm was observed). The reaction mixture was heated at 60° C. for 12 hours. After completion, the reaction mass was concentrated in vacuo, neutralized with an aqueous sodium bicarbonate solution, and the product extracted twice with ethyl acetate. The combined organic layers were dried over sodium sulfate, filtered and concentrated in vacuo to afford ethyl 2,2-difluoro-6-methyl-1,3-benzodioxole-5-carboxylate. The crude was used as such for next step. $^{1}H$ NMR (400 MHz, $CDCl_3$) δ ppm: 1.41 (t, 3H), 2.64 (s, 3H), 4.37 (q, 2H), 6.97 (s, 1H), 7.67 (s, 1H).

Step A6: Preparation of ethyl 6-(bromomethyl)-2,2-difluoro-1,3-benzodioxole-5-carboxylate (Intermediate I-6)

(I-6)

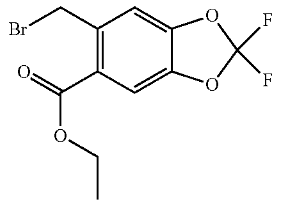

To a solution of ethyl 2,2-difluoro-6-methyl-1,3-benzodioxole-5-carboxylate (Intermediate I-5 prepared as described above) (0.25 g, 0.97 mmol) in benzotrifluoride (3 mL) were added N-bromosuccinimide (0.196 g, 1.06 mmol) and azobisisobutyronitrile (0.016 g, 0.097 mmol) at room temperature. The reaction mixture was heated at 90° C. for 3 hours. The reaction mixture was cooled to room temperature, and concentrated in vacuo. The crude was purified by combiflash (silica gel, 0 to 30% ethyl acetate in cyclohexane) to afford ethyl 6-(bromomethyl)-2,2-difluoro-1,3-benzodioxole-5-carboxylate as colourless gummy mass. $^1H$ NMR (400 MHz, $CDCl_3$) δ ppm: 1.39-1.47 (m, 3H), 4.38-4.45 (m, 2H), 4.97 (s, 2H), 7.20 (s, 1H), 7.71 (s, 1H).

Step B1: Preparation of tert-butyl N-[5-(1-cyanocyclopropyl)-3-ethylsulfanyl-2-pyridyl]carbamate (Intermediate I-7) and 1-(6-amino-5-ethylsulfanyl-3-pyridyl)cyclopropanecarbonitrile (Intermediate I-8)

(I-7)

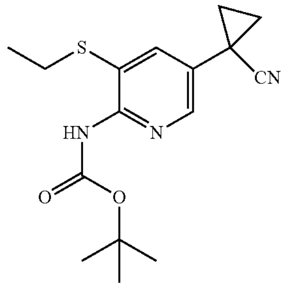

and (I-8)

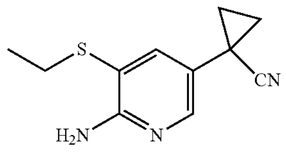

To a solution of 5-(1-cyanocyclopropyl)-3-ethylsulfanyl-pyridine-2-carboxylic acid (CAS 2225113-77-7, prepared as described in WO 2018108726) (0.915 g, 3.68 mmol) in toluene (10 mL) were added triethylamine (0.519 mL, 3.68 mmol) and diphenylphosphoryl azide (0.81 mL, 3.68 mmol). After stirring for 30 minutes at room temperature, tert-butanol (0.69 mL, 7.37 mmol) was added, and the reaction mixture was heated at 90° C. for 3 hours. The reaction mass was diluted with water (100 mL) and the product extracted with ethyl acetate (3×50 mL). The combined organic layers were washed with a saturated sodium bicarbonate solution (20 mL) and brine (30 mL), dried over sodium sulfate and concentrated in vacuo to afford both tert-butyl N-[5-(1-cyanocyclopropyl)-3-ethylsulfanyl-2-pyridyl]carbamate (intermediate I-7) and 1-(6-amino-5-ethylsulfanyl-3-pyridyl)cyclopropanecarbonitrile (intermediate I-8) as a mixture which was used as such for the next step. LCMS (method 3) for tert-butyl N-[5-(1-cyanocyclopropyl)-3-ethylsulfanyl-2-pyridyl]carbamate (intermediate I-7): Rt=0.96 min, m/z=264 [$(M+H)^+$-56].

Step B2: Preparation of 1-(6-amino-5-ethylsulfanyl-3-pyridyl)cyclopropanecarbonitrile (Intermediate I-8)

(I-8)

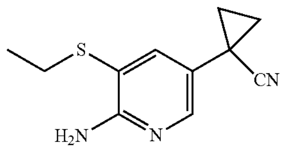

To a mixture of 1-(6-amino-5-ethylsulfanyl-3-pyridyl)cyclopropanecarbonitrile and tert-butyl N-[5-(1-cyanocyclopropyl)-3-ethylsulfanyl-2-pyridyl]carbamate (mixture of intermediate I-7 and 1-8 prepared as described above) (1.2 g, 3.8 mmol) in dichloromethane (10 mL) was added 2,2,2-trifluoroacetic acid (2.9 mL, 38 mmol) under cooling conditions, and the reaction mass was stirred at room temperature overnight. The reaction mixture was diluted with water (50 mL), neutralized with an aqueous saturated sodium bicarbonate solution, and the product extracted with dichloromethane (3×25 mL). The combined organic layers were dried over sodium sulfate, filtered and concentrated in vacuo. The crude compound was purified by combiflash (silica gel, 30% ethyl acetate in cyclohexane) to afford 1-(6-amino-5-ethylsulfanyl-3-pyridyl)cyclopropanecarbonitrile. LCMS (method 3): Rt=0.25 min, m/z=220 $(M+H)^+$.

Step B3: Preparation of 1-(6-amino-5-ethylsulfonyl-3-pyridyl)cyclopropanecarbonitrile (Intermediate I-9)

(I-9)

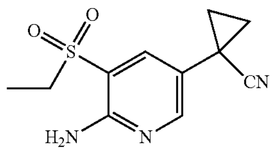

To a 0° C. cooled solution of 1-(6-amino-5-ethylsulfanyl-3-pyridyl)cyclopropanecarbonitrile (Intermediate I-8 prepared as described above) (5.0 g, 23 mmol) in dichloromethane (75 mL) was added 3-chlorobenzenecarboperoxoic acid (12 g, 48 mmol, 70 mass %). After stirring for 30 minutes at 0° C., the reaction mass was quenched with an aqueous 2M sodium hydroxide, and the product extracted with dichloromethane (2×20 mL). The combined organic layers were washed with water (50 mL) and brine (50 mL), dried over sodium sulfate, filtered and concentrated in vacuo. The crude product was purified by combiflash (silica gel, 70% ethyl acetate in cyclohexane) to afford 1-(6-amino-5-ethylsulfonyl-3-pyridyl)cyclopropanecarbonitrile. LCMS (method 1): Rt=0.76 min, m/z=252 $(M+H)^+$. $^1H$ NMR (400 MHz, DMSO-d6) δ ppm: 1.05-1.19 (m, 3H), 1.39-1.51 (m, 2H), 1.61-1.73 (m, 2H), 3.27-3.34 (m, 2H)) 6.90 (br s, 2H), 7.79 (d, 1H), 8.28 (d, 1H).

Step B4: Preparation of tert-butyl N-[5-(1-cyanocyclopropyl)-3-ethylsulfonyl-2-pyridyl]carbamate (Intermediate I-10)

(I-10)

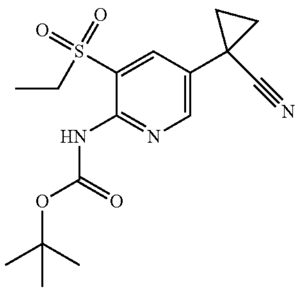

To a 0° C. cooled solution of 1-(6-amino-5-ethylsulfonyl-3-pyridyl)cyclopropanecarbonitrile (Intermediate I-9 prepared as described above) (4.8 g, 19 mmol) in N,N-dimethylformamide (50 mL) was added sodium hydride (1.8 g, 44 mmol, 60 mass %). After stirring for 60 minutes at 0° C., a solution of tert-butoxycarbonyl tert-butyl carbonate (5 g, 23 mmol) in N,N-dimethylformamide (15 mL) was added to the mixture. Additional N,N-dimethylformamide (10 mL) was added to the reaction mass and stirring continued at room temperature overnight. The reaction mass was quenched with ice water and the product extracted with ethyl acetate (3×50 mL). The combined organic layers were washed with water (50 mL) and brine (50 mL), dried over sodium sulfate, filtered and concentrated in vacuo to afford tert-butyl N-[5-(1-cyanocyclopropyl)-3-ethylsulfonyl-2-pyridyl]carbamate as yellow solid. The crude was used as such for next step. LCMS (method 1): Rt=0.97 min, m/z=296 $[(M+H)^+-56]$.

Step C1: Preparation of ethyl 6-[[tert-butoxycarbonyl-[5-(1-cyanocyclopropyl)-3-ethylsulfonyl-2-pyridyl]amino]methyl]-2,2-difluoro-1,3-benzodioxole-5-carboxylate (Intermediate I-11)

(I-11)

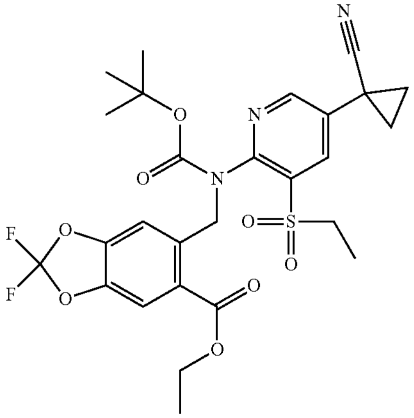

To solution of tert-butyl N-[5-(1-cyanocyclopropyl)-3-ethylsulfonyl-2-pyridyl]carbamate (Intermediate I-10 prepared as described above) (0.17 g, 0.47 mmol) in acetonitrile (10 mL) were added ethyl 6-(bromomethyl)-2,2-difluoro-1,3-benzodioxole-5-carboxylate (Intermediate I-6 prepared as described above) (0.16 g, 0.47 mmol) and cesium carbonate (0.23 g, 0.70 mmol). The reaction mixture was heated at 50° C. for 12 hours. The reaction mass was diluted with water and the product extracted with ethyl acetate. The organic layer was washed twice with water, then brine, dried over sodium sulfate, filtered and concentrated in vacuo. The crude was purified by combiflash (silica gel, 10 to 50% ethyl acetate in cyclohexane) to afford ethyl 6-[[tert-butoxycarbonyl-[5-(1-cyanocyclopropyl)-3-ethylsulfonyl-2-pyridyl]amino]methyl]-2,2-difluoro-1,3-benzodioxole-5-carboxylate as gummy mass. LCMS (method 2): Rt=1.69 min, m/z=594 $(M+H)^+$.

Step C2: Preparation of ethyl 6-[[[5-(1-cyanocyclopropyl)-3-ethylsulfonyl-2-pyridyl]amino]methyl]-2,2-difluoro-1,3-benzodioxole-5-carboxylate (Intermediate I-12)

(I-12)

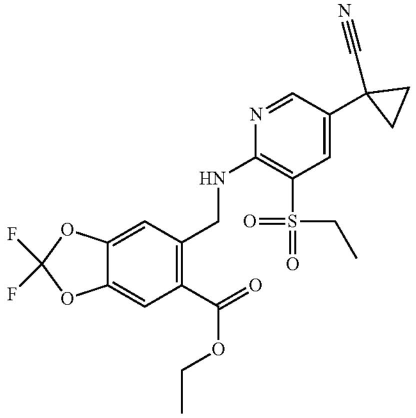

A solution of ethyl 6-[[tert-butoxycarbonyl-[5-(1-cyanocyclopropyl)-3-ethylsulfonyl-2-pyridyl]amino]methyl]-2,2-difluoro-1,3-benzodioxole-5-carboxylate (Intermediate I-11 prepared as described above) (0.215 g, 0.34 mmol) in trifluoroacetic acid (3 mL) was stirred for 3 hours. After completion, the reaction mass was neutralized with an aqueous sodium bicarbonate solution. The aqueous layer was extracted with ethyl acetate (2×), the combined organic layers were dried over sodium sulfate, filtered and concentrated in vacuo to afford ethyl 6-[[[5-(1-cyanocyclopropyl)-3-ethylsulfonyl-2-pyridyl]amino]methyl]-2,2-difluoro-1,3-benzodioxole-5-carboxylate. The crude was used as such for next step. LCMS (method 2): Rt=1.65 min, m/z=494 $(M+H)^+$.

Step C3: 6-[[[5-(1-cyanocyclopropyl)-3-ethylsulfonyl-2-pyridyl]amino]methyl]-2,2-difluoro-1,3-benzodioxole-5-carboxylic acid (Intermediate I-13)

(I-13)

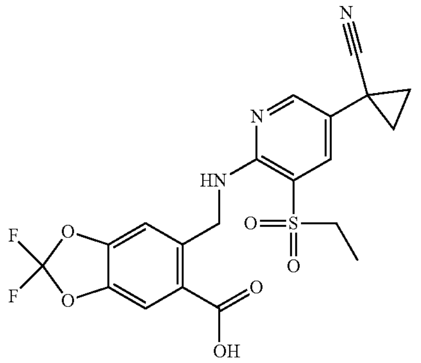

To solution of ethyl 6-[[[5-(1-cyanocyclopropyl)-3-ethylsulfonyl-2-pyridyl]amino]methyl]-2,2-difluoro-1,3-benzodioxole-5-carboxylate (Intermediate I-12 prepared as described above) (0.17 g, 0.32 mmol) in tetrahydrofuran (10 mL) was added a solution of lithium hydroxide monohydrate (0.054 g, 1.30 mmol) in water (2 mL) at 10° C. The reaction mixture was stirred at room temperature for 12 hours. Additional lithium hydroxide monohydrate (0.054 g, 1.30 mmol) was added and the reaction mass heated at 50° C. for 3 hours. After completion, the reaction mass was concentrated in vacuo, the residue acidified with an aqueous 1N hydrochloric acid solution, and the product extracted with ethyl acetate. The organic layer was washed twice with water and brine, dried over sodium sulfate, filtered and concentrated in vacuo. The crude was used as such for next step. LCMS (method 2): Rt=1.49 min, m/z=466 $(M+H)^+$.

Step C4: Preparation of 1-[6-(2,2-difluoro-7-oxo-5H-[1,3]dioxolo[4,5-f]isoindol-6-yl)-5-ethylsulfonyl-3-pyridyl]cyclopropanecarbonitrile (Compound P1)

(P1)

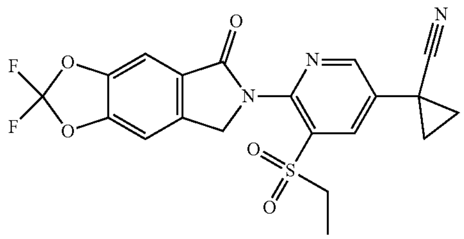 [SMILES: CCS(=O)(=O)c1cc(C2(C#N)CC2)cnc1N1Cc2cc3c(cc2C1=O)OC(F)(F)O3]

To a 0° C. cooled solution of 6-[[[5-(1-cyanocyclopropyl)-3-ethylsulfonyl-2-pyridyl]amino]methyl]-2,2-difluoro-1,3-benzodioxole-5-carboxylic acid (Intermediate I-13 prepared as described above) (0.16 g, 0.32 mmol) in pyridine (1 mL) was added phosphorus oxychloride (0.09 mL, 0.97 mmol). The reaction mixture was allowed to reach room temperature and stirred for 2 hours under nitrogen atmosphere. The reaction mass was acidified with an aqueous 2N hydrochloric acid (15 mL) solution and the product extracted with ethyl acetate (2×30 mL). The combined organic layers were dried over sodium sulfate, filtered and concentrated in vacuo. The crude compound was purified by combiflash (silica gel, 50% ethyl acetate in cyclohexane) to afford 1-[6-(2,2-difluoro-7-oxo-5H-[1,3]dioxolo[4,5-f]isoindol-6-yl)-5-ethylsulfonyl-3-pyridyl]cyclopropanecarbonitrile (compound P1) as a white solid. LCMS (method 1): Rt=1.08 min, m/z=448 $(M+H)^+$. $^1H$ NMR (400 MHz, $CDCl_3$) δ ppm: 1.38 (t, 3H), 1.55-1.63 (m, 2H), 1.93-2.01 (m, 2H), 3.54 (q, 2H), 4.98 (s, 2H), 7.23 (s, 1H), 7.57 (s, 1H), 8.19 (d, 1H), 8.84 (d, 1H).

Example P2: Preparation of 1-[4-[4-(2,2-difluoro-7-oxo-5H-[1,3]dioxolo[4,5-f]isoindol-6-yl)-5-ethylsulfonyl-1-methyl-imidazol-2-yl]phenyl]cyclooropanecarbonitrile (Compound P2)

(P2)

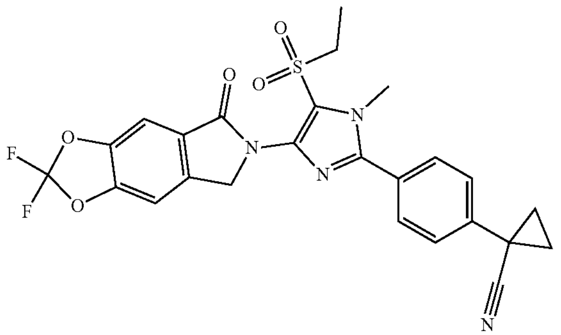

Step 1: Preparation of ethyl 1-methylimidazole-4-carboxylate (Intermediate I-14)

(I-14)

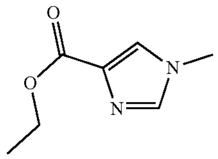

To a solution of 1-methylimidazole-4-carboxylic acid (20.0 g, 159 mmol) in ethanol (200 mL) was added N,N-dimethylformamide (1.23 mL, 15.9 mmol) in one portion via syringe. The mixture was cooled to 0-5° C., then thionyl chloride (34.7 mL, 476 mmol) was added dropwise over a period of 15 minutes at 0-5° C. The cooling was removed, and the mixture stirred from 0-5° C. to 24° C. for one hour, then at 80° C. for 6 hours under nitrogen atmosphere. After completion, the reaction mass was concentrated in vacuo, quenched with an aqueous saturated sodium bicarbonate solution (100 mL) and the product extracted with ethyl acetate (3×200 mL). The combined organic layers were washed with brine, dried over sodium sulfate, filtered and concentrated in vacuo to afford ethyl 1-methylimidazole-4-carboxylate. This material was used as such in the next step. LCMS (method 2): Rt=0.31 min, m/z=155 $(M+H)^+$.

Step 2: Preparation of ethyl 2-bromo-1-methyl-imidazole-4-carboxylate (Intermediate I-15)

(I-15)

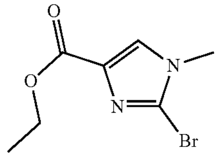

To a solution of ethyl 1-methylimidazole-4-carboxylate (Intermediate I-14 prepared as described above) (20.0 g, 130 mmol) in tetrahydrofuran (200 mL) were added N-bromosuccinimide (23.6 g, 130 mmol) and potassium phosphate tribasic (29.0 g, 130 mmol) and the mixture was stirred at room temperature for 16 hours under nitrogen atmosphere. The reaction mixture was diluted with water (100 mL) and extracted with ethyl acetate (3×100 mL). The organic layers were dried over sodium sulfate, filtered and concentrated in vacuo. The crude was purified by combiflash (silica gel, 35% ethyl acetate in cyclohexane) to afford ethyl 2-bromo-1-methyl-imidazole-4-carboxylate as a white solid. LCMS (method 2): Rt=0.85 min, m/z=233/235 $(M+H)^+$. $^1H$ NMR (400 MHz, $CDCl_3$) δ ppm: 1.37 (t, 3H), 3.68 (s, 3H), 4.36 (q, 2H), 7.64 (s, 1H).

Step 3: Preparation of ethyl 2-bromo-5-ethylsulfanyl-1-methyl-imidazole-4-carboxylate (Intermediate I-16)

(I-16)

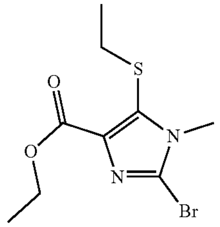

To a solution of N-isopropylpropan-2-amine (2.4 mL, 17 mmol) in tetrahydrofuran (20 mL) was added n-butyllithium (2.0 mol/L in cyclohexane, 10 mL, 20 mmol) at −78° C. under nitrogen atmosphere. The resulting solution was stirred at −78° C. for 30 minutes. Then the solution was warmed to 0° C. and stirred at 0° C. for 30 minutes. Then, this freshly prepared solution of lithium diisopropylamide was added dropwise to a solution of ethyl 2-bromo-1-methyl-imidazole-4-carboxylate (Intermediate I-15 prepared as described above) (2.5 g, 11 mmol) and (ethyldisulfanyl)ethane (2.6 g, 21 mmol) in tetrahydrofuran (25 mL) at −78° C. The resulting solution was stirred at −78° C. for 30 minutes. The reaction mixture was quenched with an aqueous saturated ammonium chloride solution and the product extracted with ethyl acetate (2×100 mL). The combined organic layers were washed with brine, dried over sodium sulfate, filtered and concentrated in vacuo. The crude was purified by combiflash (silica gel, 20% ethyl acetate in cyclohexane) to afford pure ethyl 2-bromo-5-ethylsulfanyl-1-methyl-imidazole-4-carboxylate as a brown thick oil. LCMS (method 2): Rt=1.36 min, m/z=293/295 $(M+H)^+$. $^1H$ NMR (400 MHz, $CDCl_3$) δ ppm: 1.21 (t, 3H), 1.40 (t, 3H), 2.92 (q, 2H), 3.71 (s, 3H), 4.40 (q, 2H).

Step 4: Preparation of ethyl 2-bromo-5-ethylsulfonyl-1-methyl-imidazole-4-carboxylate (Intermediate I-17)

(I-17)

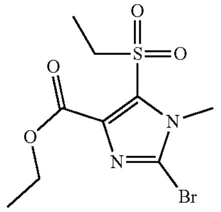

To 0° C. cooled solution of ethyl 2-bromo-5-ethylsulfanyl-1-methyl-imidazole-4-carboxylate (Intermediate I-16 prepared as described above) (4.50 g, 15.3 mmol) in acetonitrile (45 mL) was added 3-chlorobenzenecarboperoxoic acid (8.32 g, 33.8 mmol, 70 mass %) at 0° C. The reaction mixture was stirred at room temperature for 4 hours. After completion, the reaction mass was quenched with an aqueous 2N sodium hydroxide (50 mL) and water (50 mL), and the product extracted with ethyl acetate (2×100 mL). The combined organic layers were washed with brine (50 mL), dried over sodium sulfate, filtered and concentrated in vacuo. The crude was purified by combiflash (silica gel, 30% ethyl acetate in cyclohexane) to afford ethyl 2-bromo-5-ethylsulfonyl-1-methyl-imidazole-4-carboxylate as a thick oil. LCMS (method 2): Rt=1.31 min, m/z=325/327 $(M+H)^+$. $^1H$ NMR (400 MHz, $CDCl_3$) δ ppm: 1.35-1.44 (m, 6H), 3.67 (q, 2H), 3.97 (s, 3H), 4.43 (q, 2H).

Step 5: Preparation of ethyl 2-[4-(1-cyanocyclopropyl)phenyl]-5-ethylsulfonyl-1-methyl-imidazole-4-carboxylate (Intermediate I-18)

(I-18)

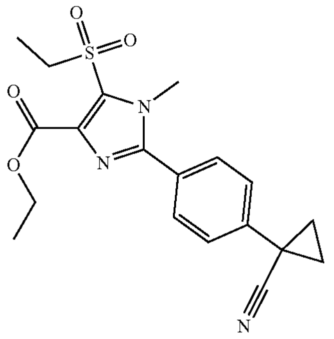

In a microwave vial, a stirred solution of ethyl 2-bromo-5-ethylsulfonyl-1-methyl-imidazole-4-carboxylate (Intermediate I-17 prepared as described above) (0.50 g, 1.53 mmol) in 1,4-dioxane (3 mL) were added cesium carbonate (1.50 g, 4.61 mmol) and 1-[4-(4,4,5,5-tetramethyl-1,3,2-dioxaborolan-2-yl)phenyl]cyclopropanecarbonitrile (CAS 1206641-31-7) (1.24 g, 4.61 mmol) at room temperature. The reaction mass was degassed with nitrogen for 15 minutes, then tetrakis(triphenylphosphine)palladium(0) (0.18 g, 0.15 mmol) was added under nitrogen atmosphere. The vial was sealed and heated at 110° C. for 60 minutes under microwave irradiation. The reaction mixture was quenched with water (50 mL) and the product extracted with ethyl acetate (2×50 mL). The combined organic layers were dried over dried over sodium sulfate, filtered and concentrated in vacuo. The crude was purified by combiflash (silica gel, 25% ethyl acetate in cyclohexane) to afford ethyl 2-[4-(1-cyanocyclopropyl)phenyl]-5-ethylsulfonyl-1-methyl-imidazole-4-carboxylate as gummy mass. LCMS (method 2): Rt=1.41 min, m/z=388 $(M+H)^+$.

Step-6: Preparation of 2-[4-(1-cyanocyclopropyl)phenyl]-5-ethylsulfonyl-1-methyl-imidazole-4-carboxylic acid (Intermediate I-19)

(I-19)

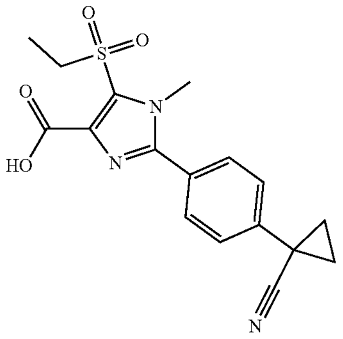

To a solution of ethyl 2-[4-(1-cyanocyclopropyl)phenyl]-5-ethylsulfonyl-1-methyl-imidazole-4-carboxylate (Intermediate I-18 prepared as described above) (1.00 g, 2.58 mmol) in tetrahydrofuran (15 mL) was added a solution of lithium hydroxide monohydrate (0.162 g, 3.87 mmol) in water (4 mL) at room temperature, then stirred for 10 hours. Additional lithium hydroxide monohydrate (0.162 g, 3.87 mmol) was added and stirring continued at 45° C. for 1 hour. After completion, the reaction mixture was quenched with water (50 mL), acidified with an aqueous 2N hydrochloric acid (20 mL) solution, and the product extracted with ethyl acetate (3×50 mL). The combined organic layers were washed with brine (30 mL), dried over anhydrous sodium sulfate, filtered and concentrated in vacuo. The crude was washed with n-pentane (2×10 mL) to afford pure 2-[4-(1-cyanocyclopropyl)phenyl]-5-ethylsulfonyl-1-methyl-imidazole-4-carboxylic acid as a white solid. LCMS (method 1): Rt=0.94 min, m/z=360 $(M+H)^+$.

Step-7: Preparation of tert-butyl N-[2-[4-(1-cyanocyclopropyl)phenyl]-5-ethylsulfonyl-1-methyl-imidazol-4-yl]carbamate (Intermediate I-20)

(I-20)

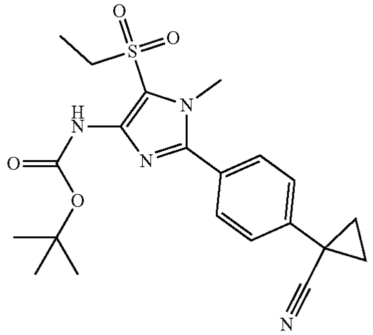

To a solution of 2-[4-(1-cyanocyclopropyl)phenyl]-5-ethylsulfonyl-1-methyl-imidazole-4-carboxylic acid (Intermediate I-19 prepared as described above) (0.80 g, 2.22 mmol) in tert-butanol (16 mL) was added triethylamine (0.36 g, 3.56 mmol) at room temperature. The mixture was heated to 90° C. and stirred for 10 minutes. Diphenylphoshoryl azide (1.00 g, 3.56 mmol) was added dropwise over a period of 15 minutes and the resulting reaction mixture was stirred at 90° C. for 40 minutes. The reaction mass was allowed to cool to room temperature, then quenched with ice cold water (30 mL), diluted with brine (20 mL), and the product extracted with ethyl acetate (3×70 mL). The combined organic layers were dried over sodium sulfate, filtered and concentrated in vacuo. The crude was purified by combiflash (silica gel, 60% ethyl acetate in cyclohexane) to afford tert-butyl N-[2-[4-(1-cyanocyclopropyl)phenyl]-5-ethylsulfonyl-1-methyl-imidazol-4-yl]carbamate as a white solid. LCMS (method 1): Rt=1.08 min, m/z=429 $(M-H)^-$. $^1H$ NMR (400 MHz, $CDCl_3$) δ ppm: 1.37-1.44 (m, 3H), 1.44-1.56 (m, 11H), 1.73-1.91 (m, 2H), 3.25 (q, 2H), 3.81 (s, 3H), 7.39 (d, 2H), 7.63 (d, 2H), 7.83 (s, 1H).

Step-8: Preparation of ethyl 6-[[tert-butoxycarbonyl-[2-[4-(1-cyanocyclopropyl)phenyl]-5-ethylsulfonyl-1-methyl-imidazol-4-yl]amino]methyl]-2,2-difluoro-1,3-benzodioxole-5-carboxylate (Intermediate I-21)

(I-21)

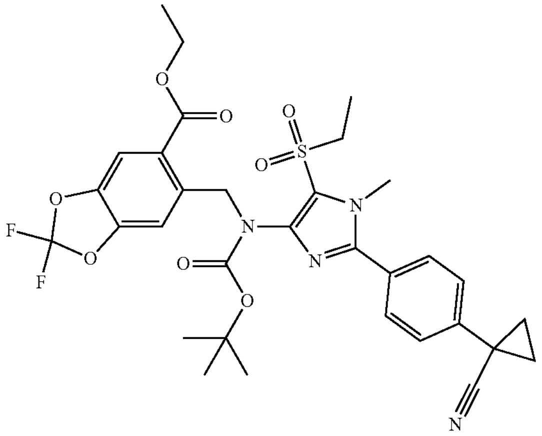

To solution of tert-butyl N-[2-[4-(1-cyanocyclopropyl)phenyl]-5-ethylsulfonyl-1-methyl-imidazol-4-yl]carbamate (Intermediate I-20 prepared as described above) (0.21 g, 0.46 mmol) in acetonitrile (10 mL) were added ethyl 6-(bromomethyl)-2,2-difluoro-1,3-benzodioxole-5-carboxylate (Intermediate I-6 prepared as described above) (0.17 g, 0.50 mmol) and cesium carbonate (0.22 g, 0.69 mmol) at room temperature. The reaction mass was heated at 50° C. for 12 hours, then diluted with water and the product extracted with ethyl acetate. The organic layer was washed with water followed by brine, dried over sodium sulfate, filtered and concentrated in vacuo. The crude was purified by combiflash (silica gel, 10 to 50% ethyl acetate in cyclohexane) to afford ethyl 6-[[tert-butoxycarbonyl-[2-[4-(1-cyanocyclopropyl)phenyl]-5-ethylsulfonyl-1-methyl-imidazol-4-yl]amino]methyl]-2,2-difluoro-1,3-benzodioxole-5-carboxylate as gummy mass. LCMS (method 1): Rt=1.29 min, m/z=617 $[(M+H)^+-56]$.

Step-9: Preparation of ethyl 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylate (Intermediate I-22)

(I-22)

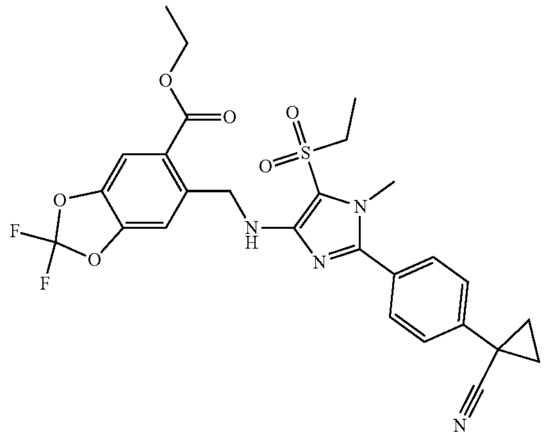

A solution of ethyl 6-[[tert-butoxycarbonyl-[2-[4-(1-cyanocyclopropyl)phenyl]-5-ethylsulfonyl-1-methyl-imidazol-4-yl]amino]methyl]-2,2-difluoro-1,3-benzodioxole-5-carboxylate (Intermediate I-21 prepared as described above) (0.23 g, 0.32 mmol) in trifluoroacetic acid (2 mL) was stirred for 2 hours at room temperature. After completion, the reaction mass was neutralized with an aqueous sodium bicarbonate solution, and the product extracted with ethyl acetate (2×). The combined organic layers were dried over sodium sulfate, filtered and concentrated in vacuo to afford ethyl 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylate. The crude was used as such for next step. $^1$H NMR (400 MHz, $CDCl_3$) δ ppm: 1.35-1.48 (m, 6H), 1.51-1.57 (m, 2H), 1.86-1.90 (m, 2H), 3.22 (q, 2H), 3.81 (s, 3H), 4.43 (q, 2H), 4.86 (s, 2H), 5.26 (br s, 1H), 7.48-7.52 (m, 3H), 7.58 (d, 2H), 7.77 (s, 1H).

Step-10: Preparation of 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylic acid (Intermediate I-23)

(I-23)

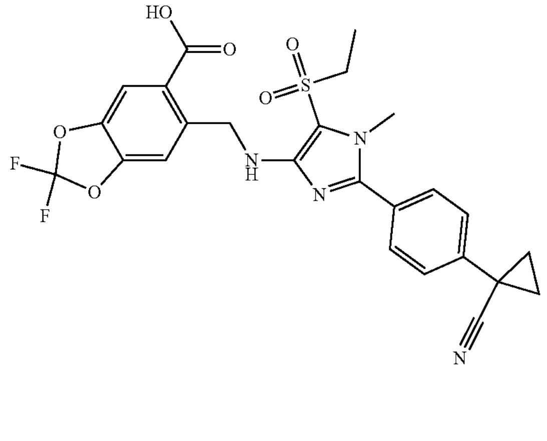

To solution of ethyl 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylate (Intermediate I-22 prepared as described above) (0.19 g, 0.31 mmol) in tetrahydrofuran (6 mL) was added a solution of lithium hydroxide monohydrate (0.055 g, 1.26 mmol) in water (2 mL) at 10° C. The reaction mixture was stirred at room temperature for 1 hour. Additional lithium hydroxide monohydrate (0.054 g, 1.30 mmol) was added and stirring continued at 50° C. for 3 hours. After completion, the reaction mass was concentrated in vacuo, the residue acidified with an aqueous 1N hydrochloric acid solution, and the product extracted with ethyl acetate. The organic layer was washed with water (2×) followed by brine, dried over sodium sulfate, filtered and concentrated in vacuo to afford 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylic acid. The crude was used as such for next step. LCMS (method 1): Rt=1.09 min, m/z=545 (M+H)+.

Example P2: Preparation of 1-[4-[4-(2,2-difluoro-7-oxo-5H-[1,3]dioxolo[4,5-f]isoindol-6-yl)-5-ethylsulfonyl-1-methyl-imidazol-2-yl]phenyl]cyclopropanecarbonitrile (Compound P2)

(P2)

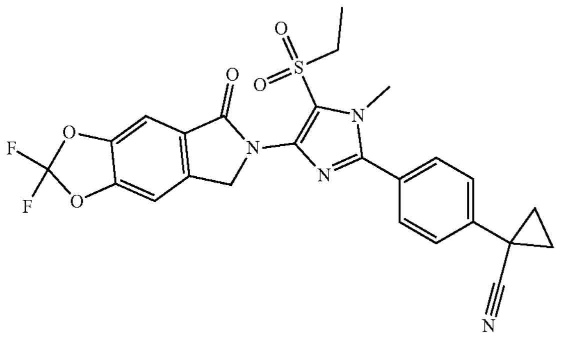

To a 0° C. cooled solution of 6-[[[2-[4-(1-cyanocyclopropyl)phenyl]-5-ethylsulfonyl-1-methyl-imidazol-4-yl]amino]methyl]-2,2-difluoro-1,3-benzodioxole-5-carboxylic acid (Intermediate I-23 prepared as described above) (0.18 g, 0.31 mmol) in pyridine (1 mL) was added phosphorus oxychloride (0.05 mL, 0.62 mmol). The reaction mixture was allowed to come at room temperature and stirred for 2 hours under nitrogen atmosphere. The reaction mass was acidified with an aqueous 2N hydrochloric acid (15 mL) solution, and the product extracted with ethyl acetate (2×30 mL). The combined organic layers were dried over sodium sulfate, filtered and concentrated in vacuo. The crude compound was purified by combiflash (silica gel, 50% ethyl acetate in cyclohexane) to afford 1-[4-[4-(2,2-difluoro-7-oxo-5H-[1,3]dioxolo[4,5-f]isoindol-6-yl)-5-ethylsulfonyl-1-methyl-imidazol-2-yl]phenyl]cyclopropane-carbonitrile (compound P2) as a white solid. LCMS (method 1): Rt=1.10 min, m/z=527 (M+H)+. $^{1}H$ NMR (400 MHz, $CDCl_3$) δ ppm: 1.46-1.56 (m, 5H), 1.83-1.89 (m, 2H), 3.63-3.72 (m, 2H), 3.95 (s, 3H), 4.92 (s, 2H), 7.21 (s, 1H), 7.47 (m, 2H), 7.59 (s, 1H), 7.65 (m, 2H).

Example P8: Preparation of 6-[3-ethylsulfonyl-5-(2,2,2-trifluoroethoxy)-2-pyridyl]-2,2-difluoro-5H-[1,3]dioxolo[4,5-f]isoindol-7-one (Compound P8)

(P8)

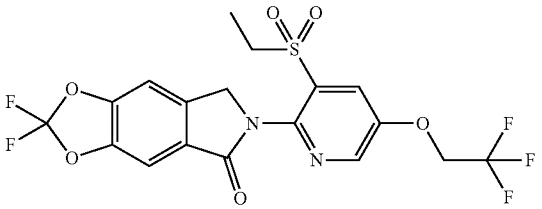

Compound P8 was prepared in analogy to compound P1 as described above using intermediate I-6 (described above) and intermediate I-65 (described below) as starting materials. LCMS (method 1): Rt=1.16 min, m/z=481 $(M+H)^+$.

Example P3: Preparation of 6-[2-(3-cyclopropyl-4,5-dihydroisoxazol-5-yl)-5-ethylsulfonyl-1-methyl-imidazol-4-yl]-2,2-difluoro-5H-[1,3]dioxolo[4,5-f]isoindol-7-one (Compound P3)

(P3)

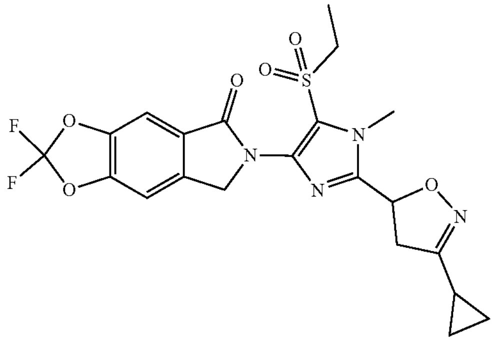

Compound P3 was prepared in analogy to compound P2 as described above using intermediate I-6 (described above) and intermediate I-27 (described below) as starting materials. LCMS (method 1): Rt=1.10 min. m/z=495 $(M+H)^+$.

Example P10: Preparation of 6-(6-cyclopropyl-3-ethylsulfonyl-2-pyridyl)-2,2-difluoro-5H-[1,3]dioxolo[4,5-f]isoindol-7-one (Compound P10)

(P10)

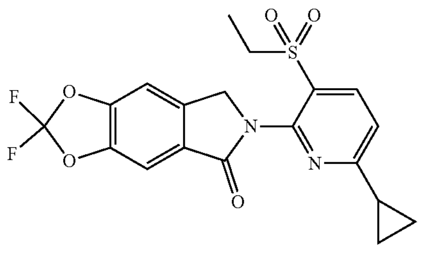

Compound P10 was prepared in analogy to compound P1 as described above using intermediate I-6 (described above) and intermediate I-59 (described below) as starting materials. LCMS (method 1): Rt=1.14 min, m/z=423 $(M+H)^+$.

Example P6: Preparation of 6-[5-ethylsulfonyl-1-methyl-2-(2,2,2-trifluoroethoxy)imidazol-4-yl]-2,2-difluoro-5H-[1,3]dioxolo[4,5-f]isoindol-7-one (Compound P6)

(P6)

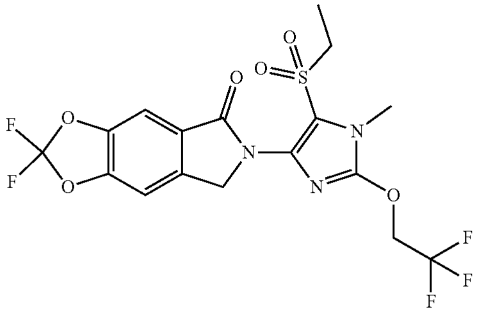

Compound P6 was prepared in analogy to compound P2 as described above using intermediate I-6 (described above) and intermediate I-33 (described below) as starting materials. LCMS (method 1): Rt=1.12 min, m/z=484 $(M+H)^+$.

Example P12: Preparation of 6-[5-(2,2-difluoropropoxy)-3-ethylsulfonyl-2-pyridyl]-2,2-difluoro-5H-[1,3]dioxolo[4,5-f]isoindol-7-one (Compound P12)

(P12)

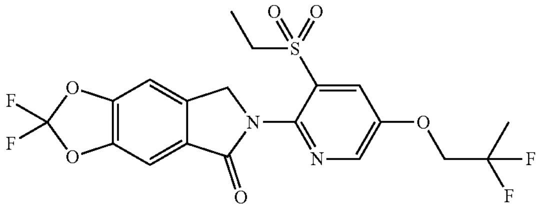

Compound P12 was prepared in analogy to compound P1 as described above using intermediate I-6 (described above) and intermediate I-67 (described below) as starting materials. LCMS (method 1): Rt=1.12 min, m/z=477 $(M+H)^+$.

Example P21: Preparation of 6-[2-(3-chloropyrazol-1-yl)-5-ethylsulfonyl-1-methyl-imidazol-4-yl]-2,2-difluoro-5H-[1,3]dioxolo[4,5-f]isoindol-7-one (Compound P21)

(P21)

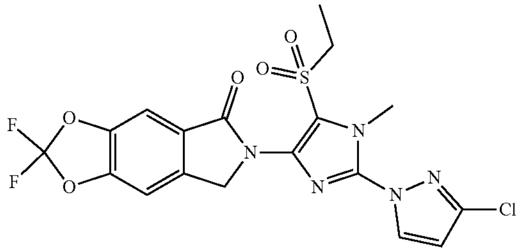

Compound P21 was prepared in analogy to compound P2 as described above using intermediate I-6 (described above) and intermediate I-45 (described below) as starting materials. LCMS (method 1): Rt=1.08 min, m/z=486/488 $(M+H)^+$.

Example P23: Preparation of 6-[5-(1,1-difluoroethyl)-3-ethylsulfonyl-2-pyridyl]-2,2-difluoro-5H-[1,3]dioxolo[4,5-f]isoindol-7-one (Compound P23)

(P23)

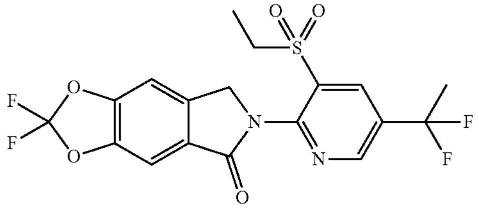

Compound P23 was prepared in analogy to compound P1 as described above using intermediate I-6 (described above) and intermediate I-63 (described below) as starting materials. LCMS (method 1): Rt=1.12 min, m/z=447 $(M+H)^+$.

Example P26: Preparation of 6-[2-(3-cyclopropylisoxazol-5-yl)-5-ethylsulfonyl-1-methyl-imidazol-4-yl]-2,2-difluoro-5H-[1,3]dioxolo[4,5-f]isoindol-7-one (Compound P26)

(P26)

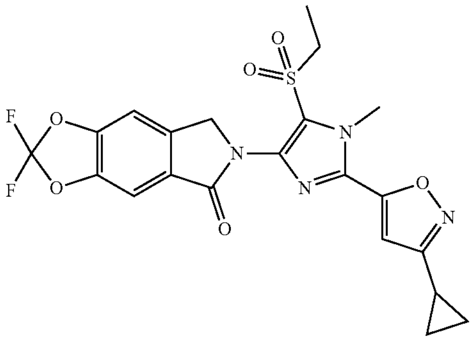

A suspension of 6-[2-(3-cyclopropyl-4,5-dihydroisoxazol-5-yl)-5-ethylsulfonyl-1-methyl-imidazol-4-yl]-2,2-difluoro-5H-[1,3]dioxolo[4,5-f]isoindol-7-one (compound P3 prepared as described above) (330 mg, 0.634 mmol) and manganese(IV) oxide (334 mg, 3.804 mmol) in toluene (5 mL) was heated at 110° C. for 5 hours. The reaction mixture was diluted with ethyl acetate and water, the layers were separated, the organic phase washed with water (2×) followed by brine, dried over sodium sulfate, filtered and concentrated in vacuo. The residue was purified by combiflash (silica gel, 50-100% ethyl acetate in cyclohexane) to afford pure 6-[2-(3-cyclopropylisoxazol-5-yl)-5-ethylsulfonyl-1-methyl-imidazol-4-yl]-2,2-difluoro-5H-[1,3]dioxolo[4,5-f]isoindol-7-one (compound P26) a solid. LCMS (method 1): Rt=1.14 min. m/z=493 $(M+H)^+$.

Example P25: Preparation of 2-[[6-(2,2-difluoro-7-oxo-5H-[1,3]dioxolo[4,5-f]isoindol-6-yl)-5-ethylsulfonyl-3-pyridinyl]oxy]-2-methyl-propanenitrile (Compound P25)

(P25)

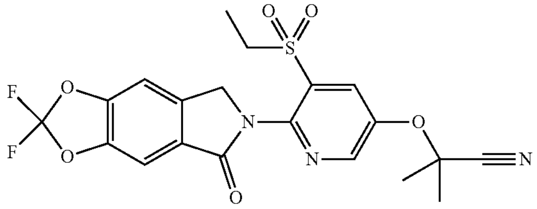

Compound P25 was prepared in analogy to compound P1 as described above using intermediate I-6 (described above) and intermediate I-53 (described below) as starting materials. LCMS (method 1): Rt=1.14 min, m/z=466 $(M+H)^+$.

TABLE P

Examples of compounds of formula (I)

| No. | IUPAC name | Structures | $R_t$ (min) | LCMS [M + H]$^+$ (measured) | LCMS Method | Mp (° C.) |
|---|---|---|---|---|---|---|
| P1 | 1-[6-(2,2-difluoro-7-oxo-5H-[1,3]dioxolo[4,5-f]isoindol-6-yl)-5-ethylsulfonyl-3-pyridyl]cyclopropanecarbonitrile | 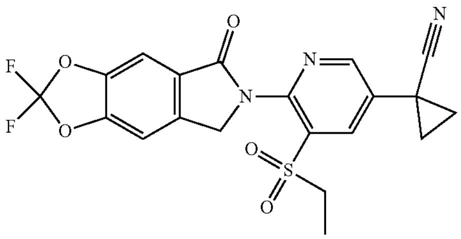 | 1.08 | 448 | 1 | 209-212 |
| P2 | 1-[4-[4-(2,2-difluoro-7-oxo-5H-[1,3]dioxolo[4,5-f]isoindol-6-yl)-5-ethylsulfonyl-1-methyl-imidazol-2-yl]phenyl]cyclopropanecarbonitrile | 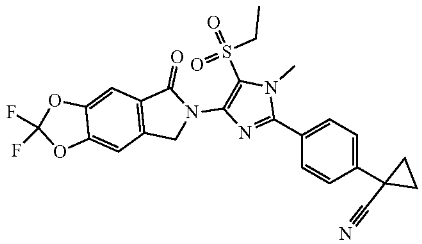 [SMILES: CCS(=O)(=O)c1c(N2Cc3cc4c(cc3C2=O)OC(F)(F)O4)nc(-c2ccc(C3(C#N)CC3)cc2)n1C] | 1.10 | 527 | 1 | 150-154 |

TABLE P-continued

Examples of compounds of formula (I)

| No. | IUPAC name | Structures | LCMS Rt (min) | [M + H]+ (measured) | Method | Mp (° C.) |
|---|---|---|---|---|---|---|
| P3 | 6-[2-(3-cyclopropyl-4,5-dihydroisoxazol-5-yl)-5-ethylsulfonyl-1-methyl-imidazol-4-yl]-2,2-difluoro-5H-[1,3]dioxolo[4,5-f]isoindol-7-one | 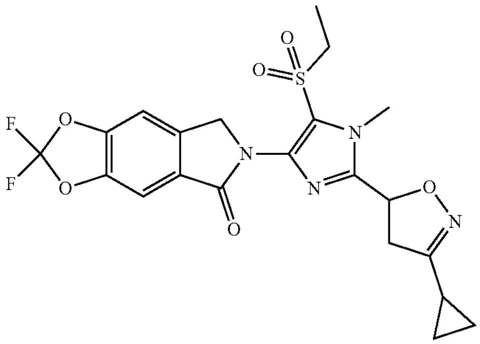 [SMILES: CCS(=O)(=O)c1c(N2Cc3cc4c(cc3C2=O)OC(F)(F)O4)nc(C2CC(C3CC3)=NO2)n1C] | 1.10 | 495 | 1 | 190-193 |
| P4 | 6-[2-[1-(2,2-difluoroethyl)pyrazol-4-yl]-5-ethylsulfonyl-1-methyl-imidazol-4-yl]-2,2-difluoro-5H-[1,3]dioxolo[4,5-f]isoindol-7-one | 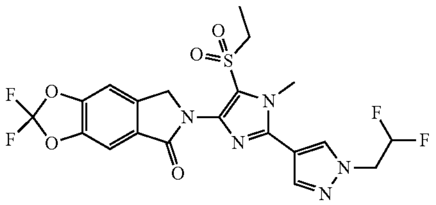 [SMILES: CCS(=O)(=O)c1c(N2Cc3cc4c(cc3C2=O)OC(F)(F)O4)nc(-c2cnn(CC(F)F)c2)n1C] | 1.05 | 516 | 1 | 216-218 |
| P5 | 1-[[4-[4-(2,2-difluoro-7-oxo-5H-[1,3]dioxolo[4,5-f]isoindol-6-yl)-5-ethylsulfonyl-1-methyl-imidazol-2-yl]pyrazol-1-yl]methyl]cyclopropanecarbonitrile | 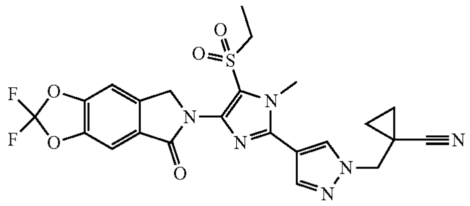 [SMILES: CCS(=O)(=O)c1c(N2Cc3cc4c(cc3C2=O)OC(F)(F)O4)nc(-c2cnn(CC3(C#N)CC3)c2)n1C] | 1.05 | 531 | 1 | 202-204 |
| P6 | 6-[5-ethylsulfonyl-1-methyl-2-(2,2,2-trifluoroethoxy)imidazol-4-yl]-2,2-difluoro-5H-[1,3]dioxolo[4,5-f]isoindol-7-one | 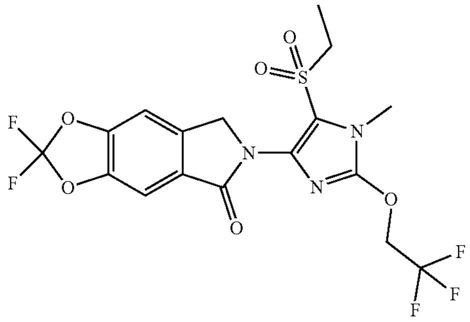 [SMILES: CCS(=O)(=O)c1c(N2Cc3cc4c(cc3C2=O)OC(F)(F)O4)nc(OCC(F)(F)F)n1C] | 1.12 | 484 | 1 | — |
| P7 | 6-(5-ethylsulfonyl-1-methyl-2-pyrimidin-5-yl-imidazol-4-yl)-2,2-difluoro-5H-[1,3]dioxolo[4,5-f]isoindol-7-one | 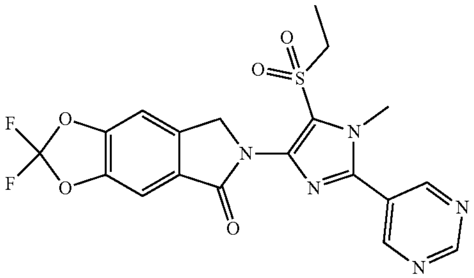 [SMILES: CCS(=O)(=O)c1c(N2Cc3cc4c(cc3C2=O)OC(F)(F)O4)nc(-c2cncnc2)n1C] | 1.02 | 463 | 1 | 130-132 |

TABLE P-continued

| Examples of compounds of formula (I) | | | | | | |
|---|---|---|---|---|---|---|
| | | | LCMS | | | |
| No. | IUPAC name | Structures | $R_t$ (min) | [M + H]$^+$ (measured) | Method | Mp (° C.) |
| P8 | 6-[3-ethylsulfonyl-5-(2,2,2-trifluoroethoxy)-2-pyridyl]-2,2-difluoro-5H-[1,3]dioxolo[4,5-f]isoindol-7-one | 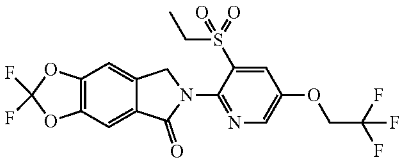 [SMILES: CCS(=O)(=O)c1cc(OCC(F)(F)F)cnc1N1Cc2cc3c(cc2C1=O)OC(F)(F)O3] | 1.16 | 481 | 1 | 181-183 |
| P9 | 6-[2-[1-(cyclopropylmethyl)pyrazol-4-yl]-5-ethylsulfonyl-1-methyl-imidazol-4-yl]-2,2-difluoro-5H-[1,3]dioxolo[4,5-f]isoindol-7-one | 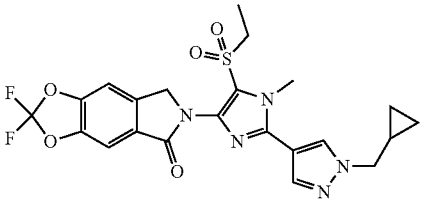 [SMILES: CCS(=O)(=O)c1c(N2Cc3cc4c(cc3C2=O)OC(F)(F)O4)nc(-c2cnn(CC3CC3)c2)n1C] | 1.06 | 506 | 1 | 170-172 |
| P10 | 6-(6-cyclopropyl-3-ethylsulfonyl-2-pyridyl)-2,2-difluoro-5H-[1,3]dioxolo[4,5-f]isoindol-7-one | 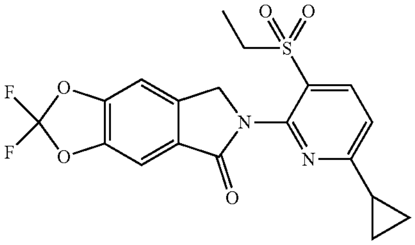 [SMILES: CCS(=O)(=O)c1ccc(C2CC2)nc1N1Cc2cc3c(cc2C1=O)OC(F)(F)O3] | 1.14 | 423 | 1 | 160-163 |
| P11 | 6-[3-ethylsulfonyl-6-(1,2,4-triazol-1-yl)-2-pyridyl]-2,2-difluoro-5H-[1,3]dioxolo[4,5-f]isoindol-7-one | 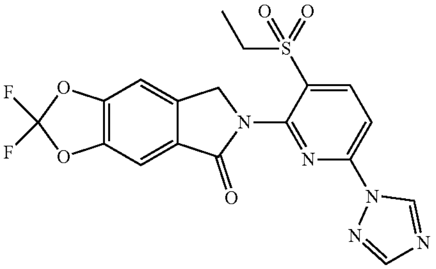 [SMILES: CCS(=O)(=O)c1ccc(-n2cncn2)nc1N1Cc2cc3c(cc2C1=O)OC(F)(F)O3] | 1.07 | 449 | 1 | 220-222 |
| P12 | 6-[5-(2,2-difluoropropoxy)-3-ethylsulfonyl-2-pyridyl]-2,2-difluoro-5H-[1,3]dioxolo[4,5-f]isoindol-7-one | 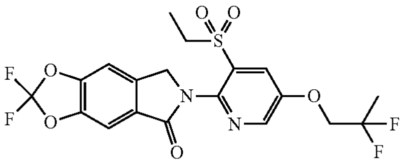 [SMILES: CCS(=O)(=O)c1cc(OCC(C)(F)F)cnc1N1Cc2cc3c(cc2C1=O)OC(F)(F)O3] | 1.12 | 477 | 1 | 184-186 |
| P13 | 6-[3-ethylsulfonyl-5-(trifluoromethyl)-2-pyridyl]-2,2-difluoro-5H-[1,3]dioxolo[4,5-f]isoindol-7-one | 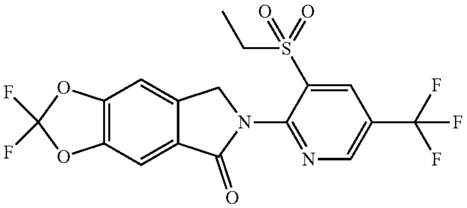 [SMILES: CCS(=O)(=O)c1cc(C(F)(F)F)cnc1N1Cc2cc3c(cc2C1=O)OC(F)(F)O3] | 1.16 | 451 | 1 | 225-227 |

TABLE P-continued

Examples of compounds of formula (I)

| No. | IUPAC name | Structures | LCMS R$_t$ (min) | LCMS [M + H]$^+$ (measured) | LCMS Method | Mp (° C.) |
|---|---|---|---|---|---|---|
| P14 | 6-[5-ethylsulfonyl-1-methyl-2-[1-(2,2,2-trifluoroethyl)pyrazol-4-yl]imidazol-4-yl]-2,2-difluoro-5H-[1,3]dioxolo[4,5-f]isoindol-7-one | 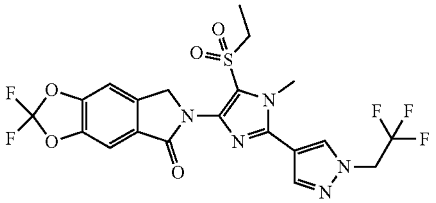 [SMILES: CCS(=O)(=O)c1c(N2Cc3cc4c(cc3C2=O)OC(F)(F)O4)nc(-c2cnn(CC(F)(F)F)c2)n1C] | 1.42 | 534 | 1 | 120-122 |
| P15 | 6-(5-ethylsulfonyl-1-methyl-2-pyrimidin-2-yl-imidazol-4-yl)-2,2-difluoro-5H-[1,3]dioxolo[4,5-f]isoindol-7-one | 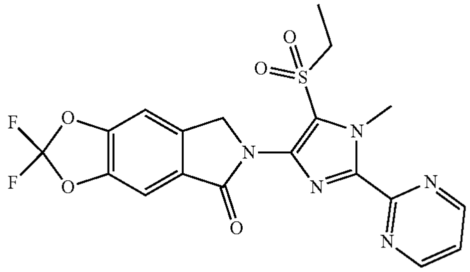 [SMILES: CCS(=O)(=O)c1c(N2Cc3cc4c(cc3C2=O)OC(F)(F)O4)nc(-c2ncccn2)n1C] | 1.01 | 464 | 1 | 206-208 |
| P16 | 6-(3-ethylsulfonyl-6-pyrimidin-2-yl-2-pyridyl)-2,2-difluoro-5H-[1,3]dioxolo[4,5-f]isoindol-7-one | 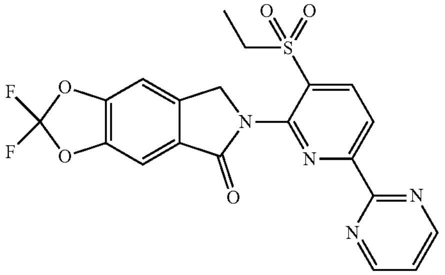 [SMILES: CCS(=O)(=O)c1ccc(-c2ncccn2)nc1N1Cc2cc3c(cc2C1=O)OC(F)(F)O3] | 1.06 | 461 | 1 | 174-176 |
| P17 | 6-[2-(1-cyclopropylpyrazol-4-yl)-5-ethylsulfonyl-1-methyl-imidazol-4-yl]-2,2-difluoro-5H-[1,3]dioxolo[4,5-f]isoindol-7-one | 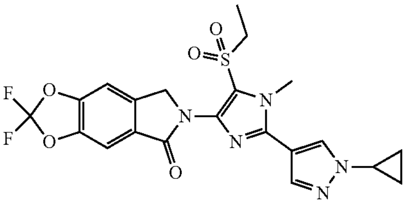 [SMILES: CCS(=O)(=O)c1c(N2Cc3cc4c(cc3C2=O)OC(F)(F)O4)nc(-c2cnn(C3CC3)c2)n1C] | 1.10 | 492 | 1 | 210-212 |
| P18 | N-[6-(2,2-difluoro-7-oxo-5H-[1,3]dioxolo[4,5-f]isoindol-6-yl)-5-ethylsulfonyl-3-pyridyl]-N-methyl-acetamide | 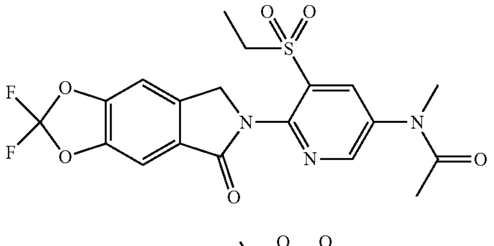 | 1.02 | 454 | 1 | 170-175 |
| P19 | 6-(5-cyclopropyl-3-ethylsulfonyl-2-pyridyl)-2,2-difluoro-5H-[1,3]dioxolo[4,5-f]isoindol-7-one | 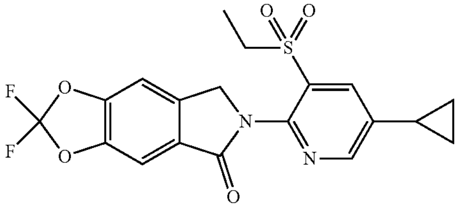 [SMILES: CCS(=O)(=O)c1cc(C2CC2)cnc1N1Cc2cc3c(cc2C1=O)OC(F)(F)O3] | 1.17 | 423 | 1 | 168-170 |

TABLE P-continued

| Examples of compounds of formula (I) | | | | | | |
|---|---|---|---|---|---|---|
| | | | LCMS | | | |
| No. | IUPAC name | Structures | $R_t$ (min) | [M + H]$^+$ (measured) | Method | Mp (° C.) |
| P20 | 6-[2-[1-(difluoromethyl)pyrazol-4-yl]-5-ethylsulfonyl-1-methyl-imidazol-4-yl]-2,2-difluoro-5H-[1,3]dioxolo[4,5-f]isoindol-7-one | 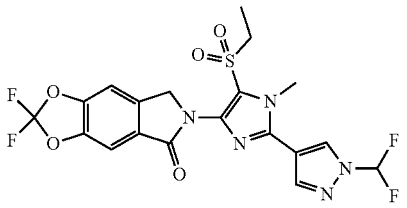 [SMILES: CCS(=O)(=O)c1c(N2Cc3cc4c(cc3C2=O)OC(F)(F)O4)nc(-c2cnn(C(F)F)c2)n1C] | 1.09 | 502 | 1 | 174-176 |
| P21 | 6-[2-(3-chloropyrazol-1-yl)-5-ethylsulfonyl-1-methyl-imidazol-4-yl]-2,2-difluoro-5H-[1,3]dioxolo[4,5-f]isoindol-7-one | 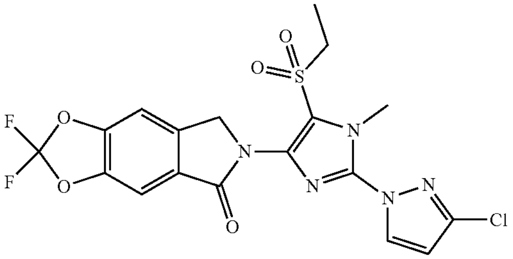 [SMILES: CCS(=O)(=O)c1c(N2Cc3cc4c(cc3C2=O)OC(F)(F)O4)nc(-n2ccc(Cl)n2)n1C] | 1.08 | 486/488 | 1 | 138-140 |
| P22 | 2-[6-(2,2-difluoro-7-oxo-5H-[1,3]dioxolo[4,5-f]isoindol-6-yl)-5-ethylsulfonyl-3-pyridyl]-2-methyl-propanenitrile | 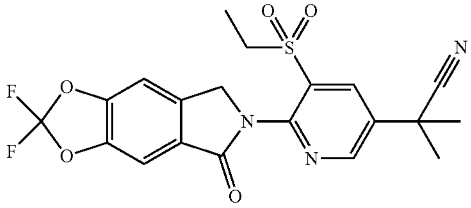 [SMILES: CCS(=O)(=O)c1cc(C(C)(C)C#N)cnc1N1Cc2cc3c(cc2C1=O)OC(F)(F)O3] | 1.09 | 450 | 1 | 202-205 |
| P23 | 6-[5-(1,1-difluoroethyl)-3-ethylsulfonyl-2-pyridyl]-2,2-difluoro-5H-[1,3]dioxolo[4,5-f]isoindol-7-one | 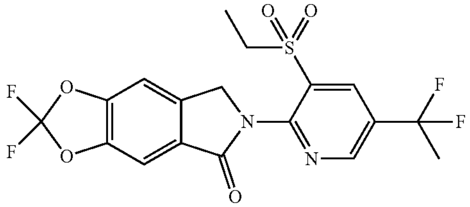 [SMILES: CCS(=O)(=O)c1cc(C(C)(F)F)cnc1N1Cc2cc3c(cc2C1=O)OC(F)(F)O3] | 1.12 | 447 | 1 | 185-187 |
| P24 | 6-(2-cyclopropyl-5-ethylsulfonyl-1-methyl-imidazol-4-yl)-2,2-difluoro-5H-[1,3]dioxolo[4,5-f]isoindol-7-one | 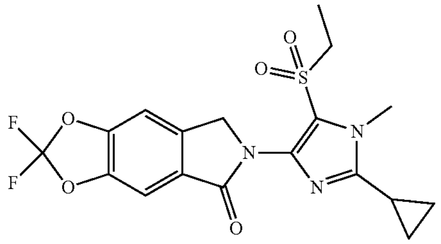 [SMILES: CCS(=O)(=O)c1c(N2Cc3cc4c(cc3C2=O)OC(F)(F)O4)nc(C2CC2)n1C] | 1.09 | 426 | 1 | 181-183 |
| P25 | 2-[[6-(2,2-difluoro-7-oxo-5H-[1,3]dioxolo[4,5-f]isoindol-6-yl)-5-ethylsulfonyl-3-pyridyl]oxy]-2-methyl-propanenitrile | 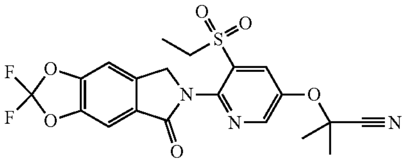 [SMILES: CCS(=O)(=O)c1cc(OC(C)(C)C#N)cnc1N1Cc2cc3c(cc2C1=O)OC(F)(F)O3] | 1.14 | 466 | 1 | 166-169 |

TABLE P-continued

Examples of compounds of formula (I)

| | | | LCMS | | | |
|---|---|---|---|---|---|---|
| No. | IUPAC name | Structures | $R_t$ (min) | $[M+H]^+$ (measured) | Method | Mp (° C.) |
| P26 | 6-[2-(3-cyclopropylisoxazol-5-yl)-5-ethylsulfonyl-1-methyl-imidazol-4-yl]-2,2-difluoro-5H-[1,3]dioxolo[4,5-f]isoindol-7-one | 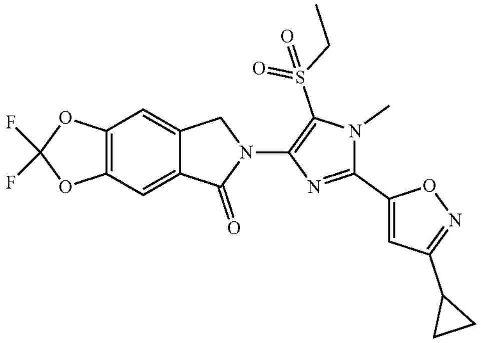 [SMILES: CCS(=O)(=O)c1c(N2Cc3cc4c(cc3C2=O)OC(F)(F)O4)nc(-c2cc(C3CC3)no2)n1C] | 1.14 | 493 | 1 | 204-207 |

Representative Preparation of Intermediates

Example I-27: Preparation of tert-butyl N-[2-(3-cyclopropyl-4,5-dihydroisoxazol-5-yl)-5-ethylsulfonyl-1-methyl-imidazol-4-yl]carbamate (Intermediate I-27)

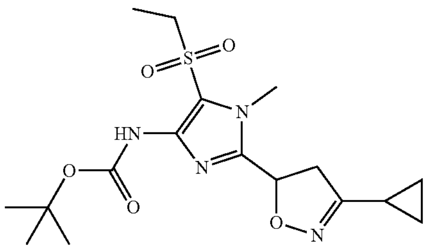

(I-27)

Step 1: Preparation of ethyl 5-ethylsulfonyl-1-methyl-2-vinyl-imidazole-4-carboxylate

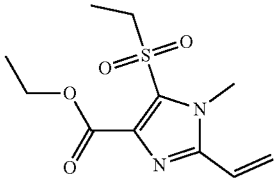 [SMILES: C=Cc1nc(C(=O)OCC)c(S(=O)(=O)CC)n1C]

To a solution of ethyl 2-bromo-5-ethylsulfonyl-1-methyl-imidazole-4-carboxylate (intermediate I-17 prepared as described in example P2 step 4) (1.00 g, 2.92 mmol) in toluene (8 mL) was added tributyl(vinyl)tin (1.08 mL, 3.50 mmol) and the solution was degassed with nitrogen for 10 minutes. Then, [1,1'-bis(diphenylphosphino)ferrocene]dichloropalladium(II) complex (0.0147 g, 0.175 mmol) was added and the reaction mixture was heated in microwave at 130° C. for 1 hour. The reaction mixture was concentrated in vacuo. The residue was dissolved in ethyl acetate, washed twice with water, then once with brine. The organic layer was dried over anhydrous sodium sulfate, filtered and concentrated in vacuo. The crude was purified by combiflash (silica gel, 50% ethyl acetate in cyclohexane) to afford ethyl 5-ethylsulfonyl-1-methyl-2-vinyl-imidazole-4-carboxylate as a brown oil. LCMS (method 2): Rt=0.87 min, m/z=273 $(M+H)^+$. $^1H$ NMR (400 MHz, $CDCl_3$) δ ppm: 6.61-6.69 (m, 1H) 6.52-6.48 (m, 1H) 5.79 (dd, J=11.01, 1.25 Hz, 1H) 4.46 (q, 2H) 3.96 (s, 3H) 3.66 (q, 2H) 1.36-1.47 (m, 6H).

Step 2: Preparation of ethyl 2-(3-cyclopropyl-4,5-dihydroisoxazol-5-yl)-5-ethylsulfonyl-1-methyl-imidazole-4-carboxylate

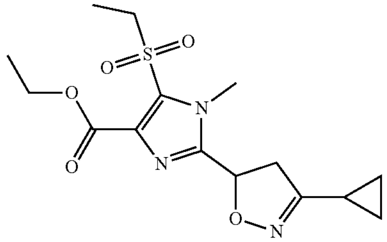 [SMILES: CCOC(=O)c1nc(C2CC(C3CC3)=NO2)n(C)c1S(=O)(=O)CC]

To a solution of ethyl 5-ethylsulfonyl-1-methyl-2-vinyl-imidazole-4-carboxylate (prepared as described above) (0.28 g, 0.925 mmol) in methanol (4.2 mL) under nitrogen was added a drop of trifluoroacetic acid, followed by diacetoxyiodobenzene (0.36 g, 1.11 mmol), cyclopropanecarbaldehyde oxime (0.105 g, 1.11 mmol) and one drop of trifluoroacetic acid. The reaction mixture was stirred at room temperature for 12 hours, then concentrated in vacuo. The crude was purified by combiflash (silica gel, ethyl acetate in cyclohexane) to afford ethyl 2-(3-cyclopropyl-4,5-dihydroisoxazol-5-yl)-5-ethylsulfonyl-1-methyl-imidazole-4-carboxylate. LCMS (method 1): Rt=0.99 min, m/z=356 $(M+H)^+$. $^1H$ NMR (400 MHz, $CDCl_3$) δ ppm: 5.61 (dd, J=10.67, 7.65 Hz, 1H) 4.43 (qd, J=7.15, 1.63 Hz, 2H) 4.03

(s, 3H) 3.88-3.97 (m, 1H) 3.54-3.69 (m, 2H) 3.16 (dd, J=16.81, 10.79 Hz, 1H) 1.82-1.89 (m, 1H) 1.42 (br t, J=7.15 Hz, 3H) 1.39 (br t, J=7.40 Hz, 3H) 0.84-1.02 (m, 4H).

Step 3: Preparation of 2-(3-cyclopropyl-4,5-dihydroisoxazol-5-yl)-5-ethylsulfonyl-1-methyl-imidazole-4-carboxylic acid (Intermediate I-26)

(I-26)

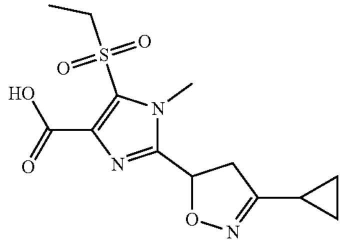

To a solution of ethyl 2-(3-cyclopropyl-4,5-dihydroisoxazol-5-yl)-5-ethylsulfonyl-1-methyl-imidazole-4-carboxylate (prepared as described above) (2.4 g, 6.4 mmol) in tetrahydrofuran (10 mL) was added a solution of lithium hydroxide monohydrate (0.71 g, 16 mmol) in water (2 mL) at 0° C. The reaction mixture was stirred at room temperature for 12 hours. After completion, the reaction mixture was concentrated in vacuo, the residue acidified with a 1N aqueous hydrochloric acid solution and poured into ethyl acetate. The organic layer was separated, washed twice with water, then once with brine, dried over anhydrous sodium sulfate, filtered and concentrated in vacuo to afford 2-(3-cyclopropyl-4,5-dihydroisoxazol-5-yl)-5-ethylsulfonyl-1-methyl-imidazole-4-carboxylic acid. This material was used as such in the next step. LCMS (method 1): Rt=0.15 min, m/z=328 $(M+H)^+$.

Step 4: Preparation of tert-butyl N-[2-(3-cyclopropyl-4,5-dihydroisoxazol-5-yl)-5-ethylsulfonyl-1-methyl-imidazol-4-yl]carbamate (Intermediate I-27)

(I-27)

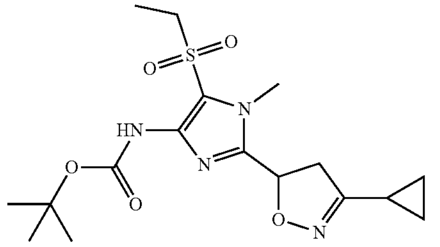

To a solution of 2-(3-cyclopropyl-4,5-dihydroisoxazol-5-yl)-5-ethylsulfonyl-1-methyl-imidazole-4-carboxylic acid (intermediate I-26 prepared as described above) (2.20 g, 6.4 mmol) in tert-butanol (33 mL) was added triethylamine (1.0 g, 10 mmol) at room temperature. The mixture was heated to 90° C. and stirred for 10 minutes. Diphenylphoshoryl azide (1.19 mL, 5.43 mmol) was added dropwise over a period of 10 minutes and the resulting reaction mixture was stirred at 90° C. for 60 minutes. The reaction mass was allowed to cool to room temperature, then quenched with ice cold water (100 mL) and the product extracted with ethyl acetate. The combined organic layers were washed twice with water, once with brine, dried over sodium sulfate, filtered and concentrated in vacuo. The crude was purified by combiflash (silica gel, 20-70% ethyl acetate in cyclohexane) to afford tert-butyl N-[2-(3-cyclopropyl-4,5-dihydroisoxazol-5-yl)-5-ethylsulfonyl-1-methyl-imidazol-4-yl] carbamate. LCMS (method 1): Rt=1.09 min, m/z=343 $[M+H-56]^+$. $^1H$ NMR (400 MHz, $CDCl_3$) δ ppm: 0.84-1.01 (m, 4H) 1.26-1.40 (m, 3H) 1.52 (s, 9H) 1.80-1.87 (m, 1H) 3.13-3.24 (m, 3H) 3.81-3.87 (m, 1H) 3.88 (s, 2H) 4.14 (d, J=7.09 Hz, 1H) 5.58 (dd, J=10.76, 8.31 Hz, 1H) 7.77 (s, 1H).

Example I-33: Preparation of tert-butyl N-[5-ethylsulfonyl-1-methyl-2-(2,2,2-trifluoroethoxy)imidazol-4-yl]carbamate (Intermediate I-33)

(I-33)

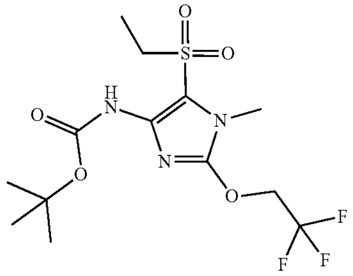

Step 1: Preparation of ethyl 5-ethylsulfonyl-1-methyl-2-(2,2,2-trifluoroethoxy)imidazole-4-carboxylate

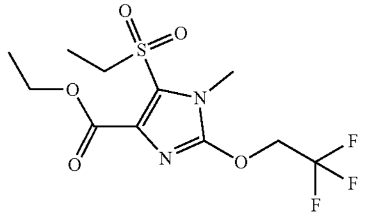 [SMILES: CCOC(=O)c1nc(OCC(F)(F)F)n(C)c1S(=O)(=O)CC]

To a solution of 2,2,2-trifluoroethanol (7.8 g, 77 mmol) and ethyl 2-bromo-5-ethylsulfonyl-1-methyl-imidazole-4-carboxylate (intermediate I-17 prepared as described in example P2 step 4) (5.0 g, 15 mmol) in pyridine (50 mL) were added potassium carbonate (6.4 g, 46 mmol) and cuprous iodide (0.44 g, 2.3 mmol) at 0° C. The reaction mixture was stirred at 16° C. for 16 hours. Then, the reaction mass was poured in ice cold water and stirred for 5 minutes. The aqueous layer was extracted with ethyl acetate (2×100 mL), the combined organic layers washed with water, then with brine, dried over sodium sulfate, filtered and concentrated in vacuo. The residue was triturated with n-pentane, filtered and dried in vacuo to afford ethyl 5-ethylsulfonyl-1-methyl-2-(2,2,2-trifluoroethoxy)imidazole-4-carboxylate. The crude material was used as such in the next step. LCMS (method 1): Rt=1.33 min, m/z=345 $(M+H)^+$.

Step 2: Preparation of 5-ethylsulfonyl-1-methyl-2-(2,2,2-trifluoroethoxy)imidazole-4-carboxylic acid (Intermediate I-32)

(I-32)

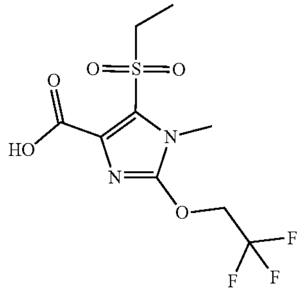

To a solution of ethyl 5-ethylsulfonyl-1-methyl-2-(2,2,2-trifluoroethoxy)imidazole-4-carboxylate (prepared as described above) (2.0 g g, 5.8 mmol) in tetrahydrofuran (20 mL) was added a solution of lithium hydroxide monohydrate (0.73 g, 17 mmol) in water (2 mL) at 0° C. The reaction mixture was stirred at room temperature for 3 hours. After completion, the reaction mixture was acidified with a 2N aqueous hydrochloric acid solution and diluted with water. The aqueous layer was extracted three times with ethyl acetate. The combined organic layers were washed with brine, dried over sodium sulfate, filtered and concentrated in vacuo to afford 5-ethylsulfonyl-1-methyl-2-(2,2,2-trifluoroethoxy)imidazole-4-carboxylic acid. This material was used as such in the next step. LCMS (method 1): Rt=0.95 min, m/z=317 $(M+H)^+$.

Step 3: Preparation of tert-butyl N-[5-ethylsulfonyl-1-methyl-2-(2,2,2-trifluoroethoxy)imidazol-4-yl] carbamate (Intermediate I-33)

(I-33)

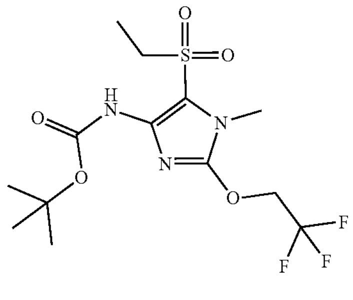

To a solution of 5-ethylsulfonyl-1-methyl-2-(2,2,2-trifluoroethoxy)imidazole-4-carboxylic acid (intermediate I-32 prepared as described above) (0.40 g, 1 mmol) in tert-butanol (8 mL) was added triethylamine (0.2 g, 2 mmol) at room temperature. The mixture was heated to 90° C. and stirred for 10 minutes. Diphenylphoshoryl azide (0.4 mL, 2 mmol) was added dropwise over a period of 15 minutes and the resulting reaction mixture was stirred at 90° C. for 40 minutes. The reaction mass was allowed to cool to room temperature, quenched with ice cold water (100 mL) and brine (40 mL), and the product extracted with ethyl acetate (3×100 mL). The combined organic layers were dried over sodium sulfate, filtered and concentrated in vacuo. The crude was purified by combiflash (silica gel, 40% ethyl acetate in cyclohexane) to afford tert-butyl N-[5-ethylsulfonyl-1-methyl-2-(2,2,2-trifluoroethoxy)imidazol-4-yl]carbamate. LCMS (method 1): Rt=1.10 min, m/z=288 $[M+H-100]^+$. $^1H$ NMR (400 MHz, $CDCl_3$) δ ppm 1.26-1.44 (m, 3H) 1.61 (s, 9H) 3.17 (q, J=7.46 Hz, 2H) 3.59 (s, 3H) 4.89 (q, J=8.07 Hz, 2H) 7.85 (s, 1H).

Example I-45: Preparation of tert-butyl N-[2-(3-chloropyrazol-1-yl)-5-ethylsulfonyl-1-methyl-imidazol-4-yl]carbamate (Intermediate I-45)

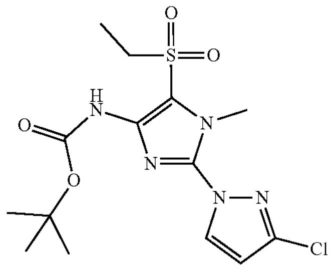 [SMILES: CCS(=O)(=O)c1c(NC(=O)OC(C)(C)C)nc(-n2ccc(Cl)n2)n1C]

Step 1: Preparation of ethyl 2-(3-chloropyrazol-1-yl)-5-ethylsulfonyl-1-methyl-imidazole-4-carboxylate

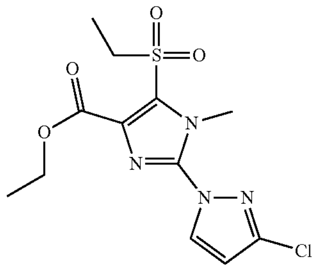 [SMILES: CCOC(=O)c1nc(-n2ccc(Cl)n2)n(C)c1S(=O)(=O)CC]

To a solution of ethyl 2-bromo-5-ethylsulfonyl-1-methyl-imidazole-4-carboxylate (intermediate I-17 prepared as described in example P2 step 4) (10.0 g, 30.8 mmol) and 3-chloro-1H-pyrazole (3.47 g, 33.8 mmol) in N,N-dimethylformamide (100 mL) were added N,N'-dimethylethane-1,2-diamine (0.542 g, 6.15 mmol), potassium carbonate (1.70 g, 12.3 mmol), followed by copper iodide (0.586 g, 3.08 mmol) at room temperature. The reaction mass was stirred at 120° C. for 16 hours. Then, water was added and the aqueous layer was extracted with ethyl acetate (3×100 mL). The combined organic layers were washed with water, dried over sodium sulfated and concentrated in vacuo. The crude was purified by combiflash (silica gel, 0-25% ethyl acetate in cyclohexane) to afford ethyl 2-(3-chloropyrazol-1-yl)-5-ethylsulfonyl-1-methyl-imidazole-4-carboxylate as a yellowish semi-solid. LCMS (method 1): Rt=1.09 min, m/z=347 $(M+H)^+$. $^1H$ NMR (400 MHz, $CDCl_3$) δ ppm 1.43 (td, J=7.31, 2.02 Hz, 6H) 3.67 (q, J=7.46 Hz, 2H) 4.11-4.17 (m, 3H) 4.46 (q, J=7.13 Hz, 2H) 6.47 (d, J=2.69 Hz, 1H) 8.12 (d, J=2.69 Hz, 1H).

Step 2: Preparation of 2-(3-chloropyrazol-1-yl)-5-ethylsulfonyl-1-methyl-imidazole-4-carboxylic acid (Intermediate I-46)

(I-46)

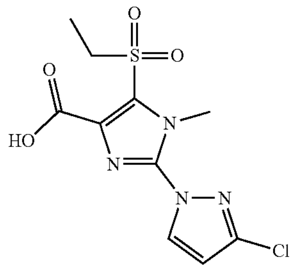

To a solution of ethyl 2-(3-chloropyrazol-1-yl)-5-ethylsulfonyl-1-methyl-imidazole-4-carboxylate (prepared as described above) (4.90 g, 14.1 mmol) in tetrahydrofuran (73.5 mL) was added a solution of lithium hydroxide monohydrate (0.889 g, 21 mmol) in water (19.6 mL) at room temperature. The reaction mixture was stirred at room temperature for 16 hours. After completion, the reaction mixture was quenched with water (100 mL), acidified with 2N aqueous hydrochloric acid (20 mL) and the product extracted with ethyl acetate (3×100 mL). The combined organic layers were washed with brine, dried over sodium sulfate, filtered and concentrated in vacuo. The crude material was washed twice with n-pentane and dried to afford 2-(3-cyclopropyl-4,5-dihydroisoxazol-5-yl)-5-ethylsulfonyl-1-methyl-imidazole-4-carboxylic acid as a white solid. This material was used as such in the next step. LCMS (method 1): Rt=0.92 min, m/z=319 $(M+H)^+$. $^1H$ NMR (400 MHz, DMSO-d6) δ ppm 1.28 (t, J=7.40 Hz, 3H) 3.67 (q, J=7.34 Hz, 2H) 3.83 (s, 3H) 6.80 (d, J=2.69 Hz, 1H) 8.41 (d, J=2.57 Hz, 1H) 13.27-14.12 (m, 1H).

Step 3: Preparation of tert-butyl N-[2-(3-chloropyrazol-1-yl)-5-ethylsulfonyl-1-methyl-imidazol-4-yl] carbamate (Intermediate I-45)

(I-45)

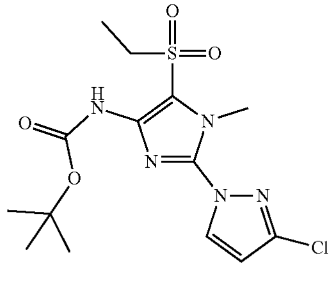

To a solution of 2-(3-chloropyrazol-1-yl)-5-ethylsulfonyl-1-methyl-imidazole-4-carboxylic acid (intermediate I-46 prepared as described above) (4.10 g, 12.9 mmol) in tert-butanol (82 mL) was added triethylamine (2.10 g, 20.6 mmol) at room temperature. The mixture was heated to 90° C. and stirred for 10 minutes. Diphenylphoshoryl azide (4.53 mL, 20.6 mmol) was added dropwise over a period of 15 minutes and the resulting reaction mixture was stirred at 90° C. for 40 minutes. The reaction mass was allowed to cool to room temperature, quenched with ice cold water (100 mL) and brine (40 mL), and the product extracted with ethyl acetate (3×100 mL). The combined organic layers were dried over sodium sulfate, filtered and concentrated in vacuo. The crude was purified by combiflash (silica gel, 40% ethyl acetate in cyclohexane) to afford tert-butyl N-[2-(3-chloropyrazol-1-yl)-5-ethylsulfonyl-1-methyl-imidazol-4-yl]carbamate. LCMS (method 2): Rt=1.37 min, m/z=388 $(M-H)^-$. $^1H$ NMR (400 MHz, $CDCl_3$) δ ppm 1.37 (t, J=7.40 Hz, 3H) 1.56 (s, 9H) 3.22 (d, J=7.46 Hz, 2H) 4.04 (s, 3H) 6.41 (d, J=2.81 Hz, 1H) 8.23 (d, J=2.69 Hz, 1H).

Example I-65: Preparation of tert-butyl N-[3-ethylsulfonyl-5-(2,2,2-trifluoroethoxy)-2-pyridyl]carbamate (Intermediate I-65)

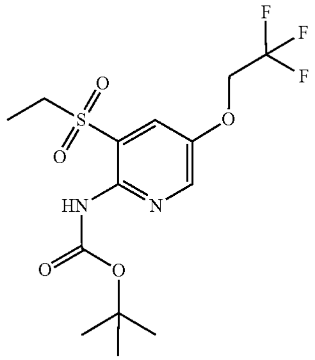 [SMILES: CCS(=O)(=O)c1cc(OCC(F)(F)F)cnc1NC(=O)OC(C)(C)C]

Step-1: Preparation of ethyl 5-bromo-3-ethylsulfanyl-pyridine-2-carboxylate

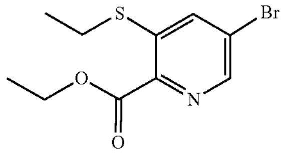

To a solution of 5-bromo-3-ethylsulfanyl-pyridine-2-carboxylic acid (CAS 1857366-13-2) (10.0 g, 34.31 mmol, 89.94 mass %) in ethyl alcohol (85 mL) was added sulfuric acid (1.9 mL, 34.31 mmol) dropwise and the mixture refluxed at 80° C. for 3 hours. The reaction mass was cooled to 24° C. and basified with a saturated aqueous sodium bicarbonate solution (50 mL), then diluted with brine. The aqueous layer was extracted with ethyl acetate (3×100 mL). The combined organic layers were dried over sodium sulfate, filtered and concentrated in vacuo. The crude material was triturated with cold methyl tert-butyl ether (20 mL) and stirred for 15 minutes at 24° C. The resulting precipitate was filtered through a Buchner funnel and dried in vacuo to afford ethyl 5-bromo-3-ethylsulfanyl-pyridine-2-carboxylate as a light brown solid. The crude was used as such for next step. LCMS (Method 1): Rt=1.05 min, m/z=290/292 $(M+H)^+$.

Step-2: Preparation of ethyl 3-ethylsulfanyl-5-hydroxy-pyridine-2-carboxylate

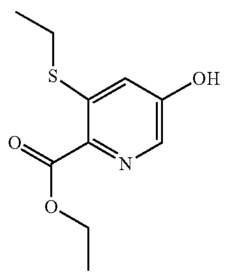

To a solution of ethyl 5-bromo-3-ethylsulfanyl-pyridine-2-carboxylate (prepared as described above) (15.0 g, 47.99 mmol) in N,N-dimethylformamide (95.98 mL) were added cesium carbonate (34.4 g, 105.6 mmol), followed by (E)-benzaldehyde oxime (6.81 mL, 62.39 mmol) and the reaction mass was stirred reaction at 80° C. for 15 hours. The reaction mass was quenched with ice-cold water, acidified with an aqueous 2N hydrochloric acid and extracted in ethyl acetate (3×100 mL). The combined organic layers were washed with water (100 mL), dried over anhydrous sodium sulfate, filtered and concentrated in vacuo. The obtained residue was triturated with tert-butyl methyl ether, the solid isolated by filtration and dried in vacuo to afford ethyl 3-ethylsulfanyl-5-hydroxy-pyridine-2-carboxylate as a brown solid. The crude was used as such for next step. LCMS (Method 1): Rt=0.98 min, m/z=228 $(M+H)^+$.

Step-3: Preparation of ethyl 3-ethylsulfanyl-5-(2,2,2-trifluoroethoxy)pyridine-2-carboxylate

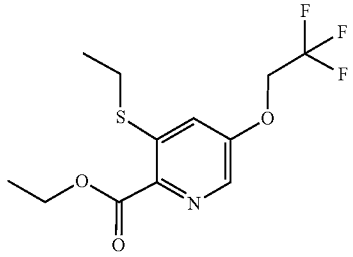 [SMILES: CCOC(=O)c1ncc(OCC(F)(F)F)cc1SCC]

To a solution of ethyl 3-ethylsulfanyl-5-hydroxy-pyridine-2-carboxylate (prepared as described above) (4.108 g, 18.07 mmol) in N,N-dimethylformamide (20 mL) were added potassium carbonate (4.99 g, 36.15 mmol) and 2,2,2-trifluoroethyl 4-methylbenzenesulfonate (5.97 g, 23.50 mmol) under nitrogen and the reaction mixture was stirred at 75° C. for 15 hours. The reaction mass was diluted with ice cold water (200 mL), and the product extracted with ethyl acetate (3×60 mL). The combined organic layers were dried over sodium sulfate, filtered and concentrated in vacuo. The crude compound was purified by combiflash (silica gel, 0-40% ethyl acetate in cyclohexane) to afford ethyl 3-ethylsulfanyl-5-(2,2,2-trifluoroethoxy)pyridine-2-carboxylate as an off white solid. LCMS (Method 1): Rt=1.15 min, m/z=310 $(M+H)^+$.

Step-4: Preparation of ethyl 3-ethylsulfonyl-5-(2,2,2-trifluoroethoxy)pyridine-2-carboxylate

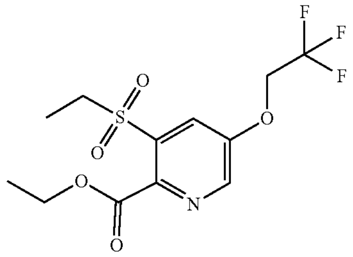 [SMILES: CCOC(=O)c1ncc(OCC(F)(F)F)cc1S(=O)(=O)CC]

To 0° C. cooled solution of ethyl 3-ethylsulfanyl-5-(2,2,2-trifluoroethoxy)pyridine-2-carboxylate (prepared as described above) (2.424 g, 7.837 mmol) in acetonitrile (20 mL) was added 3-chlorobenzenecarboperoxoic acid (4.25 g, 17.24 mmol, 70 mass %). The reaction mass was stirred at room temperature for 1.5 hours. The reaction mass was concentrated carefully in vacuo and the residue quenched with an aqueous 2N sodium hydroxide solution (20 mL). Water (60 mL) and ethyl acetate (40 mL) were added and the organic layer was separated. The aqueous layer was extracted with ethyl acetate (2×50 mL). The combined organic layers were washed with brine (60 mL), dried over sodium sulfate and concentrated in vacuo. The crude was purified by combiflash (silica gel, 0-40% ethyl acetate in cyclohexane) to afford ethyl 3-ethylsulfonyl-5-(2,2,2-trifluoroethoxy)pyridine-2-carboxylate as an off white solid. LCMS (Method 2): Rt=1.09 min, m/z=342 $(M+H)^+$.

Step-5: Preparation of 3-ethylsulfonyl-5-(2,2,2-trifluoroethoxy)pyridine-2-carboxylic acid (Intermediate I-50)

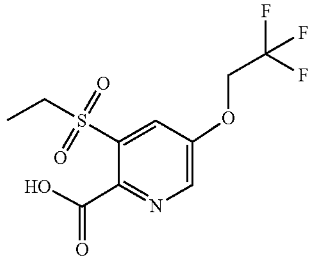 [SMILES: CCS(=O)(=O)c1cc(OCC(F)(F)F)cnc1C(=O)O]

To a solution of ethyl 3-ethylsulfonyl-5-(2,2,2-trifluoroethoxy)pyridine-2-carboxylate (prepared as described above) (2.080 g, 6.094 mmol) in tetrahydrofuran (20 mL) was added a solution of lithium hydroxide monohydrate (1.077 g, 24.38 mmol) in water (7 mL) and the reaction mixture was stirred at room temperature overnight. The reaction mass was concentrated in vacuo, acidified with an aqueous 1N hydrochloric acid solution, and the product extracted with ethyl acetate (2×50 mL). The combined organic layers were washed with water (50 mL) and brine, dried over sodium sulfate, filtered and concentrated in vacuo to afford 3-ethylsulfonyl-5-(2,2,2-trifluoroethoxy)pyridine-2-carboxylic acid (I-50) as an off white solid. The crude was used as such for next step. LCMS (Method 2): Rt=0.91 min, m/z=314 $(M+H)^+$.

Step-6: Preparation of tert-butyl N-[3-ethylsulfonyl-5-(2,2,2-trifluoroethoxy)-2-pyridyl]carbamate (Intermediate I-65)

(I-65)

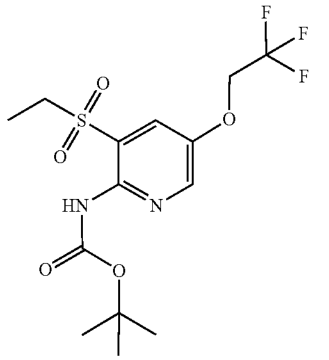

To a solution of 3-ethylsulfonyl-5-(2,2,2-trifluoroethoxy) pyridine-2-carboxylic acid (intermediate I-50 prepared as described above) (2 g, 6.3847 mmol) in tert-butanol (40 mL) was added triethylamine (1.0441 g, 10.215 mmol) and the reaction mass was heated at 90° C. for 10 minutes. Diphenylphosphoryl azide (2.24 mL, 10.21 mmol) was added dropwise over a period of 15 minutes and the resulting reaction mass was stirred at 90° C. for 45 minutes. The reaction mass was quenched with ice-cold water (50 mL) and the product extracted with ethyl acetate (3×70 mL). The combined organic layers were washed with brine, dried over sodium sulfate, filtered and concentrated in vacuo. The crude was purified by combiflash (silica gel, 0-50% ethyl acetate in cyclohexane) to afford tert-butyl N-[3-ethylsulfonyl-5-(2,2,2-trifluoroethoxy)-2-pyridyl]carbamate (1-65). LCMS (Method 1): Rt=1.14 min, m/z=383 $[(M-H)]^+$.

Example I-59: Preparation of tert-butyl N-(6-cyclopropyl-3-ethylsulfonyl-2-pyridyl)carbamate (Intermediate I-59)

(I-59)

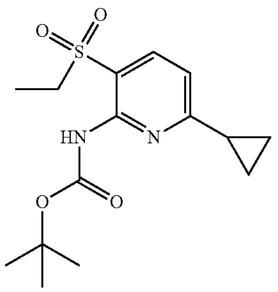

Step-1: Preparation of ethyl 6-chloro-3-ethylsulfonyl-pyridine-2-carboxylate

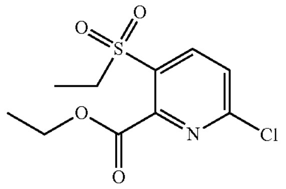 [SMILES: CCOC(=O)c1nc(Cl)ccc1S(=O)(=O)CC]

To 0° C. cooled solution of 6-chloro-3-ethylsulfonyl-pyridine-2-carboxylic acid (CAS 1848219-28-2) (10 g, 40.05 mmol) in methylsulfinylmethane (100 mL) were added potassium carbonate (11.07 g, 80.106 mmol), followed by iodoethane (6.44 mL, 80.106 mmol) dropwise. The reaction mixture was stirred at room temperature overnight. The reaction mass was poured into ice-cold water and the product extracted with ethyl acetate (3×100 mL). The combined organic layers were dried over sodium sulfate, filtered and concentrated in vacuo. The crude compound was purified by combiflash (silica gel, 20% ethyl acetate in cyclohexane) to afford ethyl 6-chloro-3-ethylsulfonyl-pyridine-2-carboxylate. LCMS (Method 1): Rt=1.05 min, m/z=278 $(M+H)^+$.

Step-2: Preparation of ethyl 6-cyclopropyl-3-ethylsulfonyl-pyridine-2-carboxylate

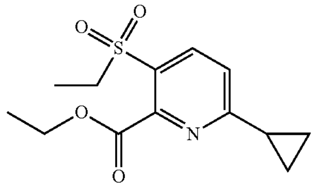 [SMILES: CCOC(=O)c1nc(C2CC2)ccc1S(=O)(=O)CC]

To a solution of ethyl 6-chloro-3-ethylsulfonyl-pyridine-2-carboxylate (prepared as described above) (9.3 g, 33 mmol) in toluene (93 mL) and water (28 mL) were added potassium carbonate (14.0 g, 100 mmol), cyclopropyl boronic acid (7.6 g, 84 mmol) and the reaction mass was degassed with nitrogen for 10 minutes. 1,1'-Bis(diphenylphosphino)ferrocene-palladium(II)dichloride dichloromethane complex (1.4 g, 1.70 mmol) was added and the reaction mass was degassed with nitrogen for another 5 minutes and stirred for 5 hours at 110° C. under nitrogen atmosphere. The reaction mixture was allowed to cool to room temperature, diluted with water, extracted with ethyl acetate (3×) and washed with brine. The combined organic layers were dried over sodium sulfate, filtered and concentrated in vacuo. The crude compound was purified by combiflash (silica gel, 20% ethyl acetate in cyclohexane) to afford ethyl 6-cyclopropyl-3-ethylsulfonyl-pyridine-2-carboxylate as a solid. LCMS (Method 1): Rt=1.08 min, m/z=284 $(M+H)^+$.

Step-3: Preparation of 6-cyclopropyl-3-ethylsulfonyl-pyridine-2-carboxylic acid (Intermediate I-48)

(I-48)

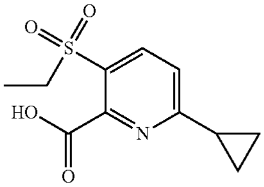

To a solution of ethyl 6-cyclopropyl-3-ethylsulfonyl-pyridine-2-carboxylate (prepared as described above) (2.0 g, 7.1 mmol) in tetrahydrofuran (16 mL) and water (4 mL) was added lithium hydroxide monohydrate (0.89 g, 21 mmol) at 0-5° C. The reaction mixture was stirred at room temperature for 24 hours. Upon completion, the reaction mass was concentrated in vacuo and the residue acidified with an aqueous 2N hydrochloric acid solution. The formed white precipitate was filtered through a Buchner funnel and the solid residue washed with cold water followed by cyclohexane, then dried in vacuo to afford 6-cyclopropyl-3-ethylsulfonyl-pyridine-2-carboxylic acid (1-48) as a solid. The crude was used as such for next step. LCMS (Method 1): Rt=0.66 min, m/z=256 $(M+H)^+$.

Step-4: Preparation of tert-butyl N-(6-cyclopropyl-3-ethylsulfonyl-2-pyridyl)carbamate (Intermediate I-59)

(I-59)

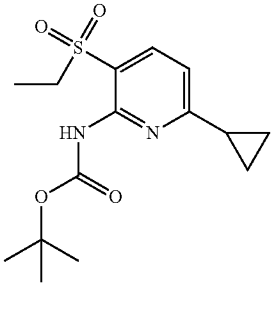

To a solution of 6-cyclopropyl-3-ethylsulfonyl-pyridine-2-carboxylic acid (intermediate I-48 prepared as described above) (1.7 g, 6.3 mmol) in tert-butanol (26 mL) was added triethylamine (1.4 mL, 10 mmol) and the reaction mass was heated at 90° C. for 10 minutes. Diphenylphosphoryl azide (2.2 mL, 10 mmol) was added dropwise over a period of 10 minutes and the resulting reaction mass was stirred at 90° C. for 60 minutes. The reaction mass was quenched with ice-cold water (100 mL) and the product extracted with ethyl acetate (2×). The combined organic layers were washed with brine, dried over sodium sulfate, filtered and concentrated in vacuo. The crude was purified by combiflash (silica gel, 20-70% ethyl acetate in cyclohexane) to afford tert-butyl N-(6-cyclopropyl-3-ethylsulfonyl-2-pyridyl)carbamate (1-59). LCMS (Method 1): Rt=1.14 min, m/z=327 $(M+H)^+$. LCMS (Method 2): Rt=1.42 min. m/z=327 $(M+H)^+$.

Example I-67: Preparation of tert-butyl N-[5-(2,2-difluoropropoxy)-3-ethylsulfonyl-2-pyridyl]carbamate (Intermediate I-67)

(I-67)

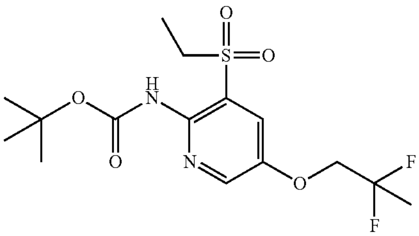

Step-1: Preparation of methyl 5-acetonyloxy-3-ethylsulfanyl-pyridine-2-carboxylate

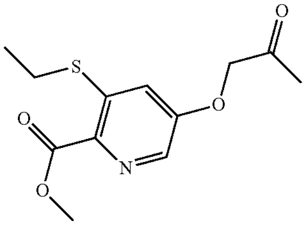 [SMILES: CCSc1cc(OCC(C)=O)cnc1C(=O)OC]

To a solution of methyl 3-ethylsulfanyl-5-hydroxy-pyridine-2-carboxylate (CAS 2417036-63-4) (8.0 g, 38.0 mmol) in N,N-dimethylformamide (80 mL) was added potassium carbonate (16.0 g, 110.0 mmol), followed by 1-chloropropan-2-one (10.0 g, 110.0 mmol). The reaction mixture was stirred at room temperature overnight. After completion, the reaction mass was diluted with water (150 mL) and extracted with ethyl acetate (3×150 mL). The combined organic layers were dried over sodium sulfate, filtered and concentrated in vacuo. The crude was purified by combiflash (silica gel, 30% ethyl acetate in cyclohexane) to afford methyl 5-acetonyloxy-3-ethylsulfanyl-pyridine-2-carboxylate. LCMS (Method 1): Rt=0.84 min, m/z=270 $(M+H)^+$.

Step-2: Preparation of methyl 5-(2,2-difluoropropoxy)-3-ethylsulfanyl-pyridine-2-carboxylate

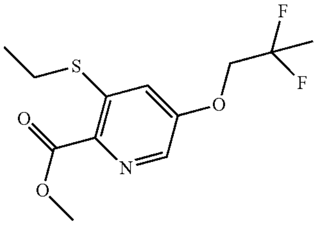 [SMILES: CCSc1cc(OCC(C)(F)F)cnc1C(=O)OC]

To a 0° C. cooled solution of methyl 5-acetonyloxy-3-ethylsulfanyl-pyridine-2-carboxylate (prepared as described above) (8.3 g, 31 mmol) in dichloromethane (170 mL) was added N-ethyl-N-(trifluoro-$\lambda^4$-sulfanyl)ethanamine (16 mL, 120 mmol). The reaction mixture was allowed to come to room temperature and stirred for 16 hours. The reaction mass was quenched with solid sodium bicarbonate, diluted with water (100 mL), and the product extracted with dichloromethane (3×80 mL). The combined organic layers were dried over sodium sulfate, filtered and concentrated in vacuo. The crude was purified by combiflash (silica gel, 30% ethyl acetate in cyclohexane) to afford methyl 5-(2,2-difluoropropoxy)-3-ethylsulfanyl-pyridine-2-carboxylate. LCMS (Method 1): Rt=1.43 min, m/z=292 $(M+H)^+$.

Step-3: Preparation of 5-(2,2-difluoropropoxy)-3-ethylsulfanyl-pyridine-2-carboxylic acid

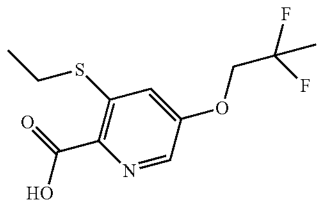 [SMILES: CCSc1cc(OCC(C)(F)F)cnc1C(=O)O]

To a solution of methyl 5-(2,2-difluoropropoxy)-3-ethylsulfanyl-pyridine-2-carboxylate (prepared as described above) (8.4 g, 29 mmol) in tetrahydrofuran (130 mL) was added a solution lithium hydroxide monohydrate (1.8 g, 43 mmol) in water (34 mL). The reaction mixture was stirred at room temperature for 2 hours. The reaction mass was acidified with an aqueous 2N HCl solution, diluted with water (100 mL) and the product extracted with ethyl acetate (3×100 mL). The combined organic layers were dried over sodium sulfate, filtered and concentrated in vacuo to afford 5-(2,2-difluoropropoxy)-3-ethylsulfanyl-pyridine-2-carboxylic acid. The crude was used as such for next step. LCMS (Method 1): Rt=0.91 min, m/z=276 $(M-H)^-$.

Step-4: Preparation of tert-butyl N-[5-(2,2-difluoropropoxy)-3-ethylsulfanyl-2-pyridyl]carbamate

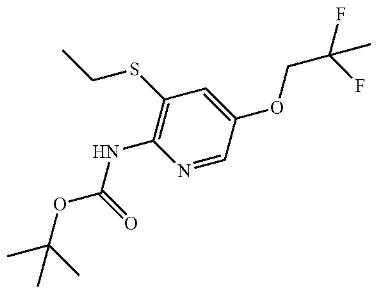 [SMILES: CCSc1cc(OCC(C)(F)F)cnc1NC(=O)OC(C)(C)C]

To a solution of 5-(2,2-difluoropropoxy)-3-ethylsulfanyl-pyridine-2-carboxylic acid (prepared as described above) (4.5 g, 15 mmol) in tert-butanol (68 mL) was added triethylamine (3.5 mL, 25 mmol) and the reaction mass was heated at 90° C. for 10 minutes. Diphenylphosphoryl azide (5.4 mL, 25 mmol) was then added dropwise over a period of 10 minutes and the resulting reaction mass was stirred at 90° C. for 60 minutes. The reaction mixture was quenched with ice-cold water (100 mL) and the product extracted twice with ethyl acetate. The combined organic layers were washed with brine, dried over sodium sulfate, filtered and concentrated in vacuo. The crude was purified by combiflash (silica gel, 20-70% ethyl acetate in cyclohexane) to afford tert-butyl N-[5-(2,2-difluoropropoxy)-3-ethylsulfanyl-2-pyridyl]carbamate. LCMS (Method 1): Rt=1.16 min. m/z=293 [(M+H)-56]+.

Step-5: Preparation of tert-butyl N-[5-(2,2-difluoropropoxy)-3-ethylsulfonyl-2-pyridyl]carbamate (Intermediate I-67)

(I-67)

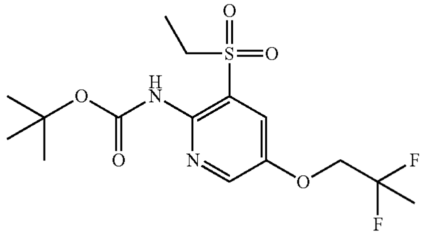

To a solution of tert-butyl N-[5-(2,2-difluoropropoxy)-3-ethylsulfanyl-2-pyridyl]carbamate (prepared as described above) (4.5 g, 12 mmol) in ethanol (45 mL) was added 3-chlorobenzoic acid (2 g, 12.135 mmol) was added at 15-20° C. The reaction mass was stirred at room temperature for 12 hours. The reaction was quenched with saturated sodium sulfite (5 mL), then the resulting reaction mass was added to an ice-cold solution of sodium carbonate (1.5 g, 14 mmol) in water (200 mL) and stirred for 30 minutes. The resulting white precipitate was filtered through a Buchner funnel and the solid residue washed with cold water followed by cyclohexane, dried in vacuo to afford tert-butyl N-[5-(1-cyano-1-methyl-ethoxy)-3-ethylsulfonyl-2-pyridyl]carbamate (1-67) as white solid. LCMS (Method 1): Rt=1.13 min, m/z=325 [(M+H)-56]+ and 281 [(M+H)-100]+.

Example I-63: Preparation of tert-butyl N-[5-(1,1-difluoroethyl)-3-ethylsulfonyl-2-pyridyl]carbamate (Intermediate I-63)

(I-63)

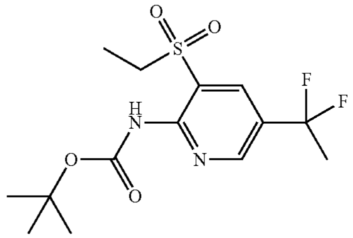

Step-1: Preparation of ethyl 5-bromo-3-ethylsulfanyl-pyridine-2-carboxylate

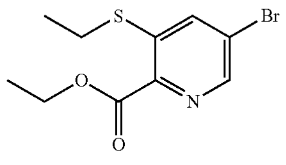

To a solution of 5-bromo-3-ethylsulfanyl-pyridine-2-carboxylic acid (CAS 1857366-13-2) (10.0 g, 34.31 mmol, 89.94 mass %) in ethyl alcohol (85 mL) was added sulfuric acid (1.9 mL, 34.31 mmol) dropwise and the mixture refluxed at 80° C. for 3 hours. The reaction mass was cooled to 24° C. and basified with a saturated aqueous sodium bicarbonate solution (50 mL), then diluted with brine. The aqueous layer was extracted with ethyl acetate (3×100 mL). The combined organic layers were dried over sodium sulfate, filtered and concentrated in vacuo. The crude material was triturated with cold methyl tert-butyl ether (20 mL) and stirred for 15 minutes at 24° C. The resulting precipitate was filtered through a Buchner funnel and dried in vacuo to afford ethyl 5-bromo-3-ethylsulfanyl-pyridine-2-carboxylate as a light brown solid. The crude was used as such for next step. LCMS (Method 1): Rt=1.05 min, m/z=290/292 $(M+H)^+$.

Step-2: Preparation of ethyl 5-bromo-3-ethylsulfonyl-pyridine-2-carboxylate

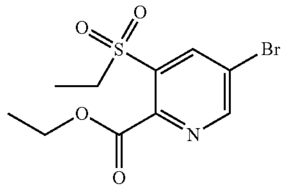 [SMILES: CCOC(=O)c1ncc(Br)cc1S(=O)(=O)CC]

To a solution of ethyl 5-bromo-3-ethylsulfanyl-pyridine-2-carboxylate (prepared as described above) (20.0 g, 65.47 mmol) in ethanol (200 mL) was added 3-chlorobenzenecarboperoxoic acid (61.63 g, 196.43 mmol) at 0° C. The reaction mass was stirred at room temperature for 12 hours. After completion, the reaction mass was quenched with a saturated aqueous solution of sodium sulfite (5 mL), then the resulting reaction mass was added to an ice-cold solution of sodium carbonate (7.1 g, 67 mmol) in water (200 mL) and stirred for 30 minutes. The resulting white precipitate was filtered through a Buchner funnel, the solid residue washed with cold water followed by cyclohexane, dried in vacuo to afford ethyl 5-bromo-3-ethylsulfonyl-pyridine-2-carboxylate as a white solid. LCMS (Method 1): Rt=1.06 min, m/z=322/324 [(M+H)]+.

Step-3: Preparation of ethyl 5-acetyl-3-ethylsulfonyl-pyridine-2-carboxylate

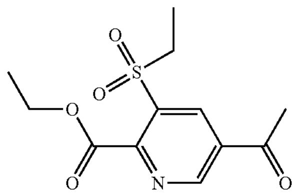 [SMILES: CCOC(=O)c1ncc(C(C)=O)cc1S(=O)(=O)CC]

To a solution of ethyl 5-bromo-3-ethylsulfonyl-pyridine-2-carboxylate (prepared as described above) (5 g, 14.743 mmol) in N,N-dimethylformamide (58.97 mL) was added tributyl(1-ethoxyvinyl)tin (6.727 g, 17.692 mmol) and the reaction mass was degassed with nitrogen for 15 minutes. Bis(triphenylphosphine)palladium(II) dichloride (0.522 g, 0.737 mmol) was added and to the reaction mass heated at 80° C. for 3 hours. The reaction mixture was cooled and an aqueous 2N HCl solution (20 mL) was added. After stirring at room temperature for 30 minutes, the reaction mass was quenched with an aqueous KF solution, diluted with water (100 ml) and ethyl acetate (100 mL). The solution was filtered through celite and the residue washed with ethyl acetate (20 mL). The combined organic layers were dried over sodium sulfate, filtered and concentrated in vacuo. The crude compound was purified by combiflash (silica gel, 30-40% ethyl acetate in cyclohexane) to afford ethyl 5-acetyl-3-ethylsulfonyl-pyridine-2-carboxylate. LCMS (Method 2): Rt=1.16 min, m/z=286 [(M+H)]+.

Step-4: Preparation of ethyl 5-(1,1-difluoroethyl)-3-ethylsulfonyl-pyridine-2-carboxylate

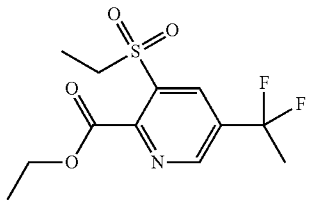 [SMILES: CCOC(=O)c1ncc(C(C)(F)F)cc1S(=O)(=O)CC]

To a solution of ethyl 5-acetyl-3-ethylsulfonyl-pyridine-2-carboxylate (prepared as described above) (3.5 g, 12 mmol) in toluene (35 mL) was added bis(2-methoxyethyl) aminosulfur trifluoride (13 mL, 35 mmol) dropwise under a nitrogen atmosphere. The reaction mixture was stirred at 80° C. for 12 hours, then quenched with a saturated sodium bicarbonate solution and diluted with ice-cold water (100 mL). The aqueous phase was extracted with ethyl acetate (3×75 mL). The combined organic layers were dried over sodium sulfate, filtered and concentrated in vacuo. The crude compound was purified by combiflash (silica gel, 30-40% ethyl acetate in cyclohexane) to afford ethyl 5-(1,1-difluoroethyl)-3-ethylsulfonyl-pyridine-2-carboxylate. LCMS (Method 1): Rt=1.02 min, m/z=308 $(M+H)^+$.

Step-5: Preparation of 5-(1,1-difluoroethyl)-3-ethylsulfonyl-pyridine-2-carboxylic acid (Intermediate I-49)

(I-49)

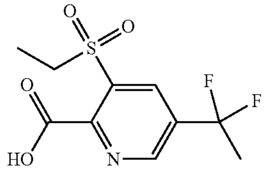

To a solution of ethyl 5-(1,1-difluoroethyl)-3-ethylsulfonyl-pyridine-2-carboxylate (prepared as described above) (3.0 g, 9.27 mmol) in tetrahydrofuran (24 mL) was added a solution of lithium hydroxide monohydrate (0.6799 g, 27.82 mmol) in water (6 mL) at 5° C. The reaction mixture was stirred at room temperature for 12 hours. Upon completion, the reaction mass was concentrated in vacuo and acidified with an aqueous 2N hydrochloric acid solution. The formed white precipitate was filtered through a Buchner funnel, and washed with cold water followed by cyclohexane, dried in vacuo to afford 5-(1,1-difluoroethyl)-3-ethylsulfonyl-pyridine-2-carboxylic acid (1-49) as a white solid. LCMS (Method 2): Rt=0.77 min, m/z=280 $(M+H)^+$.

Step-6: Preparation of tert-butyl N-[5-(1,1-difluoroethyl)-3-ethylsulfonyl-2-pyridyl]carbamate (Intermediate I-63)

(I-63)

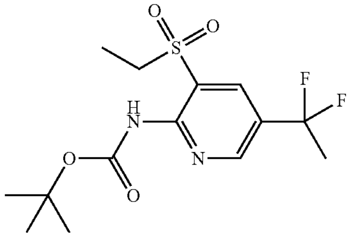

To a solution of 5-(1,1-difluoroethyl)-3-ethylsulfonyl-pyridine-2-carboxylic acid (intermediate I-49 prepared as described above) (2.4 g, 8.2 mmol) in tert-butanol (36 mL) was added triethylamine (1.8 mL, 13 mmol) and the reaction mass was heated at 90° C. for 10 minutes. Diphenylphosphoryl azide (2.9 mL, 13 mmol) was added dropwise over a period of 10 minutes and the resulting reaction mass was stirred at 90° C. for 40 minutes. The reaction mass was quenched with ice-cold water (30 mL) and the product extracted with ethyl acetate (2×). The combined organic layers were washed with brine, dried over sodium sulfate, filtered and concentrated in vacuo. The crude was purified by combiflash (silica gel, 60% ethyl acetate in cyclohexane) to afford tert-butyl N-[5-(1,1-difluoroethyl)-3-ethylsulfonyl-2-pyridyl]carbamate (1-63). LCMS (Method 2): Rt=1.37 min, m/z=295 $[(M+H)-56]^+$. LCMS (Method 1): Rt=1.08 min, m/z=349 $(M-H)^-$.

Example I-53: Preparation of tert-butyl N-[5-(1-cyano-1-methyl-ethoxy)-3-ethylsulfonyl-2-pyridyl]carbamate (Intermediate I-53)

(I-53)

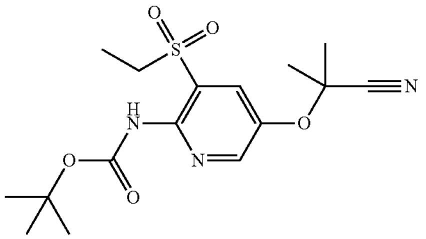

Step-1: Preparation of tert-butyl N-[5-(1-cyano-1-methyl-ethoxy)-3-ethylsulfanyl-2-pyridyl]carbamate

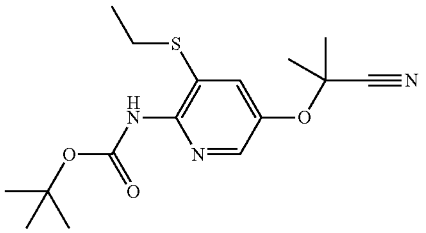 [SMILES: CCSc1cc(OC(C)(C)C#N)cnc1NC(=O)OC(C)(C)C]

To a solution of 5-(1-cyano-1-methyl-ethoxy)-3-ethylsulfanyl-pyridine-2-carboxylic acid (CAS 2417036-66-7, prepared as described in WO2020141136) (4 g, 14.27 mmol) in tert-butanol (40 mL) was added triethylamine (3.21 mL, 22.83 mmol) and the reaction mass was heated at 90° C. After 10 minutes diphenylphosphoryl azide (5.021 mL, 22.83 mmol) was added dropwise over a period of 15 minutes and the resulting reaction mass was stirred at 90° C. for 40 minutes. The reaction mixture was quenched with water (30 mL) and brine (20 mL), and the product extracted with ethyl acetate (2×50 mL). The combined organic layers were dried over sodium sulfate, filtered and concentrated in vacuo. The crude was purified by combiflash (silica gel, 40-60% ethyl acetate in cyclohexane) to afford tert-butyl N-[5-(1-cyano-1-methyl-ethoxy)-3-ethylsulfanyl-2-pyridyl]carbamate. LCMS (Method 1): Rt=1.17 min. m/z=282 $[(M+H)-56]^+$.

Step-2: Preparation of tert-butyl N-[5-(1-cyano-1-methyl-ethoxy)-3-ethylsulfonyl-2-pyridyl]carbamate (Intermediate I-53)

(I-53)

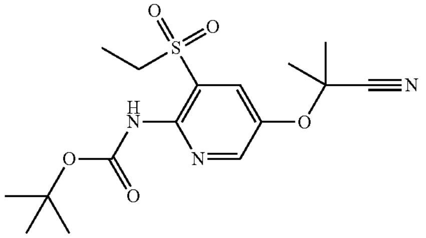

To a solution of tert-butyl N-[5-(1-cyano-1-methyl-ethoxy)-3-ethylsulfanyl-2-pyridyl]carbamate (prepared as described above) (1.5 g, 4.2 mmol) in ethanol (15 mL) was added 3-chlorobenzoic acid (0.7 g, 4 mmol) at 15-20° C. The reaction mass was stirred at room temperature for 12 hours. The reaction was quenched with saturated sodium sulfite (5 mL), then the resulting reaction mass was added to an ice-cold solution of sodium carbonate (0.4 g, 4 mmol) in water (200 mL) and stirred for 30 minutes. The resulting white precipitate was filtered through a Buchner funnel and the solid residue washed with cold water followed by cyclohexane, dried in vacuo to afford tert-butyl N-[5-(1-cyano-1-methyl-ethoxy)-3-ethylsulfonyl-2-pyridyl]carbamate (1-53) as a white solid. The crude was used as such for next step. LCMS (Method 2): Rt=1.37 min, m/z=314 $[(M+H)-56]^+$.

TABLE I

| Examples of intermediates | | | | | | |
|---|---|---|---|---|---|---|
| | | | $^1$H NMR, LCMS | | | |
| No. | IUPAC name | Structures | $R_t$ (min) | [M + H]$^+$ or [M − H]$^-$ (measured) | Meth-od | Mp (° C.) |
| I-24 | tert-butyl N-[2-(1-cyclopropylpyrazol-4-yl)-5-ethylsulfonyl-1-methyl-imidazol-4-yl]carbamate | 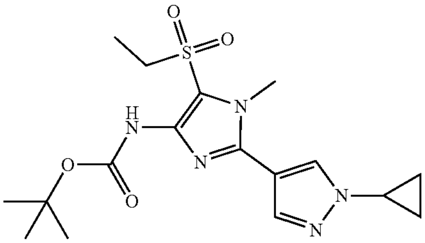 [SMILES: CCS(=O)(=O)c1c(NC(=O)OC(C)(C)C)nc(-c2cnn(C3CC3)c2)n1C] | 1.35 | 396 | 2 | |
| I-25 | 2-(1-cyclopropylpyrazol-4-yl)-5-ethylsulfonyl-1-methyl-imidazole-4-carboxylic acid | 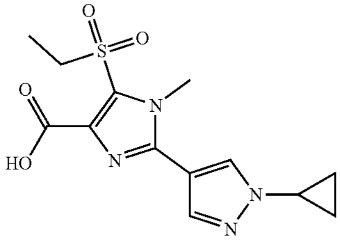 [SMILES: CCS(=O)(=O)c1c(C(=O)O)nc(-c2cnn(C3CC3)c2)n1C] | 1.02 | 325 | 2 | |
| I-26 | 2-(3-cyclopropyl-4,5-dihydroisoxazol-5-yl)-5-ethylsulfonyl-1-methyl-imidazole-4-carboxylic acid | 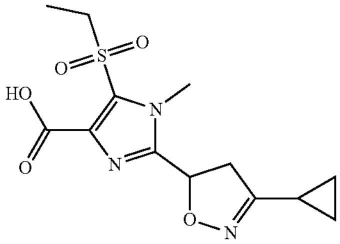 [SMILES: CCS(=O)(=O)c1c(C(=O)O)nc(C2CC(C3CC3)=NO2)n1C] | 0.15 | 328 | 1 | |
| I-27 | tert-butyl N-[2-(3-cyclopropyl-4,5-dihydroisoxazol-5-yl)-5-ethylsulfonyl-1-methyl-imidazol-4-yl]carbamate | 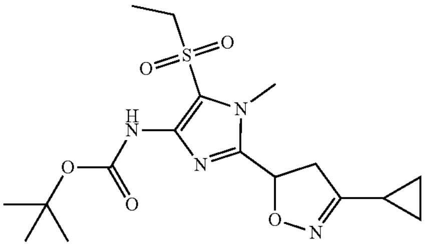 [SMILES: CCS(=O)(=O)c1c(NC(=O)OC(C)(C)C)nc(C2CC(C3CC3)=NO2)n1C] | 1.09 | 343 [(M + H)$^+$ − 56] | 1 | 65-75 |
| I-28 | 2-[1-[(1-cyanocyclopropyl)methyl]pyrazol-4-yl]-5-ethylsulfonyl-1-methyl-imidazole-4-carboxylic acid | 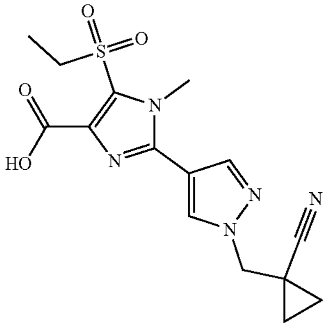 [SMILES: CCS(=O)(=O)c1c(C(=O)O)nc(-c2cnn(CC3(C#N)CC3)c2)n1C] | 0.19 | 364 | 1 | |

TABLE I-continued

| Examples of intermediates | | | | | | |
|---|---|---|---|---|---|---|
| | | | $^{1}$H NMR, LCMS | | | |
| No. | IUPAC name | Structures | $R_t$ (min) | [M + H]$^+$ or [M − H]$^-$ (measured) | Meth-od | Mp (° C.) |
| I-29 | tert-butyl N-[2-[1-[(1-cyanocyclopropyl)methyl] pyrazol-4-yl]-5-ethylsulfonyl-1-methyl-imidazol-4-yl]carbamate | 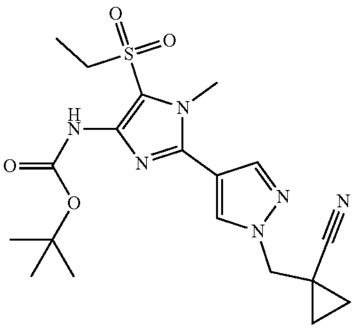 [SMILES: CCS(=O)(=O)c1c(NC(=O)OC(C)(C)C)nc(-c2cnn(CC3(C#N)CC3)c2)n1C] | 1.01 | 433 | 1 | |
| I-30 | 2-[1-(2,2-difluoroethyl)pyrazol-4-yl]-5-ethylsulfonyl-1-methyl-imidazole-4-carboxylic acid | 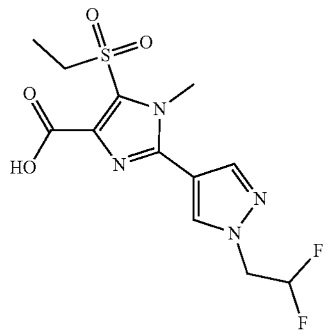 [SMILES: CCS(=O)(=O)c1c(C(=O)O)nc(-c2cnn(CC(F)F)c2)n1C] | 1.06 | 349 | 1 | |
| I-31 | tert-butyl N-[2-[1-(2,2-difluoroethyl)pyrazol-4-yl]-5-ethylsulfonyl-1-methyl-imidazol-4-yl]carbamate | 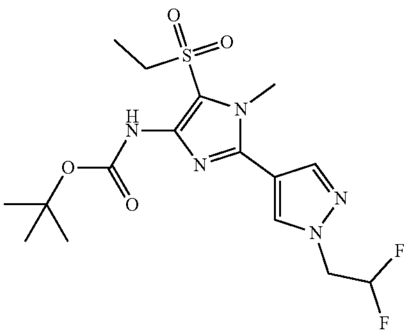 [SMILES: CCS(=O)(=O)c1c(NC(=O)OC(C)(C)C)nc(-c2cnn(CC(F)F)c2)n1C] | 1.01 | 418 | 1 | |
| I-32 | 5-ethylsulfonyl-1-methyl-2-(2,2,2-trifluoroethoxy)imidazole-4-carboxylic acid | 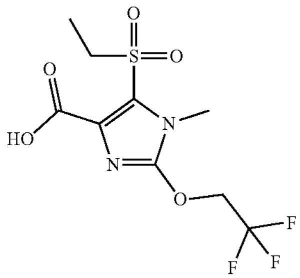 [SMILES: CCS(=O)(=O)c1c(C(=O)O)nc(OCC(F)(F)F)n1C] | 0.95 | 317 | 1 | |

TABLE I-continued

| Examples of intermediates | | | | | | |
|---|---|---|---|---|---|---|
| | | | $^1$H NMR, LCMS | | | |
| No. | IUPAC name | Structures | $R_t$ (min) | [M + H]$^+$ or [M − H]$^-$ (measured) | Meth-od | Mp (° C.) |
| I-33 | tert-butyl N-[5-ethylsulfonyl-1-methyl-2-(2,2,2-trifluoroethoxy)imidazol-4-yl]carbamate | 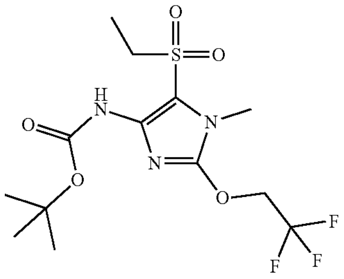 [SMILES: CCS(=O)(=O)c1c(NC(=O)OC(C)(C)C)nc(OCC(F)(F)F)n1C] | 1.10 | 288 [M + H − 100]$^+$ | 1 | |
| I-34 | 5-ethylsulfonyl-1-methyl-2-pyrimidin-5-yl-imidazole-4-carboxylic acid | 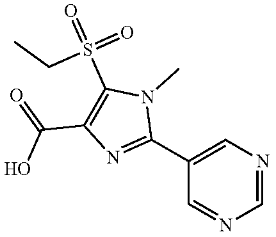 [SMILES: CCS(=O)(=O)c1c(C(=O)O)nc(-c2cncnc2)n1C] | 0.19 | 297 | 1 | |
| I-35 | tert-butyl N-(5-ethylsulfonyl-1-methyl-2-pyrimidin-5-yl-imidazol-4-yl)carbamate | 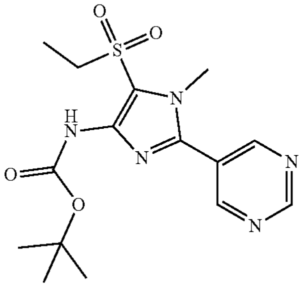 [SMILES: CCS(=O)(=O)c1c(NC(=O)OC(C)(C)C)nc(-c2cncnc2)n1C] | 0.98 | 268 [M + H − 100]$^+$ | 1 | |
| I-36 | 2-[1-(cyclopropylmethyl)pyrazol-4-yl]-5-ethylsulfonyl-1-methyl-imidazole-4-carboxylic acid | 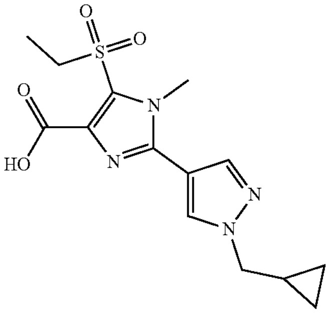 [SMILES: CCS(=O)(=O)c1c(C(=O)O)nc(-c2cnn(CC3CC3)c2)n1C] | 1.05 | 339 | 2 | |
| I-37 | tert-butyl N-[2-[1-(cyclopropylmethyl)pyrazol-4-yl]-5-ethylsulfonyl-1-methyl-imidazol-4-yl]carbamate | 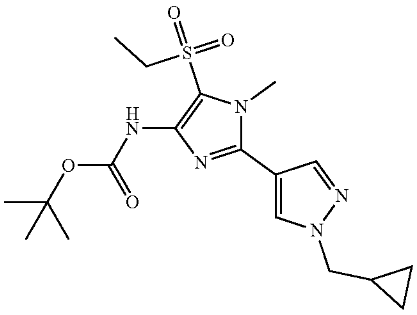 [SMILES: CCS(=O)(=O)c1c(NC(=O)OC(C)(C)C)nc(-c2cnn(CC3CC3)c2)n1C] | 1.36 | 410 | 2 | |

TABLE I-continued

| Examples of intermediates | | | | | | |
|---|---|---|---|---|---|---|
| | | | $^{1}$H NMR, LCMS | | | |
| No. | IUPAC name | Structures | $R_t$ (min) | [M + H]$^+$ or [M − H]$^-$ (measured) | Meth-od | Mp (° C.) |
| I-38 | 5-ethylsulfonyl-1-methyl-2-[1-(2,2,2-trifluoroethyl)pyrazol-4-yl]imidazole-4-carboxylic acid | 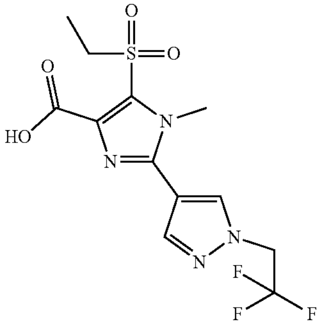 [SMILES: CCS(=O)(=O)c1c(C(=O)O)nc(-c2cnn(CC(F)(F)F)c2)n1C] | 1.00 | 367 | 2 | |
| I-39 | tert-butyl N-[5-ethylsulfonyl-1-methyl-2-[1-(2,2,2-trifluoroethyl)pyrazol-4-yl]imidazol-4-yl]carbamate | 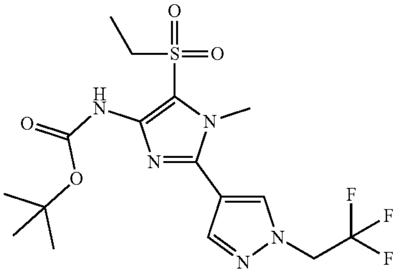 [SMILES: CCS(=O)(=O)c1c(NC(=O)OC(C)(C)C)nc(-c2cnn(CC(F)(F)F)c2)n1C] | 1.07 | 436 | 1 | |
| I-40 | tert-butyl N-(5-ethylsulfonyl-1-methyl-2-pyrimidin-2-yl-imidazol-4-yl)carbamate | 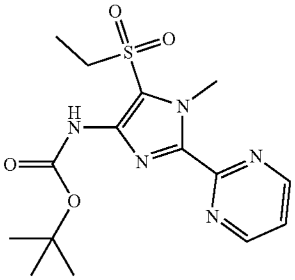 [SMILES: CCS(=O)(=O)c1c(NC(=O)OC(C)(C)C)nc(-c2ncccn2)n1C] | 1.28 | 368 | 2 | |
| I-41 | 5-ethylsulfonyl-1-methyl-2-pyrimidin-2-yl-imidazole-4-carboxylic acid | 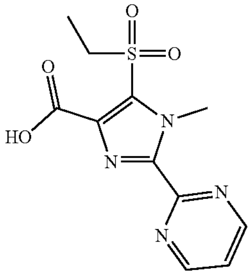 [SMILES: CCS(=O)(=O)c1c(C(=O)O)nc(-c2ncccn2)n1C] | 0.18 | 297 | 1 | |
| I-42 | tert-butyl N-[2-[1-(difluoromethyl)pyrazol-4-yl]-5-ethylsulfonyl-1-methyl-imidazol-4-yl]carbamate | 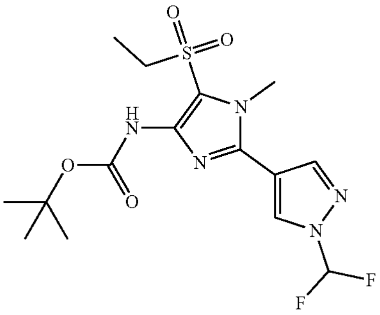 [SMILES: CCS(=O)(=O)c1c(NC(=O)OC(C)(C)C)nc(-c2cnn(C(F)F)c2)n1C] | 1.34 | 406 | 2 | |

TABLE I-continued

Examples of intermediates

| No. | IUPAC name | Structures | $^1$H NMR, LCMS R$_t$ (min) | [M + H]$^+$ or [M − H]$^-$ (measured) | Meth-od | Mp (° C.) |
| --- | --- | --- | --- | --- | --- | --- |
| I-43 | 2-[1-(difluoromethyl)pyrazol-4-(yl]-5-ethylsulfonyl-1-methyl-imidazole-4-carboxylic acid | 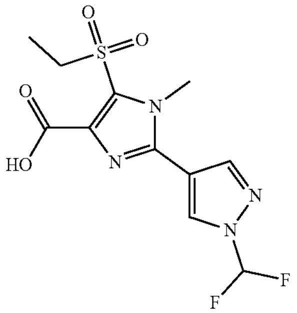 [SMILES: CCS(=O)(=O)c1c(C(=O)O)nc(-c2cnn(C(F)F)c2)n1C] | 0.16 | 335 | 1 | |
| I-44 | 2-(3-chloropyrazol-1-yl)-5-ethylsulfonyl-1-methyl-imidazol-4-amine | 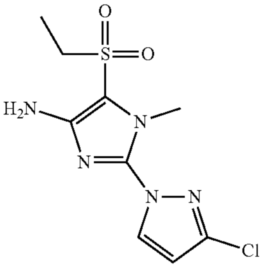 [SMILES: CCS(=O)(=O)c1c(N)nc(-n2ccc(Cl)n2)n1C] | 1.14 | 290 | 2 | |
| I-45 | tert-butyl N-[2-(3-chloropyrazol-1-yl)-5-ethylsulfonyl-1-methyl-imidazol-4-yl]carbamate | 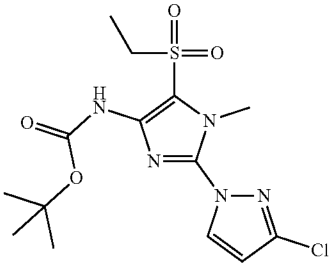 [SMILES: CCS(=O)(=O)c1c(NC(=O)OC(C)(C)C)nc(-n2ccc(Cl)n2)n1C] | 1.37 | 388 (M − H)$^-$ | 2 | |
| I-46 | 2-(3-chloropyrazol-1-yl)-5-ethylsulfonyl-1-methyl-imidazole-4-carboxylic acid | 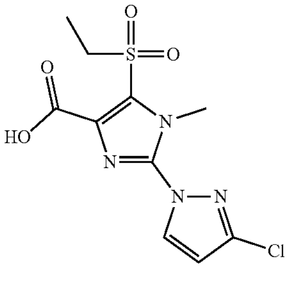 [SMILES: CCS(=O)(=O)c1c(C(=O)O)nc(-n2ccc(Cl)n2)n1C] | 0.92 | 319 | 1 | |

TABLE I-continued

| Examples of intermediates | | | | | | |
|---|---|---|---|---|---|---|
| | | | $^{1}$H NMR, LCMS | | | |
| No. | IUPAC name | Structures | $R_t$ (min) | [M + H]$^+$ or [M − H]$^-$ (measured) | Meth-od | Mp (° C.) |
| I-20 | tert-butyl N-[2-[4-(1-cyanocyclopropyl)phenyl]-5-ethylsulfonyl-1-methyl-imidazol-4-yl]carbamate | 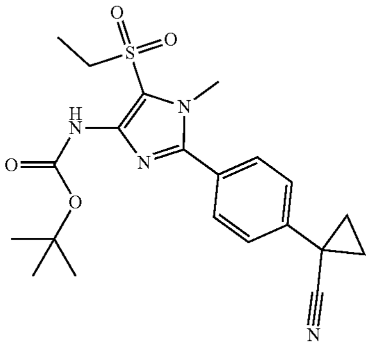 [SMILES: CCS(=O)(=O)c1c(NC(=O)OC(C)(C)C)nc(-c2ccc(C3(C#N)CC3)cc2)n1C] | 1.08 | 431 | 1 | |
| I-19 | 2-[4-(1-cyanocyclopropyl)phenyl]-5-ethylsulfonyl-1-methyl-imidazole-4-carboxylic acid | 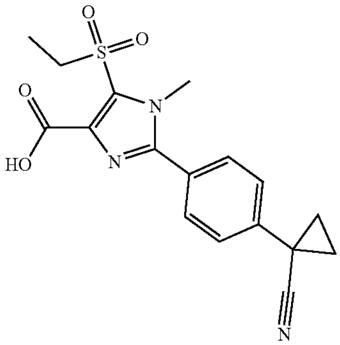 [SMILES: CCS(=O)(=O)c1c(C(=O)O)nc(-c2ccc(C3(C#N)CC3)cc2)n1C] | 0.94 | 360 | 1 | |
| I-7 | tert-butyl N-[5-(1-cyanocyclopropyl)-3-ethylsulfanyl-2-pyridyl]carbamate | 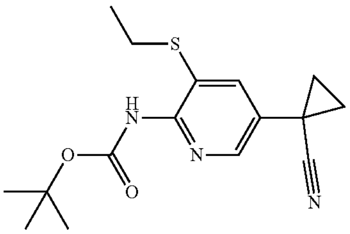 [SMILES: CCSc1cc(C2(C#N)CC2)cnc1NC(=O)OC(C)(C)C] | 0.96 | 264 [(M + H)$^+$ − 56] | 3 | |
| I-8 | 1-(6-amino-5-ethylsulfanyl-3-pyridyl)cyclopropane-carbonitrile | 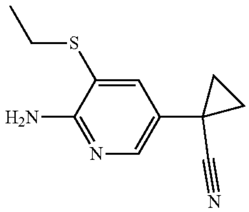 | 0.25 | 220 | 3 | |
| I-9 | 1-(6-amino-5-ethylsulfonyl-3-pyridyl)cyclopropane-carbonitrile | 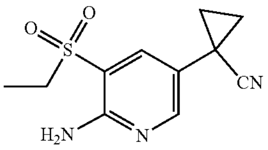 [SMILES: CCS(=O)(=O)c1cc(C2(C#N)CC2)cnc1N] | 0.76 | 252 | 1 | |

TABLE I-continued

Examples of intermediates

| No. | IUPAC name | Structures | $^1$H NMR, LCMS R$_t$ (min) | [M + H]$^+$ or [M − H]$^-$ (measured) | Meth-od | Mp (° C.) |
|---|---|---|---|---|---|---|
| I-10 | tert-butyl N-[5-(1-cyanocyclopropyl)-3-ethylsulfonyl-2-pyridyl]carbamate | 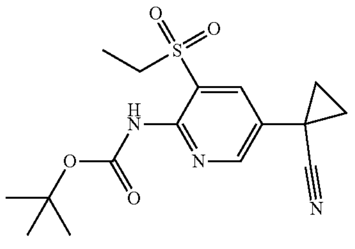 [SMILES: CCS(=O)(=O)c1cc(C2(C#N)CC2)cnc1NC(=O)OC(C)(C)C] | 0.97 | 296 [(M + H)$^+$ − 56] | 1 | |
| I-48 | 6-cyclopropyl-3-ethylsulfonyl-pyridine-2-carboxylic acid | 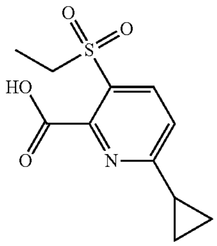 [SMILES: CCS(=O)(=O)c1ccc(C2CC2)nc1C(=O)O] | 0.66 | 256 | 1 | |
| I-49 | 5-(1,1-difluoroethyl)-3-ethylsulfonyl-pyridine-2-carboxylic acid | 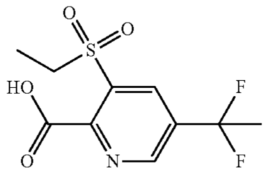 [SMILES: CCS(=O)(=O)c1cc(C(C)(F)F)cnc1C(=O)O] | 0.77 | 280 | 2 | |
| I-50 | 3-ethylsulfonyl-5-(2,2,2-trifluoroethoxy)pyridine-2-carboxylic acid | 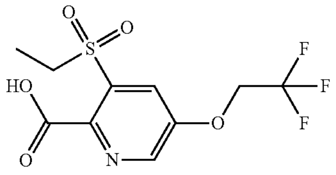 [SMILES: CCS(=O)(=O)c1cc(OCC(F)(F)F)cnc1C(=O)O] | 0.91 | 314 | 2 | |
| I-53 | tert-butyl N-[5-(1-cyano-1-methyl-ethoxy)-3-ethylsulfonyl-2-pyridyl]carbamate | 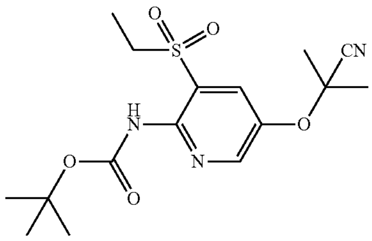 [SMILES: CCS(=O)(=O)c1cc(OC(C)(C)C#N)cnc1NC(=O)OC(C)(C)C] | 1.37 | 314 [(M + H) − 56]$^+$ | 2 | |
| I-54 | tert-butyl N-[5-(1-cyano-1-methyl-ethyl)-3-ethylsulfonyl-2-pyridyl]carbamate | 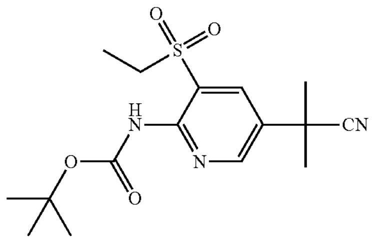 [SMILES: CCS(=O)(=O)c1cc(C(C)(C)C#N)cnc1NC(=O)OC(C)(C)C] | 1.10 | 352 | 1 | |

TABLE I-continued

| Examples of intermediates | | | | | | |
|---|---|---|---|---|---|---|
| | | | $^{1}$H NMR, LCMS | | | |
| No. | IUPAC name | Structures | $R_t$ (min) | $[M + H]^+$ or $[M - H]^-$ (measured) | Meth-od | Mp (° C.) |
| I-52 | 3-ethylsulfonyl-5-(trifluoromethyl)pyridin-2-amine | 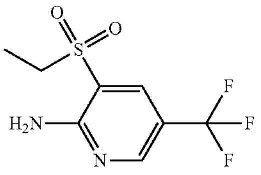 [SMILES: CCS(=O)(=O)c1cc(C(F)(F)F)cnc1N] | 0.80 | 254 | 1 | |
| I-55 | tert-butyl N-[3-ethylsulfonyl-5-(trifluoromethyl)-2-pyridyl]carbamate | 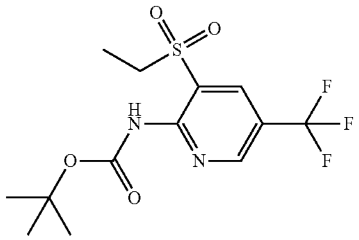 [SMILES: CCS(=O)(=O)c1cc(C(F)(F)F)cnc1NC(=O)OC(C)(C)C] | 1.17 | 353 | 1 | |
| I-56 | N-(6-amino-5-ethylsulfonyl-3-pyridyl)-N-methyl-acetamide | 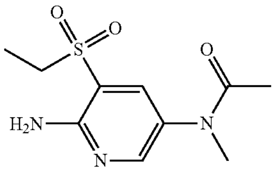 [SMILES: CCS(=O)(=O)c1cc(N(C)C(C)=O)cnc1N] | 0.17 | 258 | 1 | |
| I-57 | tert-butyl N-[5-[acetyl(methyl)amino]-3-ethylsulfonyl-2-pyridyl]carbamate | 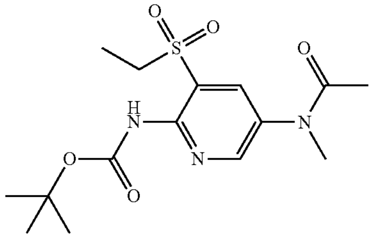 [SMILES: CCS(=O)(=O)c1cc(N(C)C(C)=O)cnc1NC(=O)OC(C)(C)C] | 1.34 | 358 | 2 | |
| I-58 | 6-cyclopropyl-3-ethylsulfonyl-pyridin-2-amine | 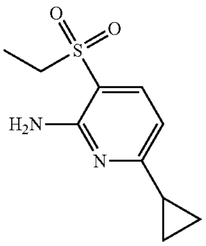 | 1.03 | 227 | 2 | |
| I-59 | tert-butyl N-(6-cyclopropyl-3-ethylsulfonyl-2-pyridyl)carbamate | 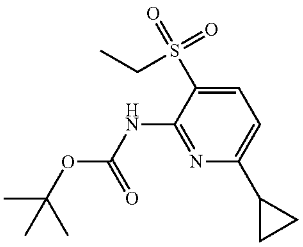 [SMILES: CCS(=O)(=O)c1ccc(C2CC2)nc1NC(=O)OC(C)(C)C] | 1.42 | 327 | 2 | |

TABLE I-continued

Examples of intermediates

| No. | IUPAC name | Structures | $^1$H NMR, LCMS $R_t$ (min) | [M + H]$^+$ or [M − H]$^-$ (measured) | Meth-od | Mp (° C.) |
|---|---|---|---|---|---|---|
| I-60 | 3-ethylsulfonyl-6-pyrimidin-2-yl-pyridin-2-amine | 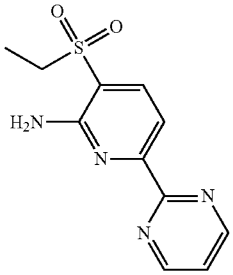 [SMILES: CCS(=O)(=O)c1ccc(-c2ncccn2)nc1N] | 1.13 | 265 | 2 | |
| I-61 | tert-butyl N-(3-ethylsulfonyl-6-pyrimidin-2-yl-2-pyridyl)carbamate | 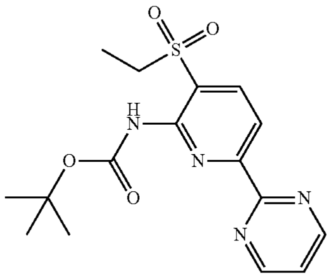 [SMILES: CCS(=O)(=O)c1ccc(-c2ncccn2)nc1NC(=O)OC(C)(C)C] | 1.17 | 363 | 1 | |
| I-62 | 5-(1,1-difluoroethyl)-3-ethylsulfonyl-pyridin-2-amine | 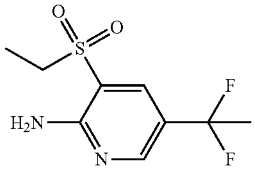 [SMILES: CCS(=O)(=O)c1cc(C(C)(F)F)cnc1N] | 1.15 | 251 | 2 | |
| I-63 | tert-butyl N-[5-(1,1-difluoroethyl)-3-ethylsulfonyl-2-pyridyl]carbamate | 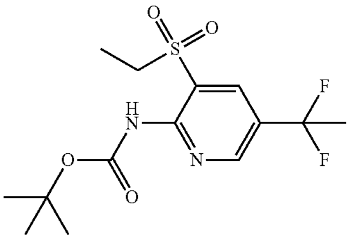 [SMILES: CCS(=O)(=O)c1cc(C(C)(F)F)cnc1NC(=O)OC(C)(C)C] | 1.08 | 349 (M − H)$^-$ | 1 | |
| I-65 | tert-butyl N-[3-ethylsulfonyl-5-(2,2,2-trifluoroethoxy)-2-pyridyl]carbamate | 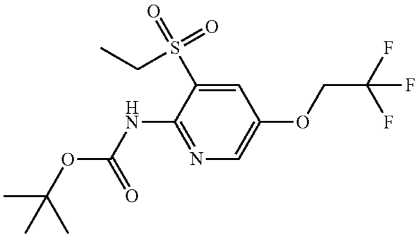 [SMILES: CCS(=O)(=O)c1cc(OCC(F)(F)F)cnc1NC(=O)OC(C)(C)C] | 1.14 | 383 (M − H)$^-$ | 1 | |
| I-67 | tert-butyl N-[5-(2,2-difluoropropoxy)-3-ethylsulfonyl-2-pyridyl]carbamate | 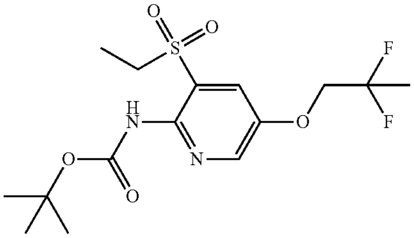 [SMILES: CCS(=O)(=O)c1cc(OCC(C)(F)F)cnc1NC(=O)OC(C)(C)C] | 1.13 | 281 [(M + H) − 100]$^+$ | 1 | |

TABLE I-continued

| Examples of intermediates | | | | | | |
|---|---|---|---|---|---|---|
| | | | $^1$H NMR, LCMS | | | |
| No. | IUPAC name | Structures | $R_t$ (min) | [M + H]$^+$ or [M − H]$^-$ (measured) | Meth-od | Mp (° C.) |
| I-2 | 6-chloro-2,2-difluoro-1,3-benzodioxole-5-carbaldehyde | 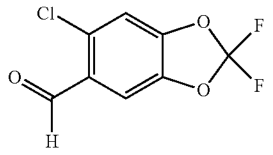 [SMILES: O=Cc1cc2c(cc1Cl)OC(F)(F)O2] | $^1$H NMR (400 MHz, $CDCl_3$) δ ppm: 7.22 (s, 1 H), 7.66 (s, 1 H), 10.41 (s, 1 H). | | | |
| I-3 | 2,2-difluoro-6-methyl-1,3-benzodioxole-5-carbaldehyde | 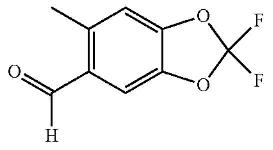 | $^1$H NMR (400 MHz, $CDCl_3$) δ ppm: 2.72 (s, 3 H), 6.99 (s, 1 H), 7.56 (s, 1 H), 10.27 (s, 1 H). | | | |
| I-4 | 2,2-difluoro-6-methyl-1,3-benzodioxole-5-carboxylic acid | 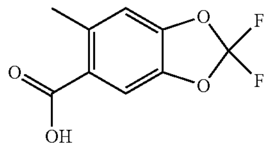 | 1.42 | 215 (M − H)$^-$ | 2 | |
| I-5 | ethyl 2,2-difluoro-6-methyl-1,3-benzodioxole-5-carboxylate | 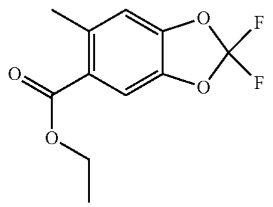 [SMILES: CCOC(=O)c1cc2c(cc1C)OC(F)(F)O2] | $^1$H NMR (400 MHz, $CDCl_3$) δ ppm: 1.41 (t, 3 H), 2.64 (s, 3 H), 4.37 (q, 2 H), 6.97 (s, 1 H), 7.67 (s, 1 H). | | | |
| I-6 | ethyl 6-(bromomethyl)-2,2-difluoro-1,3-benzodioxole-5-carboxylate | 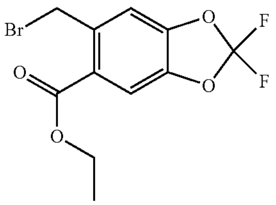 [SMILES: CCOC(=O)c1cc2c(cc1CBr)OC(F)(F)O2] | $^1$H NMR (400 MHz, $CDCl_3$) δ ppm: 1.39-1.47 (m, 3 H), 4.38-4.45 (m, 2 H), 4.97 (s, (2 H), 7.20 (s, 1 H), 7.71 (s, 1 H). | | | |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables A-1 to A-12, D-1 to D-12, E-1 to E-12 and G1 to G-12 and Table P of the present invention"):

an adjuvant selected from the group of substances consisting of petroleum oils (alternative name) (628)+TX;

an insect control active substance selected from abamectin+TX, acequinocyl+TX, acetamiprid+TX, acetoprole+TX, acrinathrin+TX, acynonapyr+TX, afidopyropen+TX, afoxolaner+TX, alanycarb+TX, allethrin+TX, alpha-cypermethrin+TX, alphamethrin+TX, amidoflumet+TX, aminocarb+TX, azocyclotin+TX, bensultap+TX, benzoximate+TX, benzpyrimoxan+TX, betacyfluthrin+TX, beta-cypermethrin+TX, bifenazate+TX, bifenthrin+TX, binapacryl+TX, bioallethrin+TX, S-bioallethrin+TX, bioresmethrin+TX, bistrifluron+TX, broflanilide+TX, brofluthrinate+TX, bromophos-ethyl+TX, buprofezine+TX, butocarboxim+TX, cadusafos+TX, carbaryl+TX, carbosulfan+TX, cartap+TX, CAS number: 1632218-00-8+TX, CAS number: 1808115-49-2+TX, CAS number:

2032403-97-5+TX, CAS number: 2044701-44-0+TX, CAS number: 2128706-05-6+TX, CAS number: 2095470-94-1+TX, CAS number: 2377084-09-6+TX, CAS number: 1445683-71-5+TX, CAS number: 2408220-94-8+TX, CAS number: 2408220-91-5+TX, CAS number: 1365070-72-9+TX, CAS number: 2171099-09-3+TX, CAS number: 2396747-83-2+TX, CAS number: 2133042-31-4+TX, CAS number: 2133042-44-9+TX, CAS number: 1445684-82-1+TX, CAS number: 1445684-82-1+TX, CAS number: 1922957-45-6+TX, CAS number: 1922957-46-7+TX, CAS number: 1922957-47-8+TX, CAS number: 1922957-48-9+TX, CAS number: 2415706-16-8+TX, CAS number: 1594624-87-9+TX, CAS number: 1594637-65-6+TX, CAS number: 1594626-19-3+TX, CAS number: 1990457-52-7+TX, CAS number: 1990457-55-0+TX, CAS number: 1990457-57-2+TX, CAS number: 1990457-77-6+TX, CAS number: 1990457-66-3+TX, CAS number: 1990457-85-6+TX, CAS number: 2220132-55-6+TX, CAS number: 1255091-74-7+TX, chlorantraniliprole+TX, chlordane+TX, chlorfenapyr+TX, chloroprallethrin+TX, chromafenozide+TX, clenpirin+TX, cloethocarb+TX, clothianidin+TX, 2-chlorophenyl N-methylcarbamate (CPMC)+TX, cyanofenphos+TX, cyantraniliprole+TX, cyclaniliprole+TX, cyclobutrifluram+TX, cycloprothrin+TX, cycloxaprid+TX, cyenopyrafen+TX, cyetpyrafen+TX, cyflumetofen+TX, cyfluthrin+TX, cyhalodiamide+TX, cyhalothrin+TX, cypermethrin+TX, cyphenothrin+TX, cyproflanilide+TX, cyromazine+TX, deltamethrin+TX, diafenthiuron+TX, dialifos+TX, dibrom+TX, dicloromezotiaz+TX, diflovidazine+TX, diflubenzuron+TX, dimpropyridaz+TX, dinactin+TX, dinocap+TX, dinotefuran+TX, dioxabenzofos+TX, emamectin (or emamectin benzoate)+TX, empenthrin+TX, epsilon-momfluorothrin+TX, epsilon-metofluthrin+TX, esfenvalerate+TX, ethion+TX, ethiprole+TX, etofenprox+TX, etoxazole+TX, famphur+TX, fenazaquin+TX, fenfluthrin+TX, fenmezoditiaz+TX, fenitrothion+TX, fenobucarb+TX, fenothiocarb+TX, fenoxycarb+TX, fenpropathrin+TX, fenpyroximate+TX, fensulfothion+TX, fenthion+TX, fentinacetate+TX, fenvalerate+TX, fipronil+TX, flometoquin+TX, flonicamid+TX, fluacrypyrim+TX, fluazaindolizine+TX, fluazuron+TX, flubendiamide+TX, flubenzimine+TX, fluchlordiniliprole+TX, flucitrinate+TX, flucycloxuron+TX, flucythrinate+TX, fluensulfone+TX, flufenerim+TX, flufenprox+TX, flufiprole+TX, fluhexafon+TX, flumethrin+TX, fluopyram+TX, flupentiofenox+TX, flupyradifurone+TX, flupyrimin+TX, fluralaner+TX, fluvalinate+TX, fluxametamide+TX, fosthiazate+TX, gamma-cyhalothrin+TX, Gossyplure™+TX, guadipyr+TX, halofenozide+TX, halfenprox+TX, heptafluthrin+TX, hexythiazox+TX, hydramethylnon+TX, imicyafos+TX, imidacloprid+TX, imiprothrin+TX, indazapyroxamet+TX, indoxacarb+TX, iodomethane+TX, iprodione+TX, isocycloseram+TX, isothioate+TX, ivermectin+TX, kappa-bifenthrin+TX, kappa-tefluthrin+TX, lambda-cyhalothrin+TX, lepimectin+TX, lotilaner+TX, lufenuron+TX, metaflumizone+TX, metaldehyde+TX, metam+TX, methomyl+TX, methoxyfenozide+TX, metofluthrin+TX, metolcarb+TX, mexacarbate+TX, milbemectin+TX, momfluorothrin+TX, niclosamide+TX, nicofluprole+TX; nitenpyram+TX, nithiazine+TX, omethoate+TX, oxamyl+TX, oxazosulfyl+TX, parathion-ethyl+TX, permethrin+TX, phenothrin+TX, phosphocarb+TX, piperonylbutoxide+TX, pirimicarb+TX, pirimiphos-ethyl+TX, pirimiphos-methyl+TX, Polyhedrosis virus+TX, prallethrin+TX, profenofos+TX, profluthrin+TX, propargite+TX, propetamphos+TX, propoxur+TX, prothiophos+TX, protrifenbute+TX, pyflubumide+TX, pymetrozine+TX, pyraclofos+TX, pyrafluprole+TX, pyridaben+TX, pyridalyl+TX, pyrifluquinazon+TX, pyrimidifen+TX, pyriminostrobin+TX, pyriprole+TX, pyriproxyfen+TX, resmethrin+TX, sarolaner+TX, selamectin+TX, silafluofen+TX, spinetoram+TX, spinosad+TX, spirodiclofen+TX, spiromesifen+TX, spiropidion+TX, spirotetramat+TX, spidoxamat+TX, sulfoxaflor+TX, tebufenozide+TX, tebufenpyrad+TX, tebupirimiphos+TX, tefluthrin+TX, temephos+TX, tetrachlorantraniliprole+TX, tetradiphon+TX, tetramethrin+TX, tetramethylfluthrin+TX, tetranactin+TX, tetraniliprole+TX, theta-cypermethrin+TX, thiacloprid+TX, thiamethoxam+TX, thiocyclam+TX, thiodicarb+TX, thiofanox+TX, thiometon+TX, thiosultap+TX, tigolaner+TX, tioxazafen+TX, tolfenpyrad+TX, toxaphene+TX, tralomethrin+TX, transfluthrin+TX, triazamate+TX, triazophos+TX, trichlorfon+TX, trichloronate+TX, trichlorphon+TX, triflumezopyrim+TX, tyclopyrazoflor+TX, zeta-cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, azadirachtin+TX, *Bacillus aizawai*+TX, *Bacillus* chitinosporus AQ746 (NRRL Accession No B-21 618)+TX, *Bacillus firmus*+TX, *Bacillus kurstaki*+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, pyrethrum+TX, QRD 420 (a terpenoid blend)+TX, QRD 452 (a terpenoid blend)+TX, QRD 460 (a terpenoid blend)+TX, Quillaja *saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp.;

an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX;

a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp.

*japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces* fumosoroseus (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX;

an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX;

a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S-methyl (6)+TX, probenazole (658) and *Reynoutria sachalinensis* extract (alternative name) (720)+TX;

a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX; a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX;

a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, EI 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+

TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothio-phene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, anisiflupurin+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, -sodium fluoroacetate+TX, thallium sulfate+TX, warfarin+TX, -2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, chloroinconazide+TX, mercuric oxide+TX, thiophanate-methyl+TX, azaconazole+TX, bitertanol+TX, bromuconazole+TX, cyproconazole+TX, difenoconazole+TX, diniconazole-+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, -simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, -metalaxyl-+TX, Rmetalaxyl+TX, ofurace+TX, oxadixyl+TX, carbendazim+TX, debacarb+TX, fuberidazole-+TX, thiabendazole+TX, chlozolinate+TX, dichlozoline+TX, myclozoline-+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb-+TX, chloro-thalonil+TX, cyflufenamid+TX, cymoxanil+TX, cyclobutrifluram+TX, diclocymet+TX, diclomezine-+TX, dicloran+TX, diethofencarb+TX, dimethomorph-+TX, flumorph+TX, dithianon+TX, ethaboxam+TX, etridiazole+TX, famoxadone+TX, fenamidone+TX, fenoxanil+TX, ferimzone+TX, fluazinam+TX, flumetylsulforim+TX, fluopicolide+TX, fluoxytioconazole+TX, flusulfamide+TX, fluxapyroxad+TX, -fenhexamid+TX, fosetyl-aluminium-+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene] amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino] oxymethyl]-2-pyridyl]carbamate+TX, methyl N-[[5-[4-(2,4-dimethylphenyl)triazol-2-yl]-2-methyl-phenyl] methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, metarylpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flufenoxadiazam+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl)pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1,1,3-trimethylindan-4-yl) pyridine-3-carboxamide+TX, α-(1,1-dimethylethyl)-α-[4'-(trifluoromethoxy) [1,1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl] oxy]benzonitrile+TX, trinexapac+TX, coumoxystrobin+TX, zhongshengmycin+TX, thiodiazole copper+TX, zinc thiazole+TX, amectotractin+TX, iprodione+TX, seboctylamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl) phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifuoromethyl) tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl)methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7- methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N-[(Z)-methoxyiminomethyl]-4-[5-(trifluoromethyl)-1,2,4-oxadiazol-3-yl]benzamide+TX, N—[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria* alternate+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, Azospirillum+TX, (MicroAZ@+TX, TAZO B®)+TX, *Azotobacter*+TX, *Azotobacter* chroocuccum (Azotomeal®)+TX, *Azotobacter* cysts (Bionatural Blooming Blossoms®)+TX, *Bacillus amyloliquefaciens*+TX, *Bacillus cereus*+TX, *Bacillus* chitinosporus strain CM-1+TX, *Bacillus* chitinosporus strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis*

Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of Clavipacter *michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmominiatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, Cylindrocladium+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, Mycorrhizae spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomonas fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera litto-*

*ralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma* asperellum (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta* catarina+TX, nicotine+TX, oregano oil (MossBuster®)+TX, Pedaliaceae oil (Nematon®)+TX, pyrethrum+TX, Quillaja *saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX, 8+TX, 11 Tetradecatrienyl acetate+TX, (Z+TX,Z+TX,E)-7+TX, 11+TX, 13-Hexadecatrienal+TX, (E+TX,Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+

TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis* megidis (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-Rid®+TX, Entonem®)+TX, *Steinernema* kraussei (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, Microctonus hyperodae+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Tables A-1 to A-12, D-1 to D-12, E-1 to E-12 and G1 to G-12 and Table P with active ingredients described above comprises a compound selected from Tables A-1 to A-12, D-1 to D-12, E-1 to E-12 and G1 to G-12 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables A-1 to A-12, D-1 to D-12, E-1 to E-12 and G1 to G-12 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables A-1 to A-12, D-1 to D-12, E-1 to E-12 and G1 to G-12 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, δ ppm, 3 ppm, 1.5 ppm, 0.8 ppm or 0.2 ppm.

Example B1: Activity Against *Bemisia tabaci* (Cotton White Fly) Feeding/Contact Activity Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm: P1, P20, P22, P23, P25.

Example B2: Activity Against *Chilo suppressalis* (Striped Rice Stemborer)

24-well microtiter plates with artificial diet were treated with aqueous test solutions prepared from 10'000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control at an application rate of 200 ppm: P1, P2, P4, P6, P8, P9, P10, P11, P12, P13, P14, P15, P16, P17, P19, P20, P22, P23, P24, P25, P26.

Example B3: Activity Against *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P4, P6, P8, P9, P11, P12, P14, P15, P16, P17, P19, P20, P21, P22, P24, P25, P26.

Example B4: Activity Against *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P4, P9, P10, P12, P14, P15, P16, P17, P18, P20, P21, P22, P24, P25.

Example B5: Activity Against *Frankliniella occidentalis* (Western Flower *Thrips*) Feeding/Contact Activity Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P2.

Example B6: Activity Against *Myzus persicae* (Green Peach Aphid) Feeding/Contact Activity Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P1, P2, P4, P5, P9, P12, P14, P15, P16, P17, P18, P19, P21, P24, P25, P26.

Example B7: Activity Against *Plutella xylostella* (Diamond Back Moth)

24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm: P1, P2, P4, P5, P6, P7, P8, P9, P10, P11, P12, P13, P14, P15, P16, P17, P18, P19, P20, P21, P22, P23, P24, P25, P26.

Example B8: Activity Against *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P1, P2, P6, P8, P9, P10, P11, P12, P13, P14, P15, P16, P17, P19, P20, P21, P22, P23, P24, P25, P26.

Example B9: Activity Against *Myzus persicae* (Green Peach Aphid) Systemic Activity Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm: P4, P5, P7, P9, P14, P15, P16, P24.

Example B10: Activity Against *Carpocapsa* (*Cydia*) *Pomonella* (Codling Moth) Larvicide, Feeding/Contact Diet cubes coated with paraffin were sprayed with diluted test solutions in an application chamber. After drying off the treated cubes (10 replicates) were infested with 1 L1 larvae. Samples were incubated at 26-27° C. and checked 14 days after infestation for mortality and growth inhibition. The following compounds resulted in at least 80% mortality at an application rate of 12.5 ppm: P1, P2, P22, P23, P25.

The invention claimed is:

1. A compound of formula (I):

(I)

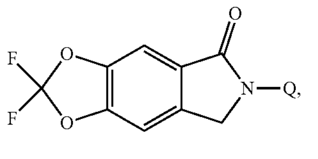

wherein

Q is a radical selected from the group consisting of formula Qa, Qb and Qc,

Qa

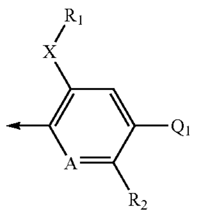

Qb

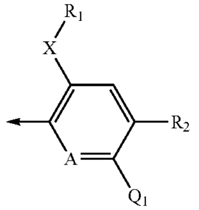

Qc

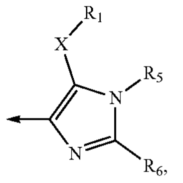

wherein the arrow denotes the point of attachment to the nitrogen atom of the tricyclic ring;

and wherein A represents CH or N;

X is S, SO, or $SO_2$;

$R_1$ is $C_1$-$C_4$alkyl, or $C_3$-$C_6$cycloalkyl-$C_1$-$C_4$alkyl;

$Q_1$ is hydrogen, halogen, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$cyanoalkoxy, $C_1$-$C_6$haloalkoxy, —$N(R_3)_2$, —$N(R_3)C({=}O)R_4$, —$N(R_3)CON(R_3)_2$, (oxazolidin-2-one)-3-yl, or 2-pyridyloxy; or $Q_1$ is a five- to six-membered aromatic or heteroaromatic ring system, linked via a ring carbon atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $Q_1$ is a five-membered heteroaromatic ring system linked via a ring nitrogen atom to the ring which contains the substituent A, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_2$ is hydrogen or $C_1$-$C_4$alkyl;

each $R_3$ independently is hydrogen, $C_1$-$C_4$alkyl, $C_1$-$C_6$haloalkyl or $C_3$-$C_6$cycloalkyl;

$R_5$ is $C_1$-$C_4$alkyl;

$R_6$ is hydrogen, halogen, $C_1$-$C_4$alkyl, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$alkoxy, $C_1$-$C_6$haloalkoxy, —$CO(NR_3R_4)$, —$NR_3COR_4$, ($C_3$-$C_5$) cycloalkyl-($C_1$-$C_6$)alkyl-, ($C_3$-$C_5$) cycloalkyl monosubstituted by cyano-($C_1$-$C_6$)alkyl-; or $R_6$ is a five- to six-membered saturated, partially saturated, or heteroaromatic ring system, linked via a ring nitrogen atom to the imidazole ring which is connected to the substitutent $R_5$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; $C_3$-$C_6$cycloalkyl, $C_3$-$C_6$cycloalkyl monosubstituted by cyano, $C_1$-$C_6$cyanoalkyl, ($C_3$-$C_5$) cycloalkyl-($C_1$-$C_6$) alkyl-, ($C_3$-$C_5$) cycloalkyl monosubstituted by cyano-($C_1$-$C_6$)alkyl-, and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom; or $R_6$ is a five- to six-membered saturated, partially saturated, aromatic or heteroaromatic ring system linked via a ring carbon atom to the imidazole ring which is connected to the substitutent $R_5$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl and $C_1$-$C_4$alkylsulfonyl; $C_3$-$C_6$cycloalkyl, $C_3$-$C_6$cycloalkyl monosubstituted by cyano, $C_1$-$C_6$cyanoalkyl, ($C_3$-$C_5$) cycloalkyl-($C_1$-$C_6$) alkyl-, ($C_3$-$C_5$) cycloalkyl monosubstituted by cyano-($C_1$-$C_6$)alkyl-, and said ring system can contain 1, 2 or 3 ring heteroatoms selected from the group consisting of nitrogen, oxygen and sulfur, where said ring system may not contain more than one ring oxygen atom and may not contain more than one ring sulfur atom; and $R_4$ is $C_3$-$C_6$cycloalkyl-$C_1$-$C_4$alkyl, $C_1$-$C_6$haloalkyl, $C_1$-$C_6$haloalkoxy or $C_3$-$C_6$cycloalkyl;

or an agrochemically acceptable salt, stereoisomer, enantiomer, tautomer or N-oxide of a compound of formula I.

2. A compound of formula I according to claim 1, represented by the compounds of formula I-A1:

I-A1

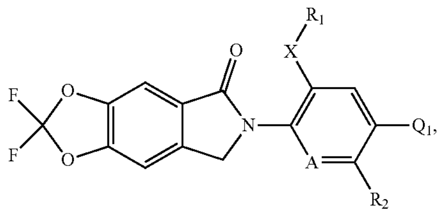

wherein A, $R_1$, $R_2$, X, $Q_1$, $R_3$ and $R_4$ are as defined under formula I in claim 1, or an agrochemically acceptable salt, stereoisomer, enantiomer, tautomer or N-oxide thereof.

3. A compound of formula I according to claim 1, represented by the compounds of formula I-A2:

I-A2

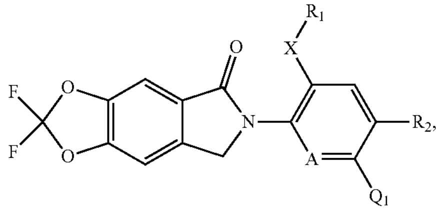

wherein A, $R_1$, $R_2$, X, $Q_1$, $R_3$ and $R_4$ are as defined under formula I in claim 1, or an agrochemically acceptable salt, stereoisomer, enantiomer, tautomer or N-oxide thereof.

4. A compound of formula I according to claim 1, represented by the compounds of formula I-B1:

I-B1

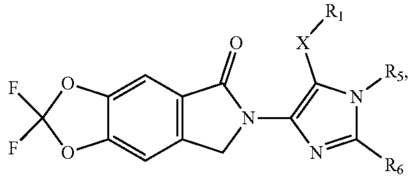

wherein X, $R_1$, $R_3$, $R_4$, $R_5$ and $R_6$ are as defined under formula I in claim 1, or an agrochemically acceptable salt, stereoisomer, enantiomer, tautomer or N-oxide thereof.

5. A compound according to claim 1, wherein: X is S or $SO_2$.

6. A compound according to claim 1, wherein: $R_1$ is ethyl or cyclopropylmethyl.

7. A compound according to claim 1, wherein:

Q is Qa;

$Q_1$ is hydrogen, halogen, trifluoromethyl, cyclopropyl, cyanocyclopropyl, cyanoisopropyl, trifluoroethoxy, (oxazolidin-2-one)-3-yl, 2-pyridyloxy, N-linked pyrazolyl which can be mono-substituted by chloro or trifluoromethyl, N-linked triazolyl, C-linked pyrimidinyl, $—N(R_3)_2$, $—N(R_3)COR_4$, or $—N(R_3)CON(R_3)_2$, in each of which $R_3$ is independently either hydrogen or methyl and $R_4$ is either methyl, ethyl or cyclopropyl and $R_2$ is hydrogen or $C_1$-$C_4$alkyl.

8. A compound according to claim 1, wherein:

Q is Qb;

$Q_1$ is hydrogen, halogen, cyclopropyl, (oxazolidin-2-one)-3-yl, N-linked pyrazolyl which can be mono-substituted by chloro or trifluoromethyl, N-linked triazolyl, C-linked pyrimidinyl, $—N(R_3)_2$, $—N(R_3)COR_4$, or $—N(R_3)CON(R_3)_2$, in each of which $R_3$ is independently either hydrogen or methyl and $R_4$ is either methyl, ethyl or cyclopropyl; and R2 is hydrogen or $C_1$-$C_4$alkyl.

9. A compound according to claim 1, wherein:

Q is Qc;

$R_6$ is hydrogen, halogen, cyclopropyl, trifluoroethoxy, $—CO(NR_3R_4)$ or $—NR_3COR_4$, in each of which $R_3$ is methyl and $R_4$ is trifluoroethoxy, N-linked pyrazolyl which can be mono-substituted by chloro, cyclopropyl or trifluoromethyl, C-linked pyrimidinyl, C-linked pyrazolyl which can be mono-substituted by cyclopropyl, difluoromethyl, difluoroethyl, cyanocyclopropylmethyl or cyclopropylmethyl, C-linked dihydroisoxazole which can be mono-substituted by chloro, trifluoromethyl or cyclopropyl, phenyl which can be mono-substituted by chloro, fluoro, cylopropyl or cylopropyl mono-substituted with cyano; and $R_5$ is $C_1$-$C_4$alkyl.

10. A compound according to claim 9, wherein:

$R_6$ is hydrogen, cyclopropyl, 2,2,2-trifluoroethoxy, $—CONCH_3(CH_2CF_3)$, $—N(CH_3)COCH_2CF_3$, or a substituent selected from J1 to J12

J1

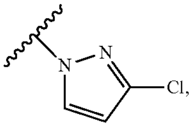

J2

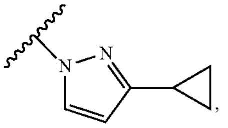

J3

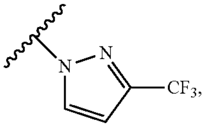

J4

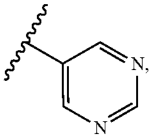

J5

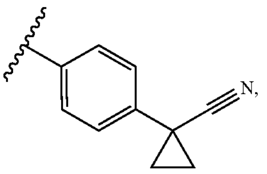

-continued

J6

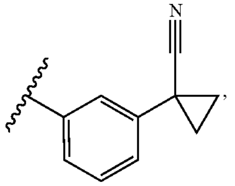

J7

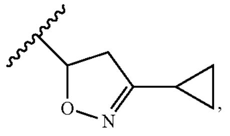

J8

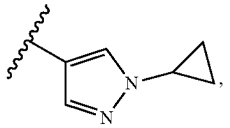

J9

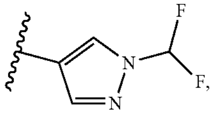

J10

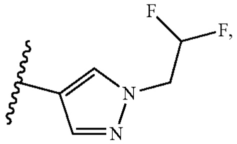

J11

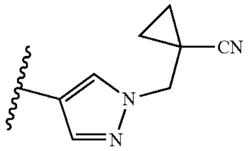

and

J12

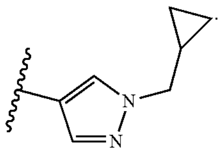

11. A compound of formula I according to claim 1, represented by the compounds of formula I-C:

(I-C)

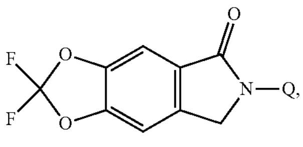

wherein

Q is a radical selected from the group consisting of formula Qa-1, Qb-1 and Qc-1, Qa-1

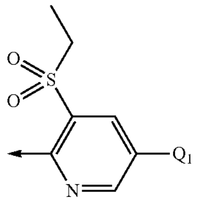

Qb-1

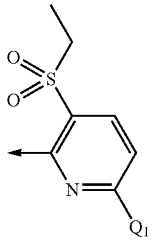

Qc-1

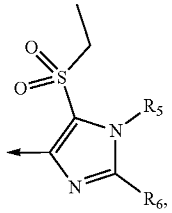

wherein the arrow denotes the point of attachment to the nitrogen atom of the tricyclic ring; and wherein $R_5$ is $C_1$-$C_6$alkyl; and each of $Q_1$ and $R_6$ are independently selected from the group consisting of cyclopropyl; cyanocyclopropyl; cyanoisopropyl; cyanoisopropoxy; $C_1$-$C_6$haloalkyl; C1-C6haloalkoxy; —$N(CH_3)COCH_3$; N-linked triazolyl; C-linked pyrimidinyl; phenyl which can be mono-substituted by cyanocylopropyl; N-linked pyrazolyl which can be mono-substituted by chloro; C-linked pyrazolyl which is N-substituted by cyclopropyl, —$CHF_2$, —$CH_2CHF_2$, —$CH_2CF_3$, —($CH_2$)-cyclopropyl, or —($CH_2$)-cyanocyclopropyl; C-linked dihydroisoxazole which can be mono-substituted by cyclopropyl; and C-linked isoxazole which can be mono-substituted by cyclopropyl.

12. A compound according to claim 1, wherein:

$Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoroethoxy; 2,2-difluoropropoxy; —$N(CH_3)COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl) pyrazol-4-yl; 1-(2,2,2-trifluoroethyl) pyrazol-4-yl; 1-cyclopropylmethylpyrazol-4-yl; 1-(1-cyanocyclopropylmethyl) pyrazol-4-yl; 3-cyclopropyl-4,5-dihydro-isoxazol-5-yl; and 3-cyclopropyl-isoxazol-5-yl.

13. A compound according to claim 1, wherein:

$R_6$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl;

2,2,2-trifluoroethoxy; 2,2-difluoropropoxy; —N($CH_3$)$COCH_3$; 1,2,4-triazol-1-yl; pyrimidin-5-yl; pyrimidin-2-yl; 4-(1-cyanocyclopropyl)phenyl; 3-chloro-pyrazol-1-yl; 1-cyclopropylpyrazol-4-yl; 1-difluoromethylpyrazol-4-yl; 1-(2,2-difluoroethyl) pyrazol-4-yl; 1-(2,2,2-trifluoroethyl) pyrazol-4-yl; 1-cyclopropylmethylpyrazol-4-yl; 1-(1-cyanocyclopropylmethyl) pyrazol-4-yl; 3-cyclopropyl-4,5-dihydro-isoxazol-5-yl; 3-cyclopropyl-isoxazol-5-yl; 3-(1-cyanocyclopropyl)phenyl; and 4-chloro-pyrazol-1-yl.

14. A compound of formula I, according to claim 1, selected from the group consisting of:

1-[6-(2,2-difluoro-7-oxo-5H-[1,3]dioxolo[4,5-f]isoindol-6-yl)-5-ethylsulfonyl-3-pyridyl]cyclopropanecarbonitrile (compound P1);

1-[4-[4-(2,2-difluoro-7-oxo-5H-[1,3]dioxolo[4,5-f]isoindol-6-yl)-5-ethylsulfonyl-1-methyl-imidazol-2-yl]phenyl]cyclopropane-carbonitrile (compound P2);

6-[2-(3-cyclopropyl-4,5-dihydroisoxazol-5-yl)-5-ethylsulfonyl-1-methyl-imidazol-4-yl]-2,2-difluoro-5H-[1,3]dioxolo[4,5-f]isoindol-7-one (compound P3);

6-[2-[1-(2,2-difluoroethyl) pyrazol-4-yl]-5-ethylsulfonyl-1-methyl-imidazol-4-yl]-2,2-difluoro-5H-[1,3]dioxolo[4,5-f]isoindol-7-one (compound P4);

1-[[4-[4-(2,2-difluoro-7-oxo-5H-[1,3]dioxolo[4,5-f]isoindol-6-yl)-5-ethylsulfonyl-1-methyl-imidazol-2-yl]pyrazol-1-yl]methyl]cyclopropanecarbonitrile (compound P5);

6-[5-ethylsulfonyl-1-methyl-2-(2,2,2-trifluoroethoxy)imidazol-4-yl]-2,2-difluoro-5H-[1,3]dioxolo[4,5-f]isoindol-7-one (compound P6);

6-(5-ethylsulfonyl-1-methyl-2-pyrimidin-5-yl-imidazol-4-yl)-2,2-difluoro-5H-[1,3]dioxolo[4,5-f]isoindol-7-one (compound P7);

6-[3-ethylsulfonyl-5-(2,2,2-trifluoroethoxy)-2-pyridyl]-2,2-difluoro-5H-[1,3]dioxolo[4,5-f]isoindol-7-one (compound P8);

6-[2-[1-(cyclopropylmethyl) pyrazol-4-yl]-5-ethylsulfonyl-1-methyl-imidazol-4-yl]-2,2-difluoro-5H-[1,3]dioxolo[4,5-f]isoindol-7-one (compound P9);

6-(6-cyclopropyl-3-ethylsulfonyl-2-pyridyl)-2,2-difluoro-5H-[1,3]dioxolo[4,5-f]isoindol-7-one (compound P10);

6-[3-ethylsulfonyl-6-(1,2,4-triazol-1-yl)-2-pyridyl]-2,2-difluoro-5H-[1,3]dioxolo[4,5-f]isoindol-7-one (compound P11);

6-[5-(2,2-difluoropropoxy)-3-ethylsulfonyl-2-pyridyl]-2,2-difluoro-5H-[1,3]dioxolo[4,5-f]isoindol-7-one (compound P12);

6-[3-ethylsulfonyl-5-(trifluoromethyl)-2-pyridyl]-2,2-difluoro-5H-[1,3]dioxolo[4,5-f]isoindol-7-one (compound P13);

6-[5-ethylsulfonyl-1-methyl-2-[1-(2,2,2-trifluoroethyl)pyrazol-4-yl]imidazol-4-yl]-2,2-difluoro-5H-[1,3]dioxolo[4,5-f]isoindol-7-one (compound P14);

6-(5-ethylsulfonyl-1-methyl-2-pyrimidin-2-yl-imidazol-4-yl)-2,2-difluoro-5H-[1,3]dioxolo[4,5-f]isoindol-7-one (compound P15);

6-(3-ethylsulfonyl-6-pyrimidin-2-yl-2-pyridyl)-2,2-difluoro-5H-[1,3]dioxolo[4,5-f]isoindol-7-one (compound P16);

6-[2-(1-cyclopropylpyrazol-4-yl)-5-ethylsulfonyl-1-methyl-imidazol-4-yl]-2,2-difluoro-5H-[1,3]dioxolo[4,5-f]isoindol-7-one (compound P17);

N-[6-(2,2-difluoro-7-oxo-5H-[1,3]dioxolo[4,5-f]isoindol-6-yl)-5-ethylsulfonyl-3-pyridyl]-N-methyl-acetamide (compound P18);

6-(5-cyclopropyl-3-ethylsulfonyl-2-pyridyl)-2,2-difluoro-5H-[1,3]dioxolo[4,5-f]isoindol-7-one (compound P19);

6-[2-[1-(difluoromethyl) pyrazol-4-yl]-5-ethylsulfonyl-1-methyl-imidazol-4-yl]-2,2-difluoro-5H-[1,3]dioxolo[4,5-f]isoindol-7-one (compound P20);

6-[2-(3-chloropyrazol-1-yl)-5-ethylsulfonyl-1-methyl-imidazol-4-yl]-2,2-difluoro-5H-[1,3]dioxolo[4,5-f]isoindol-7-one (compound P21);

2-[6-(2,2-difluoro-7-oxo-5H-[1,3]dioxolo[4,5-f]isoindol-6-yl)-5-ethylsulfonyl-3-pyridyl]-2-methyl-propanenitrile (compound P22);

6-[5-(1,1-difluoroethyl)-3-ethylsulfonyl-2-pyridyl]-2,2-difluoro-5H-[1,3]dioxolo[4,5-f]isoindol-7-one (compound P23);

6-(2-cyclopropyl-5-ethylsulfonyl-1-methyl-imidazol-4-yl)-2,2-difluoro-5H-[1,3]dioxolo[4,5-f]isoindol-7-one (compound P24);

2-[[6-(2,2-difluoro-7-oxo-5H-[1,3]dioxolo[4,5-f]isoindol-6-yl)-5-ethylsulfonyl-3-pyridyl]oxy]-2-methyl-propanenitrile (compound P25); and 6-[2-(3-cyclopropylisoxazol-5-yl)-5-ethylsulfonyl-1-methyl-imidazol-4-yl]-2,2-difluoro-5H-[1,3]dioxolo[4,5-f]isoindol-7-one (compound P26).

15. A composition comprising an insecticidally, acaricidally, nematicidally or molluscicidally effective amount of a compound of formula (I), or an agrochemically acceptable salt, stereoisomer, enantiomer, tautomer or N-oxide thereof, as defined in claim 1 and, optionally, an auxiliary or diluent.

16. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in claim 1.

17. A method for the protection of plant propagation material from the attack by insects, acarines, nematodes or molluscs, which comprises treating the propagation material or the site, where the propagation material is planted, with the composition according to claim 15.

18. A compound of formula IX-a (IX-a)

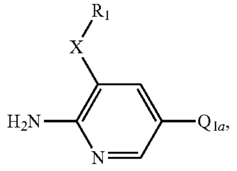

wherein

X is S, SO or $SO_2$;

$R_1$ is $C_1$-$C_4$alkyl, or $C_3$-$C_6$cycloalkyl-$C_1$-$C_4$alkyl; and

Q1a is trifluoromethyl, 1,1-difluoroethyl or —N($CH_3$)$COCH_3$.

19. A compounds of formula VI

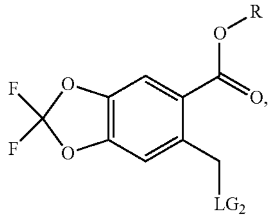

(VI)

wherein $LG_2$ is a leaving group; and

R is $C_1$-$C_6$alkyl, benzyl or phenyl.

20. A compound according to claim 1, wherein X is $SO_2$, and $R_1$ is ethyl.

21. A compound according to claim 1, wherein Q is Qa or Qb, and $R_2$ is hydrogen or methyl.

22. A compound according to claim 1, wherein $Q_1$ is selected from the group consisting of cyclopropyl; 1-cyanocyclopropyl; 1-cyano-1-methyl-ethyl; 1-cyano-1-methyl-ethoxy; trifluoromethyl; 1,1-difluoroethyl; 2,2,2-trifluoro-ethoxy; 2,2-difluoropropoxy; —$N(CH_3)COCH_3$; 1,2,4-triazol-1-yl; 1,2,4-triazol-4-yl; pyrimidin-5-yl; and pyrimidin-2-yl.

23. The compound of claim 19, wherein $LG_2$ is bromine or chlorine; and R is methyl or ethyl.

* * * * *